United States Patent
Tang et al.

(10) Patent No.: US 7,157,577 B2
(45) Date of Patent: *Jan. 2, 2007

(54) 5-SULFONAMIDO-SUBSTITUTED INDOLINONE COMPOUNDS AS PROTEIN KINASE INHIBITORS

(75) Inventors: Peng Cho Tang, Moraga, CA (US); Congxin Liang, Sunnyvale, CA (US); Todd Miller, San Marcos, CA (US); Kenneth E. Lipson, San Mateo, CA (US)

(73) Assignee: Sugen Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/793,952

(22) Filed: Mar. 8, 2004

(65) Prior Publication Data

US 2004/0204407 A1 Oct. 14, 2004

Related U.S. Application Data

(60) Provisional application No. 60/452,552, filed on Mar. 7, 2003.

(51) Int. Cl.
C07D 413/14 (2006.01)
C07D 403/14 (2006.01)
C07D 403/06 (2006.01)

(52) U.S. Cl. ............... 544/144; 514/323; 514/253.05; 514/254.09; 514/312; 514/414; 514/235.2; 544/373; 544/363; 546/201; 546/153; 548/460; 548/468; 548/455

(58) Field of Classification Search ............... 548/468, 548/460, 455; 544/373, 144, 363; 514/323, 514/253.05, 235.2, 254.09, 312, 414; 546/201, 546/153
See application file for complete search history.

(56) References Cited

U.S. PATENT DOCUMENTS

| | | | |
|---|---|---|---|
| 5,217,999 A | 6/1993 | Levitzki et al. | |
| 5,302,606 A | 4/1994 | Spada et al. | |
| 5,330,992 A | 7/1994 | Eissenstat et al. | |
| 5,792,783 A | 8/1998 | Tang et al. | |
| 6,147,106 A | 11/2000 | Tang et al. | |
| 6,395,734 B1 | 5/2002 | Tang et al. | |
| 6,465,507 B1 | 10/2002 | Tang et al. | |
| 6,486,185 B1 * | 11/2002 | McMahon et al. | 514/359 |
| 6,573,293 B1 | 6/2003 | Tang et al. | |
| 6,599,902 B1 | 7/2003 | Cui et al. | |
| 6,706,709 B1 | 3/2004 | Tang et al. | |
| 6,777,417 B1 | 8/2004 | Liang et al. | |
| 6,797,725 B1 * | 9/2004 | Sun et al. | 514/414 |
| 6,878,733 B1 * | 4/2005 | Shenoy et al. | 514/397 |
| 2002/0052369 A1 * | 5/2002 | Tang et al. | 514/233.5 |
| 2002/0107040 A1 | 8/2002 | Crandall et al. | |
| 2004/0063773 A1 * | 4/2004 | Tang et al. | 514/414 |
| 2004/0266843 A1 * | 12/2004 | Howlett et al. | 514/365 |

FOREIGN PATENT DOCUMENTS

| | | |
|---|---|---|
| WO | WO 91/15495 A1 | 10/1991 |
| WO | WO 92/20642 A1 | 11/1992 |
| WO | WO 92/21660 A1 | 12/1992 |
| WO | WO 94/03427 A1 | 2/1994 |
| WO | WO 94/14808 A1 | 7/1994 |
| WO | WO 98/07695 A1 | 2/1998 |
| WO | WO 99/11605 A1 | 3/1999 |
| WO | WO 01/37820 A2 | 5/2001 |
| WO | WO 200160814 A2 * | 8/2001 |
| WO | WO 2003015608 A2 * | 2/2003 |

OTHER PUBLICATIONS

Traxler, P., et al., "Tyrosine Kinase Inhibitors: From Rational Design to Clinical Trials," Medicinal Research Reviews, vol. 21(6), pp. 499-512 (2001), at p. 505, line 14 to p. 507, line 6, and Figure 4.*

Wang, X., et al., "Potent and selective inhibitors of the Met [hepatocyte growth factor/scatter factor (HGF/SF) receptor] tyrosine kinase block HGF/SF-induced tumor cell growth," Molec. Cancer Ther., vol. 2(11), pp. 1085-1092 (Nov. 2003), at p. 1087.*

Sun et al., J. Med. Chem. 1999, 42, 5120-5130.*

Akbasak et al., "Oncogenes: cause or consequence in the development of glial tumors," Journal of the Neurological Sciences, 1992, pp. 119-133, vol. 111, Elsevier Science Publishers B.V.

Arteaga et al., "Blockade of the Type I Somatomedin Receptor Inhibits Growth of Human Breast Cancer Cells in Athymic Mice," J. Clin. Invest., Nov. 1989, pp. 1418-1423, vol. 84, The American Society for Clinical Investigation, Inc.

Arvidsson et al., "Tyr-716 in the Platelet-Derived Growth Factor β-Receptor Kinase Insert Is Involved in GRB2 Binding and Ras Activation," Molecular and Cellular Biology, Oct. 1994, pp. 6715-6726, vol. 14, No. 10.

(Continued)

Primary Examiner—Joseph K. McKane
Assistant Examiner—Rebecca Anderson
(74) Attorney, Agent, or Firm—Bryan C. Zielinski; Vincent P. Liptak

(57) ABSTRACT

The present invention relates to 5-sulfonamido substituted indolinones that modulate the activity of protein kinases ("PKs"). The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

2 Claims, No Drawings

OTHER PUBLICATIONS

Baserga et al., "Oncogenes and the Strategy of Growth Factors," *Cell*, Dec. 16, 1994, pp. 927-930, vol. 79.

Baserga et al., "The Insulin-like Growth Factor I Receptor: A Key to Tumor Growth?" *Cancer Research*, Jan. 15, 1995, pp. 249-252, vol. 55.

Bolen et al., "Nonreceptor tyrosine protein kinases," *Oncogene*, Aug. 1993, pp. 2025-2031, vol. 8, No. 8, Macmillan Press Ltd.

Bolen et al., "The Src family of tyrosine protein kinases in hemopoietic signal transduction," *FASEB*, Dec. 1992, pp. 3403-3409, vol. 6, No. 15.

Cance et al., "Novel Protein Kinases Expressed in Human Breast Cancer," *Int. J. Cancer*, Jun. 19, 1993, pp. 571-577, vol. 54, Wiley-Liss, Inc.

Chernikova et al., "Wortmannin Sensitizes Mammalian Cells to Radiation by Inhibiting the DNA-Dependent Protein Kinase-Mediated Rejoining of Double-Strand Breaks," *Radiation Research*, 1999, pp. 159-166, vol. 151, Radiation Research Society.

Claesson-Welsh, "Signal Transduction by the PDGF Receptors," *Progress in Growth Factor Research*, 1994, pp. 37-54, vol. 5, Elsevier Science Ltd.

Coppola et al., "A Functional Insulin-Like Growth Factor I Receptor Is Required for the Mitogenic and Transforming Activities of the Epidermal Growth Factor Receptor," *Molecular and Cellular Biology*, Jul. 1994, pp. 4588-4595, vol. 14, No. 7, American Society for Microbiology.

Eng et al., "Does extracellular matrix expansion in glomerular disease require mesangial cell proliferation?" *Kidney International*, Feb. 1994, pp. S45-S47, vol. 45, Supplement 45, Blackwell Scientific Publications.

Eriksson et al., "DNA-Dependent Protein Kinase Is Inhibited by Trifluoperazine," *Biochemical and Biophysical Research Communications*, 2001, pp. 726-731, vol. 283, Academic Press.

Fantl et al., "Distinct Phosphotyrosines on a Growth Factor Receptor Bind to Specific Molecules that Mediate Different Signaling Pathways," *Cell*, May 1, 1992, pp. 413-423, vol. 69, No. 3, Cell Press.

Fingl et al., "General Principles," *The Pharmacological Basics of Therapeutics*, 5th Edition, 1975, Section I, Chapter 1, pp. 1-46, Macmillan Publishing Co., Inc.

Folkman et al., "Angiogenesis," *The Journal of Biological Chemistry*, Jun. 5, 1992, pp. 10931-10934, vol. 267, No. 16, The American Society for Biochemistry and Molecular Biology, Inc., USA.

Folkman, "What is the Evidence that Tumors are Angiogenesis Dependent," *Journal of the National Cancer Institute*, Jan. 3, 1990, pp. 4-6, vol. 82, No. 1.

Gennaro (Ed.), *Remington: The Science and Practice of Pharmacy*, 20th Edition, 2000, University of the Sciences in Philadelphia, Table of Contents Only.

Goldring et al., "Cytokines and Cell Growth Control," *Critical Reviews in Eukaryotic Gene Expression*, 1991, pp. 301-326, vol. 1, Issue 4, CRC Press, Inc.

http://www.ncbi.nlm.nih.gov, P78527 "DNA-dependent protein kinase catalytic sub unit Accession P78527" (retrieved from Internet Sep. 1, 2004).

Hu et al., "Interaction of Phosphatidylinositol 3-Kinase-Associated p85 with Epidermal Growth Factor and Platelet-Derived Growth Factor Receptors," *Molecular and Cellular Biology*, Mar. 1992, pp. 981-990, vol. 12, No. 3, American Society for Microbiology.

Izzard et al., "Competitive and Noncompetitive Inhibition of the DNA-dependent Protein Kinase," *Cancer Research*, Jun. 1, 1999, pp. 2581-2586, vol. 59.

Jellinek et al., "Inhibition of Receptor Binding by High-Affinity RNA Ligands to Vascular Endothelial Growth Factor," *Biochemistry*, Aug. 30, 1994, pp. 10450-10456, vol. 33, No. 34.

Kashishian et al., "Phosphorylation Sites at the C-terminus of the Platelet-Derived Growth Factor Receptor Bind Phospholipase Cγ1," *Molecular Biology of the Cell*, Jan. 1993, pp. 49-57, vol. 4, The American Society for Cell Biology.

Kashishian et al., "Phosphorylation sites in the PDGF receptor with difference specificities for binding GAP and PI3 kinase *in vivo*," *The EMBO Journal*, 1992, pp. 1373-1382, vol. 11, No. 4.

Kazlauskas et al., "The 64-kDa protein that associates with the platelet-derived growth factor receptor β subunit via Tyr-1009 is the SH2-containing phosphotyrosine phosphatase Syp," *Proc. Natl. Acad.*, Aug. 1993, pp. 6939-6942, vol. 90.

Kendall et al., "Inhibition of vascular endothelial cell growth factor activity by an endogenously encoded soluble receptor," *Proc. Natl. Acad. Sci. USA*, Nov. 1993, pp. 10705-10709, vol. 90.

Kim et al., "Inhibition of vascular endothelial growth factor-induced angiogenesis suppresses tumour growth *in vivo*," *Nature*, Apr. 29, 1993, pp. 841-844, vol. 362, No. 6423.

Kinsella et al., "Protein Kinase C Regulates Endothelial Cell Tube Formation on Basement Membrane Matrix, Matrigel," *Experimental Cell Research*, Mar. 1992, pp. 56-62, vol. 199, No. 1, Academic Press, Inc.

Klagsbrun et al., "VEGF/VPF: the angiogenesis factor found?" *Current Biology*, 1993, pp. 699-702, vol. 3, No. 10.

Koch et al., "SH2 and SH3 Domains: Elements That Control Interactions of Cytoplasmic Signaling Proteins," *Science*, May 3, 1991, pp. 668-674, vol. 252.

Korc et al., "Overexpression of the Epidermal Growth Factor Receptor in Human Pancreatic Cancer is Associate with Concomitant Increases in the Levels of Epidermal Growth Factor and Transforming Growth Factor Alpha," *J. Clin. Invest.*, Oct. 1992, pp. 1352-1360, vol. 90, The American Society for Clinical Investigation, Inc.

Kumabe et al., "Amplification of α-platelet-derived growth factor receptor gene lacking an exon coding for a portion of the extracellular region in a primary brain tumor of glial origin," *Oncogene*, 1992, pp. 627-633, vol. 7, Macmillan Press Ltd.

Lee et al., "Intracellular Retention of Membrane-anchored v-*sis* Protein Abrogates Autocrine Signal Transduction," *The Journal of Cell Biology*, Sep. 1992, pp. 1057-1070, vol. 118, No. 5, The Rockefeller University Press.

Macaulay et al., "Autocrine Function for Insulin-like Growth Factor I in Human Small Cell Lung Cancer Cell Lines and Fresh Tumor Cells," *Cancer Research*, Apr. 15, 1990, pp. 2511-2517, vol. 50.

March, "Stereochemistry," *Advanced Organic Chemistry:Reactions, Mechanisms, and Structure*, 4th Edition, Chapter 4, 1992, pp. 94-164, John Wiley & Sons, USA.

Mariani et al., "Inhibition of angiogenesis by FCE 26806, a potent tyrosine kinase inhibitor," *Proceedings of the American Association for Cancer Research*, Mar. 1994, p. 381, Abstract No. 2268, vol. 35.

Nishimura et al., "Two Signaling Molecules Share a Phosphotyrosine-Containing Binding Site in the Platelet-Derived Growth Factor Receptor," *Molecular and Cellular Biology*, Nov. 1993, pp. 6889-6896, vol. 13, No. 11.

Plowman et al., "Receptor Tyrosine Kinases as Targets for Drug Intervention," *DN & P*, Aug. 1994, pp. 334-339, vol. 7, No. 6.

Rozakis-Adcock et al., "Association of the Shc and Grb2/Sem5 SH2-containing proteins is implicated in activation of the Ras pathway by tyrosine kinases," *Nature*, Dec. 17, 1992, pp. 689-692, vol. 360.

Rygaard et al., "Heterotransplantation of a Human Malignant Tumour to "Nude" Mice," *Acta Path. Microbiol. Scand.*, 1969, pp. 758-760, vol. 77.

Sandberg-Nordqvist et al., "Characterization of Insulin-like Growth Factor 1 in Human Primary Brain Tumors," *Cancer Research*, Jun. 1, 1993, pp. 2475-2478, vol. 53.

Schlessinger et al., "Growth Factor Signaling by Receptor Tyrosine Kinases," *Neuron*, Sep. 1992, pp. 383-391, vol. 9, No. 3, Cell Press.

Slamon et al., "Studies of the HER-2/*neu* Proto-oncogene in Human Breast and Ovarian Cancer," *Science*, May 12, 1989, pp. 707-712, vol. 244.

Songyang et al., "Specific Motifs Recognized by the SH2 Domains of Csk, 3BP2, fps/fes, GRB-2, HCP, SHC, Syk, and Vav," *Molecular and Cellular Biology*, Apr. 1994, pp. 2777-2785, vol. 14, No. 4.

Songyang et al., "SH2 Domains Recognize Specific Phosphopeptide Sequences," *Cell*, Mar. 12, 1993, pp. 767-778, vol. 72, No. 5, Cell Press.

Stockley et al., "Synthesis, Crystal Structure Determination, and Biological Properties of the DNA-dependent Protein Kinase (DNA-PK) Inhibitor 3-Cyano-6-hydrazonomethyl-5-(4-pyridyl)pyrid-[1$H$]-2-one (OK-1035)," *Bioorganic & Medicinal Chemistry Letters*, 2001, pp. 2837-2841, vol. 11, Elsevier Science Ltd.

Takano et al., "Inhibition of Angiogenesis by a Novel Diaminoanthraquinone that Inhibits Protein Kinase," *Mol. Bio. Cell*, 1993, p. 358a, Abstract No. 2076, vol. 4.

Take et al., "Ok-1035, A Selective Inhibitor of DNA-Dependent Protein Kinase," *Biochemical and Biophysical Research Communications*, Oct. 4, 1995, pp. 41-47, vol. 215, No. 1, Academic Press, Inc.

Tejani et al., (Eds.), "Concepts and Controversies in Pediatric Renal Transplantation," *Kidney International*, Oct. 1993, vol. 44, Supplement 43, Blackwell Scientific Publications, Table of Contents Only.

Torp et al., "Expression of the epidermal growth factor receptor gene in human brain metastases," *APMIS*, Aug. 1992, pp. 713-719, vol. 100, No. 8.

Tuzi et al., "Expression of growth factor receptors in human brain tumours," *Br. J. Cancer*, 1991, pp. 227-233, vol. 63, Macmillan Press Ltd.

Twamley-Stein et al., "The Src family tyrosine kinases are required for platelet-derived growth factor-mediated signal transduction in NIH 3T3 cells," *Proc. Natl. Acad. Sci. USA*, Aug. 1993, pp. 7696-7700, vol. 90.

Voller et al., "Enzyme-Linked Immunosorbent Assay," *Manual of Clinical Immunology*, 2nd Edition, 1980, Chapter 45, pp. 359-371, American Society for Microbiology.

Weidner et al., "Tumor Angiogenesis and Metastasis—Correlation in Invasive Breast Carcinoma," *The New England Journal of Medicine*, Jan. 3, 1991, pp. 1-8, vol. 324, No. 1, Massachusetts Medical Society.

Wright et al., "Inhibition of Angiogenesis In Vitro and In Ovo With an Inhibitor of Cellular Protein Kinases, MDL 27032," *Journal of Cellular Physiology*, Sep. 1992, pp. 448-457, vol. 152, No. 3, Wiley-Liss.

\* cited by examiner

5-SULFONAMIDO-SUBSTITUTED INDOLINONE COMPOUNDS AS PROTEIN KINASE INHIBITORS

CROSS-REFERENCE TO RELATED PATENT APPLICATIONS

The present application claims priority to U.S. Provisional Application No. 60/452,552, filed Mar. 7, 2003, the contents of which are hereby incorporated by reference in their entirety and for all purposes.

FIELD OF INVENTION

The present invention relates to certain 5-sulfonamido-substituted indolinones which modulate the activity of protein kinases ("PKs"). The compounds of this invention are therefore useful in treating disorders related to abnormal PK activity. Pharmaceutical compositions comprising these compounds, methods of treating diseases utilizing pharmaceutical compositions comprising these compounds and methods of preparing them are also disclosed.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron* 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR, (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

Another RTK subfamily is referred to as the platelet derived growth factor receptor ("PDGFR") group, which includes PDGFRα, PDGFRβ, CSFIR, c-kit and flt-3. These receptors consist of glycosylated extracellular domains composed of 5 immunoglobin-like loops and an intracellular domain wherein the tyrosine kinase domain is interrupted by a kinase inert domain.

Another group which, because of its similarity to the PDGFR subfamily, is sometimes subsumed into the latter group is the fetal liver kinase ("flk") receptor subfamily. This group, containing extracellulos immunoglobulin loops made up of kinase insert domain-receptor fetal liver kinase-1 (KDR/FLK-1), and fins-like tyrosine kinase 1 (flt-1 and flt-4).

A further member of the tyrosine kinase growth factor receptor family is the fibroblast growth factor ("FGF") receptor subgroup. This group consists of four receptors, FGFR1–4, and many ligands. Although there is considerable alternative splicing, generally the receptors consist of a glycosylated extracellular domain containing 3 immunoglobin-like loops and an intracellular domain in which the tyrosine kinase sequence is interrupted by regions of a kinase insert domain.

Still another member of the tyrosine kinase growth factor receptor family is MET, often referred to as c-Met also known as human hepatocyte growth factor receptor tyrosine kinase (hHGFR). c-Met is thought to play a role in primary tumor growth and metastasis.

A more complete listing of the known RTK subfamilies is described in Plowman et al., *DN&P*, 7(6):334–339 (1994), which is incorporated by reference, including any drawings, as if fully set forth herein.

In addition to the RTKs, there also exists a family of entirely intracellular PTKs called "non-receptor tyrosine kinases" or "cytoplasmic tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fak, Jak, LIMK and Ack) have been identified. The Src subfamily appear so far to be the largest group of CTKs and includes Src, Yes, Fyn, Lyn, Lck, Blk, Hck, Fgr, and Yrk. For a more detailed discussion of CTKs, see Bolen, *Oncogene*, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes. The STKs include CDk2, Raf, the ZC family of kinases, the NEK family of kinases, and BUB1.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, fibrosis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. Pat. No. 4,966,849); soluble receptors and antibodies (Application No. WO 94/10202, Kendall and Thomas, *Proc. Nat'l Acad. Sci.*, 90:10705–10709 (1994), Kim, et al., *Nature*, 362:841–844 (1993)); RNA ligands (Jelinek, et al., *Biochemistry*, 33:10450–56); Takano, et al., *Mol. Bio. Cell*, 4:358A (1993); Kinsella, et al., *Exp. Cell Res.*, 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer. However, more effective PTK inhibitors are needed.

SUMMARY OF THE INVENTION

A family of 5-sulfonamido substituted indolinone compounds have been discovered which exhibit PK modulating ability and have a salutary effect against disorders related to abnormal PK activity. It has been demonstrated that this family of compounds modulates the catalytic activity of receptor tyrosine kinases (RTKs), non-receptor protein tyrosine kinases (CTKs) and serine/threonine protein kinases (STKs).

For example, the catalytic activity of RTKs such as, without limitation, IGFR, EGFR, MET, DDR1, DDR2, HER2, HER3, HER4, IR, IGF-1R, IRR, PDGFα, PDGFRβ, CSFIR, C-Kit, Flt4, KDR/Flk-1, Flt-1, FGFR-1, FGFR-2, FGFR-3 and FGFR-4 may be modulated with the 5-sulfonamido substituted indolinones. The catalytic activity of CTKs, such as FAK, ABL, FRK, LCK, PYK2, FYN, BMX, LYN, SRC, YES, ZA may be modulated by the inventive compounds. The catalytic activity of STKs such as, without limitation, Cdk2, AUR1, PAK, RaF and ZC1 may be modulated by the inventive compounds. By affecting the catalytic activity of RTKs, CTKs and/or STKs, such compounds can interfere with the signals transduced by such proteins.

In one embodiment, the present invention relates to compounds of Formula (I):

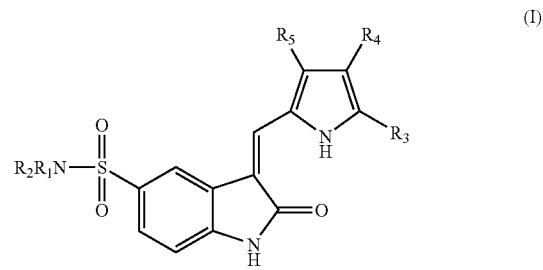

(I)

wherein $R_1$ and $R_2$ combine to form an optionally fused heterocyclic ring, which is optionally substituted by —O-alkyl, Br, Cl or F;

$R_3$, $R_4$ and $R_5$ are independently selected from the group consisting of H, lower alkyl optionally substituted with hydroxy and —(Y)$_{0-1}$—Y$_1$, wherein at least one of $R_3$, $R_4$ or $R_5$ is —(Y)$_{0-1}$—Y$_1$;

or $R_3$ and $R_4$ may combine to form a cyclic 6-membered alicyclic ring which may be substituted with one or more lower alkyl;

Y is —CH$_2$—, —CH$_2$—CH$_2$—, —CH$_2$—CH$_2$—CH$_2$— or —C(O)NHR$_6$—;

$Y_1$ is —C(O)OR', —C(O)NR$_6$R$_7$ or —NR$_6$R$_7$, where R' is H or lower alkyl;

$R_6$ and $R_7$ are independently selected from the group consisting of H and lower alkyl optionally substituted by —NR$_8$R$_9$;

or $R_6$ and $R_7$ may combine to form a heterocyclic ring which may include an additional heteroatom selected from the group consisting of N, O and S and which may be further substituted by alkyl or hydroxy;

$R_8$ and $R_9$ are independently H and lower alkyl;

or $R_8$ and $R_9$ may combine to form a heterocyclic ring which may include an additional heteroatom selected from the group consisting of N, O and S, which may be further substituted by alkyl and pharmaceutically acceptable salts thereof.

In another embodiment, the present invention relates to compounds of Formula IV and VI:

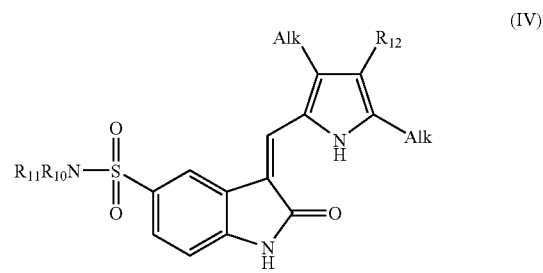

(IV)

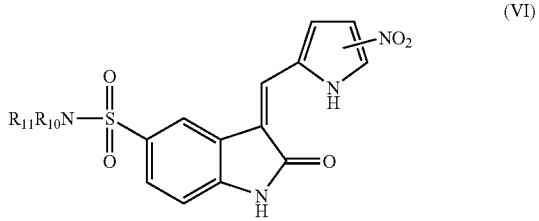

wherein $R_{10}$–$R_{11}$ are independently selected from the group consisting of H, lower alkyl, phenyl substituted with halo, thiazolyl and cycloalkyl;

$R_{12}$ is selected from the group consisting of —$CH_2$—C(O)—X'—$(CH_2)_n$—Z, —$CH_2$—Z,

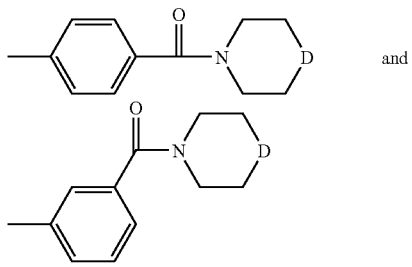

and

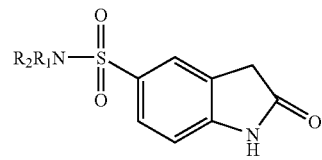

where D is O or N—$CH_3$;
X' is NH, S, O or a bond;
Z is a polar group selected from the group consisting of —C(O)$OR_{13}$, —C(O)$NR_{13}R_{14}$, amino, alkylamino, dialkylamino, piperazinyl, pyrrolidinyl and morpholinyl, Z may be further substituted by —$(CH_2)_{0-1}$—$Z_1$, where $Z_1$ is a polar group selected from the group consisting of —C(O)$OR_{13}$, —C(O)$NR_{13}R_{14}$, amino, alkylamino, dialkylamino, hydroxy, piperazinyl, pyrrolidinyl and morpholinyl; when Z is further substituted, $R_{13}$ is not present;
$R_{13}$ and $R_{14}$ are independently H and lower alkyl;
n is 0–3; and
Alk is lower alkyl of 1–4 carbons;
and pharmaceutically acceptable salts thereof.

The present invention contemplates a pharmaceutical composition, comprising a compound, of Formula (I), (IV) or (VI) and a pharmaceutically acceptable carrier or excipient.

The present invention also encompassed a method for the modulation of the catalytic activity of a protein kinase comprising contacting the protein kinase with a compound, or a pharmaceutically acceptable salt of a compound of Formula (I), (IV) or (VI).

In the method of modulation of catalytic acivitity of a protein kinase, the protein kinase is selected from the group consisting of a receptor tyrosine kinase, a non-receptor tyrosine kinase and a serine-threonine kinase.

The present invention also contemplates a method for treating or preventing a protein kinase related disorder in an organism comprising administering a therapeutically effective amount of a pharmaceutical composition comprising a compound, or a pharmaceutically acceptable salt of a compound of Formula (I), (IV) or (VI) and a pharmaceutically acceptable carrier or excipient to the organism.

In the another embodiment of the inventive method of treating or preventing a protein kinase related disorder in an organism, the protein kinase related disorder is selected from the group consisting of a receptor tyrosine kinase related disorder, a non-receptor tyrosine kinase related disorder and a serine-threonine kinase related disorder.

In another embodiment of the inventive method of treating or preventing a protein kinase related disorder in an organism, the protein kinase related disorder is selected from the group consisting of an PDGFR related disorder, a flk related disorder and a Met related disorder.

In another embodiment of the inventive method of treating or preventing a protein kinase related disorder in an organism, the protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer, gastric cancer, renal cancer, pancreatic cancer, liver cancer and gastrointestinal cancer.

In another embodiment of the inventive method of treating or preventing a protein kinase related disorder in an organism, the protein kinase related disorder is selected from the group consisting of diabetes, an autoimmune disorder, a hyperproliferation disorder, restenosis, fibrosis (including pulmonary fibrosis), psoriasis, von Hippel-Lindau disease, osteoarthritis, rheumatoid arthritis, angiogenesis, an inflammatory disorder, an immunological disorder and a cardiovascular disorder.

In a preferred embodiment of the inventive methods, the organism treated is a human.

DETAILED DESCRIPTION OF THE PREFERRED EMBODIMENTS

Definitions

Unless otherwise stated the following terms used in the specification and claims have the meanings discussed below:

"5-sulfonamido-indolinone" refers to a molecule having the chemical structure:

"Pharmaceutically acceptable salt" or "pharmaceutically acceptable salt thereof" refers to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or pharmaceutically acceptable salts or prodrugs thereof, with other chemical components, such as pharmaceutically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

"Alkynyl" refers to an aliphatic hydrocarbon having at least one carbon-carbon triple bond, including straight chain, branched chain or cyclic groups having at least one carbon-carbon triple bond. Preferably, the alkynyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

An "aralkyl" group refers to an aryl group bonded to an alkyl moiety. Examples, without limitation, include benzy, styryl and ethylbenzene. The aralkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

A "heteroalicyclic ring" or "heteroalicycle" group refers to a monocyclic or fused ring group having in the ring(s) one or more atoms selected from the group consisting of nitrogen, oxygen and sulfur. The rings may also have one or more double bonds. However, the rings may not have a completely conjugated pi-electron system. The heteroalicyclic ring may be substituted or unsubstituted. The heteroalicyclic ring may contain one or more oxo groups. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

A "heteroalicycloalkyl" group refers to a heteroalicyclic ring bonded to an alkyl moiety. Examples include without limitation —CH$_2$-morpholinyl, —CH$_2$—CH$_2$-pyrrolidinyl and —CH$_2$-piperazinyl. The heteroalicycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CX$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkoxy, —OCX$_3$, aryloxy, C(O)NH$_2$ or heteroaryl. R" is H, alkyl or aryl and n is 0–3.

X refers to a halogen group selected from the group consisting of fluorine, chlorine, bromine and iodine.

A "hydroxy" group refers to an —OH group.

A "protected hydroxy" group refers to a —OR, where the R is a protecting group, with a diol substituted compound a single protecting group can be used to form, e.g., a dioxolane (e.g., —O—CH$_2$CH$_2$—O—).

An "alkoxy" group refers to both an —O-alkyl and an —O-cycloalkyl group, as defined herein.

An "alkoxycarbonyl" refers to a —C(O)—OR.

An "aminocarbonyl" refers to a —C(O)—NRR'.

An "aryloxycarbonyl" refers to —C(O)—Oaryl.

An "aryloxy" group refers to both an —O-aryl and an —O-heteroaryl group, as defined herein.

An "arylalkyl" group refers to -alkyl-aryl, where alkyl and aryl are defined herein.

An "arylsulfonyl" group refers to a —S(O)$_n$-aryl, wherein n is 0–2.

An "alkylsulfonyl" group refer to a —S(O)$_n$-alkyl, wherein n is 0–2.

A "heteroaryloxyl" group refers to a heteroaryl-O— group with heteroaryl as defined herein.

A "heteroalicycloxy" group refers to a heteroalicyclic-O— group with heteroalicyclic as defined herein.

A "carbonyl" group refers to a —C(=O).

An "aldehyde" group refers to —C(=O)—R group where R is hydrogen.

A "thiocarbonyl" group refers to a —C(=S)—R group.

A "trihalomethanecarbonyl" group refers to a X$_3$C—C(O)— group.

A "C-carboxyl" group refers to a —C(O)O—R groups.

An "O-carboxyl" group refers to a R—C(O)O— group.

A "carboxylic acid" group refers to a C-carboxyl group in which R is hydrogen.

A "halo" or "halogen" group refers to fluorine, chlorine, bromine or iodine.

A "trihalomethyl" or a "trihaloalkyl" group refers to a —(CX$_2$)$_n$—CX$_3$ group, where n is 0 or greater.

A "trihalomethanesulfonyl" group refers to a X$_3$CS(O)$_2$ group.

A "trihalomethanesulfonamido" group refers to a X$_3$CS(O)$_2$NR— group.

A "sulfinyl" group refers to a —S(O)—R group.

A "sulfonyl" group refers to a —S(O)$_2$R group.

An "S-sulfonamido" group refers to a —S(O)$_2$NRR' group.

An "N-Sulfonamido" group refers to a —NR—S(O)$_2$R group.

An "O-carbamyl" group refers to a —OC(O)NRR' group.

An "N-carbamyl" group refers to a ROC(O)NRR' group.

An "O-thiocarbamyl" group refers to a —OC(S)NRR' group.

An "N-thiocarbamyl" group refers to a ROC(S)NR'— group.

An "amino" group refers to an —NH2 or an —NRR'group.

An "C-amido" group refers to a —C(O)NRR' group.

An "N-amido" group refers to a R'C(O)NR— group.

A "nitro" group refers to a —NO$_2$ group.

A "cyano" group refers to a —CN group.

A "silyl" group refers to a —Si(R)$_3$ group.

A "phosphonyl" group refers to a P(=O)(OR)$_2$ group.

Compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I), (IV) or (VI) may exhibit the phenomena of tautomerism and structural isomerism. For example, the compounds described herein may adopt an E or a Z configuration about any double bond in the molecule. This invention encompasses any tautomeric or structural isomeric form and mixtures thereof which possess the ability to modulate RTK, CTK and/or STK activity and is not limited to any one tautomeric or structural isomeric form.

The compound of Formula (I), (IV) or (VI) may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention wherein the polypeptide is hydrolyzed or metabolized in vivo to release the active molecule. The prodrugs of a compound of Formula (I), (IV) or (VI) are within the scope of this invention.

Additionally, it is contemplated that a compound of Formula (I), (IV) or (VI) would be metabolized by enzymes in the body of the organism such as a human being to generate a metabolite that can modulate the activity of the protein kinases. Such metabolites are within the scope of the present invention.

A general definition of "pharmaceutically acceptable salt" is set forth above. Furthermore, the term "pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cytoplasmic" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;

(2) inhibiting (that is, slowing to some extent, preferably stopping) tumor metastasis;

(3) inhibiting to some extent (that is, slowing to some extent, preferably stopping) tumor growth, and/or, (4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of the protein kinase or a change or absence of change in the interaction of the protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Preferred Embodiments

In one embodiment, the compound of the invention is selected from the group consisting of:

5-(2,3-Dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one;

2-{5-[5-[(3-Chloro-phenyl)-methyl-sulfamoyl]-2-oxo-1,2-dihydro-indol-(3Z)-ylidenemethyl]-2,4-dimethyl-1H-pyrrol-3-yl}-N-(2-diethylamino-ethyl)-acetamide;

3-[1-[3-(2-Hydroxy-ethyl)-4-(4-methyl-piperazine-1-carbonyl)-1H-pyrrol-2-yl]-meth-(Z)-ylidene]-5-(5-methoxy-2,3-dihydro-indole-1-sulfonyl)-1,3-dihydro-indol-2-one;

5-[5-(5-Methoxy-2,3-dihydro-indole-1-sulfonyl)-2-oxo-1,2-dihydro-indol-(3Z)-ylidenemethyl]-2,4-dimethyl-1H-pyrrole-3-carboxylic acid (2-diethylamino-ethyl)-amide;

5-[5-(2,3-Dihydro-indole-1-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester;

5-(2,3-Dihydro-indole-1-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one;

(3Z)-N-(3-chlorophenyl)-3-{[3,5-dimethyl-4-(3-morpholin-4-ylpropyl)-1H-pyrrol-2-yl]methylene}-N-methyl-2-oxoindoline-5-sulfonamide; and (3Z)-5-(2,3-dihydro-1H-indol-1-ylsulfonyl)-3-{[3,5-dimethyl-4-(3-morpholin-4-ylpropyl)-1H-pyrrol-2-yl]methylene}-1,3-dihydro-2H-indol-2-one.

Biological Activity

The PKs whose catalytic activity is modulated by the compounds of this invention include protein tyrosine kinases of which there are two types, receptor tyrosine kinases (RTKs) and cytoplasmic tyrosine kinases (CTKs), and serine-threonine kinases (STKs). RTK mediated signal transduction is initiated by extracellular interaction with a specific growth factor or ligand, followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, Neuron 9:303–391.

It has been shown that tyrosine phosphorylation sites on growth factor receptors function as high-affinity binding sites for SH2 (src homology) domains of signaling molecules. Fantl et al., 1992, Cell 69:413–423, Songyang et al., 1994, Mol. Cell. Biol. 14:2777–2785), Songyang et al., 1993, Cell 72:767–778, and Koch et al., 1991, Science 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, Cell 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, Cell 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. Specificity of a particular molecule for a particular PK may then arise as the result of additional interactions between the various substituents on the indolinones core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein thus have utility in in vitro assays for such proteins as well as exhibiting in vivo therapeutic effects through interaction with such proteins.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, J. Biological Chem., 267(16):10931–34. Uncontrolled vasculogenesis and/or angiogenesis has been associated with diseases such as diabetes as well as with malignant solid tumors that rely on vascularization for growth. Klagsburn & Soker, 1993, Current Biology, 3(10):699–702; Folkham, 1991, J. Natl. Cancer Inst., 82:4–6; Weidner, et al., 1991, New Engl. J. Med., 324:1–5.

Thus, the present invention provides compounds that regulate, modulate and/or inhibit vasculogenesis and/or angiogenesis by affecting the enzymatic activity of the RTKs, CTKs and STKs and interfering with the signal transduced by such RTKs, CTKs and STKs. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the RTKs, CTKs and STKs mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-1 receptor.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, Proc. Natl. Acad. Sci. USA, 90:7696–7700), phosphatidylinositol-3'-kinase (Hu et al., 1992, Mol. Cell.

Biol., 12:981–990), phospholipase cγ (Kashishian & Cooper, 1993, Mol. Cell. Biol., 4:49–51), ras-GTPase-activating protein, (Kashishian et al., 1992, EMBO J., 11:1373–1382), PTP-ID/syp (Kazlauskas et al., 1993, Proc. Natl. Acad. Sci. USA, 10 90:6939–6943), Grb2 (Arvidsson et al., 1994, Mol. Cell. Biol., 14:6715–6726), and the adapter molecules Shc and Nck (Nishimura et al., 1993, Mol. Cell. Biol., 13:6889–6896), have been shown to bind to regions involving different autophosphorylation sites. See generally, Claesson-Welsh, 1994, Prog. Growth Factor Res., 5:37–54. Thus, it is likely that signal transduction pathways activated by KDR/FLK-1 include the ras pathway (Rozakis et al., 1992, Nature, 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis, mesangial cell proliferative disorders and pulmonary fibrosis. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis. Pulmonary fibrosis may result from radiation treatment or treatment with chemotherapeutic drugs.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, Kidney International 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, Br. J. Cancer 63:227–233, Torp et al., 1992, APMIS 100:713–719) HER2/ neu (Slamon et al., 1989, Science 244:707–712) and PDGF-R (Kumabe et al., 1992, Oncogene, 7:627–633) are over-expressed in many tumors and/or persistently activated by autocrine loops. In fact, in the most common and severe cancers these receptor over-expressions (Akbasak and Suner-Akbasak et al., 1992, J. Neurol. Sci., 111:119–133, Dickson et al., 1992, Cancer Treatment Res. 61:249–273, Korc et al., 1992, J. Clin. Invest. 90:1352–1360) and autocrine loops (Lee and Donoghue, 1992, J. Cell. Biol., 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, J. Clin. Invest. 84:1418–1423) and small lung tumor cells (Macauley et al., 1990, Cancer Res., 50:2511–2517). In addition, IGF-I, while integrally involved in the normal growth and differentiation of the nervous system, also appears to be an autocrine stimulator of human gliomas. Sandberg-Nordqvist et al., 1993, Cancer Res. 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, Eukaryotic Gene Expression,1:301–326. Baserga and Coppola suggest that IGF-IR plays a central role in the mechanism of transformation and, as such, could be a preferred target for therapeutic interventions for a broad spectrum of human malignancies. Baserga, 1995, Cancer Res., 55:249–252, Baserga, 1994, Cell 79:927–930, Coppola et al., 1994, Mol. Cell. Biol., 14:4588–4595.

STKs have been implicated in many types of cancer including, notably, breast cancer (Cance, et al., Int. J. Cancer, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, DN&P 7:334–339.

As noted previously, not only RTKs but CTKs including, but not limited to, src, abl, fps, yes, fyn, lyn, lck, blk, hck, fgr and yrk (reviewed by Bolen et al., 1992, FASEB J., 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein (pp60v-src) in chicken. Moreover, its cellular homolog, the proto-oncogene pp60c-src transmits oncogenic signals of many receptors. Over-expression of EGFR or HER2/ neu in tumors leads to the constitutive activation of pp60c-src, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovasular disorders such as atherosclerosis.

Finally, both RTKs and CTKs are currently suspected as being involved in hyperimmune disorders.

The compounds and data presented are not to be construed as limiting the scope of this invention in any manner whatsoever.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I), (IV) or (VI) or a pharmaceutically acceptable salt thereof or of a pharmaceutical composition containing a compound of Formula (I), (IV) or (VI) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)2), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

At present, the therapeutically effective amounts of compounds of Formula (I), (IV) or (VI) may range from approximately 3 mg/m2 to 1500 mg/m2 per day; preferably about 3 mg/m2/ day. Even more preferably 50 mg/qm qd till 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein, or its salt or prodrug, might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); triazines, e.g., dacarbazine (used in the treatment of soft tissue sarcoma); and topoisomerase inhibitors, e.g., irinotecan hydrochloride.

A compound, salt or prodrug of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound, salt or prodrug of this invention can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound, salt or prodrug of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with mitoxantrone, paclitaxel, cyclooxygenase-2 inhibitors known in the art, in particular Celebrex®, Paracoxib®, Vioxx®, Abbott's Cox-189 disclosed in PCT Publication No. WO 99/11605, topoisomerase inhibitors such as Camptosar®, Her-2 receptor antagonist such as Herceptin®, endostatin, Gleevac®, ImClone VEGF receptor antagonist IMC C225® for the treatment of solid tumor cancers or leukemias such as, without limitation, acute myelogenous (non-lymphocytic) leukemia.

The following examples are given to illustrate the present invention. It should be understood, however, that the invention is not to be limited to the specific conditions or details described in these examples. Throughout the specification, any and all references to a publicly available documents are specifically incorporated into this patent application by reference.

SYNTHESIS EXAMPLES

General Synthetic Scheme for Preparation of Amidosulfonyl Substituted Indolinones The following general methodology may be employed to prepare the compounds of this invention.

Amidosulfonyl-indolinones were synthesized by condensation of an appropriately substituted oxindole (0.9 equivalent), an appropriately substituted pyrrole aldehyde (1 equivalent) and piperidine (excess) in ethanol (0.2M) between room temperature and 100° C. as shown in the following scheme.

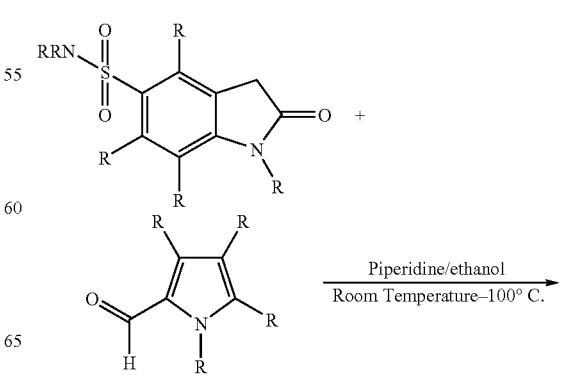

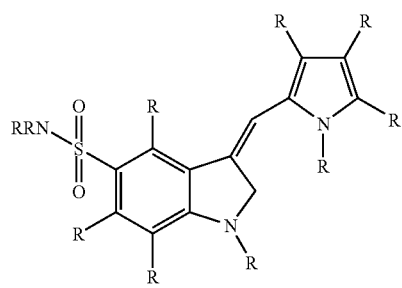

General Amidation Procedure 1

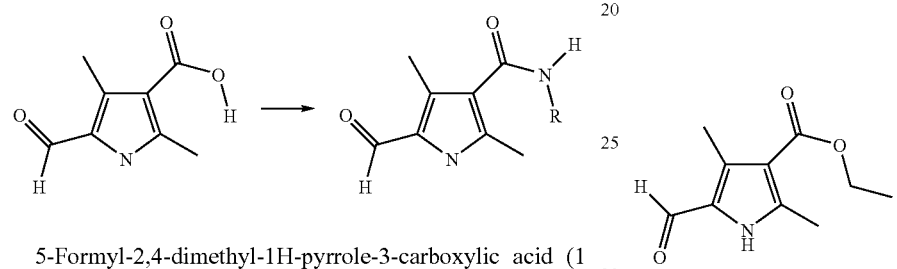

5-Formyl-2,4-dimethyl-1H-pyrrole-3-carboxylic acid (1 equivalent) is dissolved in dimethylformamide (0.3M) with stirring. To this is added 1-ethyl-3-(3-dimethylamino-propylcarbodiimide hydrochloride, 1.2 equivalents), 1-hydroxybenzotriazole (1.2 equivalents) followed by triethylamine (2 equivalents). The appropriate amine is added (1 equivalent) and the reaction stirred for 12 hours. The reaction is diluted with saturated sodium bicarbonate, sodium hydroxide solution, brine and additional solid sodium chloride and extracted twice with 10% methanol in dichloromethane. The combined organic layers are washed with brine, dried over anhydrous magnesium sulfate and concentrated. The resulting oil is re-concentrated from toluene and precipitated from diethyl ether/hexanes to afford a solid.

1. Aldehydes

A-1 5-Formyl-2,4-dimethyl-1H-pyrrole-3-carboxylic acid

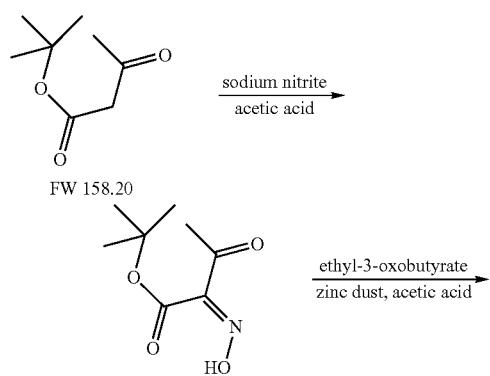

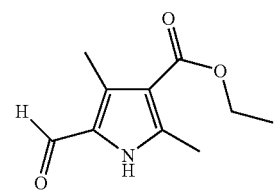

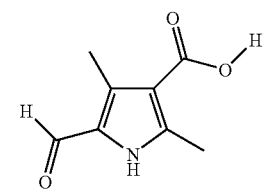

t-Butyl-3-oxobutyrate (158 g, 1 mol) was dissolved in 200 mL of acetic acid in a 500 mL 3-neck round bottom flask equipped with a thermometer, an addition funnel and mechanical stirring. The mixture was cooled in an ice bath to about 10° C. Sodium nitrite (69 g, 1 mol) was added over 75 minutes keeping the temperature under 15° C. The cold bath was removed and the mixture stirred for 30 minutes and then allowed to stand for 3.5 hours to give a solution of crude t-butyl-2-hydroximino-3-oxobutyrate.

Ethyl-3-oxobutyrate (130 g, 1 mol) was dissolved in 400 mL of acetic acid in a 2 L 3-neck round bottom flask equipped with a thermometer, an addition funnel and mechanical stirring and placed in an oil bath. Zinc dust (50 g, 0.76 mol) was added and the mixture heated to 60° C. with stirring. The crude t-butyl-2-hydroximino-3-oxobutyrate solution prepared above was cautiously added keeping the temperature at about 65° C. by slowing the addition and cooling the flask. More zinc dust (4×50 g, 3.06 mol) was added in portions during the addition with the last portion added after all the t-butyl ester had been added. The temperature of the mixture reached a maximum of 80° C. At the end of the additions the temperature was 64° C. The temperature was increased by heating to 70–75° C. for one hour and then poured into 5 L of water. The gray floating precipitate was collected by vacuum filtration and washed with 2 L of water to give 354 g of wet crude product. The crude product was dissolved in 1 L of hot methanol and hot filtered to remove zinc. The filtrate was cooled to give a precipitate that was collected by vacuum filtration to give 118 g of product. The filtrate was put in the refrigerator overnight to give a total of 173.2 g of 3,5-dimethyl-1H-pyrrole-2,4-dicarboxylic acid 2-tert-butyl ester 4-ethyl ester as an off-white solid.

3,5-Dimethyl-1H-pyrrole-2,4-dicarboxylic acid 2-tert-butyl ester 4-ethyl ester (80.1 g, 0.3 mol) and 400 mL of trifluoroacetic acid were stirred for 5 minutes in a 2 L 3-neck round bottom flask equipped with mechanical stirring and warmed to 40° C. in an oil bath. The mixture was then cooled to −5° C. and triethyl orthoformate (67.0 g, 0.45 mol) was added all at once. The temperature increased to 15° C. The mixture was stirred for about 1 minute, removed from the cold bath and then stirred for 1 hour. The trifluoroacetic acid was removed by rotary evaporation and the residue put in the refrigerator where it solidified. The solid was dissolved by warming and poured into 500 g of ice. The mixture was extracted with 800 mL of dichloromethane to give a red solution and a brown precipitate, both of which were saved. The precipitate was isolated and washed with 150 mL of saturated sodium bicarbonate solution. The dichloromethane phase was washed with 150 mL of sodium bicarbonate and both bicarbonate solutions discarded. The dichloromethane solution was washed with 3 times with 100 mL of water each time. The dichloromethane solution was evaporated to dryness and the dark residue recrystallized twice from hot ethyl acetate after decolorizing with Darco to give golden yellow needles. The brown precipitate was recrystallized from 350 mL of hot ethyl acetate after decolorizing with Darco to give a yellow-red solid. All the recrystallized solids were combined and recrystallized from 500 mL of hot ethanol to give 37.4 g (63.9%) of 5-formyl-2,4-dimethyl-1H-pyrrole-3-carboxylic acid ethyl ester as yellow needles (mp 165.6–166.3° C., lit. 163–164° C.). The evaporated residues from the ethyl acetate and ethanol mother liquors were recrystallized from 500 mL of ethanol to give 10.1 g (17.1%) of a second crop of dirty yellow needles.

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH 3. The solid was collected by filtration, washed with water and dried in a vacuum oven overnight to give 1.6 g (93%) of 5-formyl-2,4-dimethyl-1H-pyrrole-3-carboxylic acid. $^1$H NMR (300 MHz, DMSO-d6) δ 12.09 (s, br, 2H, NH & COOH), 9.59 (s, 1H, CHO), 2.44 (s, 3H, CH$_3$), 2.40 (s, 3H, CH$_3$).

A-2 3,5-Dimethyl-4-(piperazine-1-carbonyl)-1H-pyrrole-2-carbaldehyde

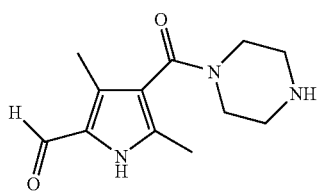

MS m/z 236 [M+1].

A-3 4-(3,5-Dimethyl-piperazine-1-carbonyl)-3,5-dimethyl-1H-pyrrole-2-carbaldehyde

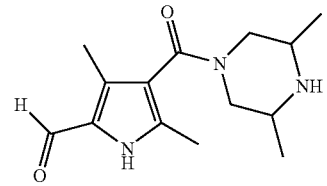

5-Formyl-2,4-dimethyl-1H-pyrrole-3-carboxylic acid (2 g, 11.96 mmol) was reacted with cis-2,6-dimethylpiperazine (2.66 g, 14.36 mmol) to give 2.27 g (72% yield) of 3,5-dimethyl-4-[(3R,5S)-3,5-dimethyl-piperazine-1-carbonyl]-1H-pyrrole-2-carbaldehyde using General Amidation Procedure 1. $^1$H-NMR (360 MHz, diemthylsulfoxide-d6) δ 11.84 (br s, 1H, NH), 9.51 (s, 1H, CHO), 4.30 (br s 1H, NH), 2.50 (m, 4H, 2×CH$_2$), 2.28 (m, 8H, 2×CH$_3$ and 2×CH), 0.96 (m, 6H, 2×CH$_3$). MS m/z 264 [M+1].

A-4 4-[4-(2-Hydroxy-ethyl)-piperazine-1-carbonyl]-3,5-dimethyl-1H-pyrrole-2-carbaldehyde

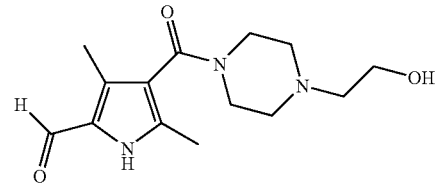

MS m/z 280 [M+1].

A-5 5-Formyl-2,4-dimethyl-1H-pyrrole-3-carboxylic acid [3-(4-methyl-piperazin-1-yl)-propyl]-amide

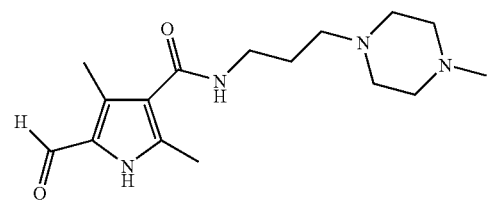

5-Formyl-2,4-dimethyl-1H-pyrrole-3-carboxylic acid (1.0 g, 6 mmol) was reacted with 1-(3-aminopropyl)-4-methylpiperazine (1.06 mL) to give 0.38 g (23% yield) of 5-formyl-2,4-dimethyl-1H-pyrrole-3-carboxylic acid [3-(4-methyl-piperazin-1-yl)-propyl]-amide using General Amidation Procedure 1. $^1$H-NMR (360 MHz, dimethylsulfoxide-d6) δ 11.8 (br s, 1H, NH), 9.52 (s, 1H, CHO), 7.52 (m, 1H, CONH), 3.2 (m, 2H, CH$_2$), 2.8 (m, 2H, CH$_2$), 2.5 (m, 8H, 4×CH$_2$), 2.34 (s, 3H, CH$_3$), 2.29 (s, 3H, CH$_3$), 1.68 (m, 2H, CH$_2$). MS m/z 307 [M+1].

A-6 5-Formyl-1H-pyrrole-2-carboxylic acid

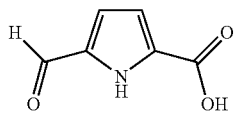

To a solution of dimethylformamide (21 mL, 0.27 mol) in 75 mL of dichloroethane was added a solution of phosphorus oxychloride (25 mL, 0.27 mol) in 75 mL of dichloroethane at 0° C. The mixture was stirred at room temperature for 30 minutes and cooled to 0–20 C. To the mixture was added a solution of ethyl pyrrole-2-carboxylate (25 g, 0.18 mol) in 50 mL of dichloroethane dropwise. The resulting mixture was stirred at room temperature for 30 minutes and then at 40° C. for 1 hour. The mixture was poured into ice and basified to pH 11 with 5 N sodium hydroxide solution. The mixture was extracted with ethyl acetate and the extract washed with water and brine and dried over anhydrous sodium sulfate. The two products were separated by column chromatography (1:3 ethyl acetate:hexane) to give 15 g (50% yield) of 5-formyl-1H-pyrrole-2-carboxylic acid ethyl ester and 2 g (7% yield) of 4-formyl-1H-pyrrole-2-carboxylic acid ethyl ester. $^1$H-NMR (300 MHz, dimethylsulfoxide) δ 13.02 (br s, 1H, NH), 9.69 (s, 1H, CHO), 6.95 (d, 1H), 6.86 (d, 1H), 4.27 (q, 2H, $CH_3$), 1.28 (t, 3H, $CH_3$). MS m/z 167 [M+].

Refluxing 4-formyl-1H-pyrrole-2-carboxylic acid ethyl ester in 2 equivalents of potassium hydroxide in methanol:water followed by acidification to pH 3 at 0° C. gave 4-formyl-1H-pyrrole-2-carboxylic acid as a solid. MS m/z 140 [M+1].

A-7 3,5-Dimethyl-4-(4-methyl-piperazine-1-carbonyl)-1H-pyrrole-2-carbaldehyde

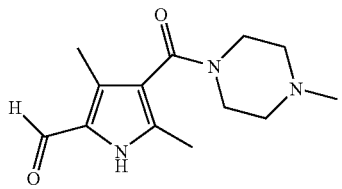

MS m/z 250 [M+1].

A-8 3,5-Dimethyl-4-(3-morpholin-4-yl-propyl)-1H-pyrrole-2-carbaldehyde

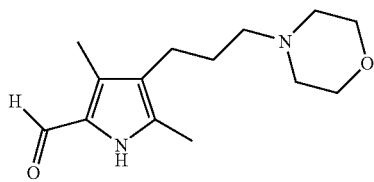

4-(2-Methoxycarbonyl-ethyl)-3,5-dimethyl-1H-pyrrole-2-carboxylic acid ethyl ester (Aldrich, 228 g, 0.9 mol) and 720 mL of 5 N sodium hydroxide were refluxed for one hour. Thin layer chromatography showed the hydrolysis to be complete. The stirred mixture was cooled to 50° C. and hydrochloric acid (10 N, 390 mL) was slowly added to give a pH of 2-3. The oil which separated solidified. The mixture was stirred and cooled to 4° C. The solids were collected by vacuum filtration, washed thoroughly with water and dried under vacuum at 40° C. to give 65.7 g (49% yield) of 3-(2,4-dimethyl-1H-pyrrol-3-yl)-propionic acid as a reddish solid.

To a suspension of 10 g (60.8 mmol) of 3-(2,4-dimethyl-1H-pyrrol-3-yl)-propionic acid in 60 mL of dichloromethane was added 11.6 gm (71.8 mmol) of 1,1'-carbonyldiimidazole followed by 5.5 mL (60.8 mmol) of morpholine and 10 mL (60.8 mmol) of N,N-diisopropylethylamine. The dark red reaction mixture was stirred at room temperature overnight and poured into ice water. The organic layer was washed with brine until its pH was 6, dried over anhydrous sodium sulfate, and concentrated. The crude product was purified on a silica gel column eluting with dichloromethane-methanol (98:2) to give 13.84 g (96% yield) of 3-(2,4-dimethyl-1H-pyrrol-3-yl)-1-morpholin-4-yl-propan-1-one.

To a suspension of 2.67 g (70 mmol) of lithium aluminum hydride in 100 mL of tetrahydrofuran was added dropwise a solution of 13.84 g (59 mmol) of 3-(2,4-dimethyl-1H-pyrrol-3-yl)-1-morpholin-4-yl-propan-1-one in 50 mL of tetrahydrofuran. The reaction mixture was stirred at 80° C. for 1 hour and cooled in an ice bath. Ice cubes were slowly added to the mixture until no more gas was generated. A few drops of 2 N sodium hydroxide were added and the reaction mixture was stirred at room temperature for 30 min, extracted with ethyl acetate and the extract dried over anhydrous sodium sulfate and concentrated to give 10.37 g (79% yield) of 4-[3-(2,4-dimethyl-1H-pyrrol-3-yl)-propyl]-morpholine as a light brown oil which was used without further purification.

To an ice-cooled solution of 5.5 mL (70 mmol) of dimethylformamide in 30 mL of dichloromethane was added 6.5 mL (70 mmol) of phosphorus oxychloride dropwise. The reaction mixture was stirred at room temperature for 15 minutes and a solution of 10.37 g (46.6 mmol) of 3,5-dimethyl-4-(3-morpholin-4-yl-propyl)-1H-pyrrole-2-carbaldehyde in 20 mL of dichloromethane was added dropwise at 0° C. The mixture was refluxed at 60° C. for 4 hours and cooled in an ice bath. Ice cubes were slowly added to the mixture followed by addition of 2 N sodium hydroxide to adjust the pH to 12. The reaction mixture was stirred at room temperature for 30 minutes and extracted with ethyl acetate. The organic layer was washed with brine, dried over anhydrous sodium sulfate and concentrated to give crude product which was purified on a silica gel column eluting with dichloromethane-methanol-ammonium hydroxide (9.5:0.5) to give 4.57 g (39% yield) of 3,5-dimethyl-4-(3-morpholin-4-yl-propyl)-1H-pyrrole-2-carbaldehyde as a dark red oil. 1H-NMR (360 MHz, dimethylsulfoxide-d6) δ 11.34 (brs, 1H, NH), 9.40 (s, 1H, CHO), 3.55 (t, 4H, 2×$CH_2$), 2.28–2.34 (m, 6H, 2×$CH_2$), 2.21 (t, 4H, 2×$CH_2$) 2.19 (s, 3H, $CH_3$), 2.14 (s, 3H, $CH_3$), 1.51 (quintet, 2H, $CH_2$). MS m/z 251 [M+1]+.

A-9 3-(2-Hydroxy-ethyl)-4-(4-methyl-piperazine-1-carbonyl)-1H-pyrrole-2-carbaldehyde

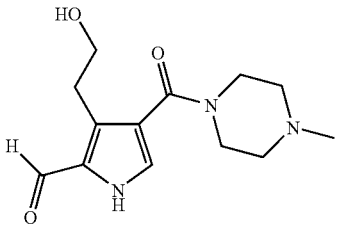

MS m/z 266 [M+1].

A-10 2-(5-Formyl-2,4-dimethyl-1H-pyrrol-3-yl)-N-(2-pyrrolidin-1-yl-ethyl)-acetamide

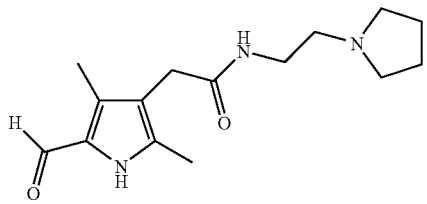

3-Acetyl-4-oxo-pentanoic acid ethyl ester (710 g, 3.81 mol), 533 mL of acetic acid and 847 g (4.00 mol) of diethyl aminomalonate hydrochloride salt were heated in an oil bath while 344 g (4.19 mol) of sodium acetate were slowly added. The internal temperature at the end of the addition was 55° C. and the mixture was thick with solids but could be stirred. The mixture was heated to 105° C. Gas evolution was vigorous. The temperature was allowed to fall to 98° C. and the reaction was stirred at this temperature for 30 minutes. Thin layer chromatography (ethyl acetate:hexane 1:2) showed the product at Rf 0.6 and a small impurity at Rf 0.7. The reaction was cooled to 50° C. and 1000 mL of ethanol and 1000 mL of water were added with stirring. The mixture was cooled in an ice bath and 3000 mL of ice water were added with stirring. The solids were collected by vacuum filtration and washed two times with 500 mL of 30% ethanol in water each time. The solids were air dried to give 870 g (93% yield) of 4-ethoxycarbonylmethyl-3,5-dimethyl-1H-pyrrole-2-carboxylic acid ethyl ester. $^1$H-NMR (dimethylsulfoxide-d6) δ 1.15, 1.26 (2×t, 2×3H, 2×CH$_3$), 2.15 (2×s, 2×3H, 2×CH$_3$), 3.32 (s, 2H, CH$_2$), 4.01, 4.18 (2×d, 2×2H, 2×CH$_2$O), 11.20 (br s, 1H, NH). MS m/z 254 [M+1].

4-Ethoxycarbonylmethyl-3,5-dimethyl-1H-pyrrole-2-carboxylic acid ethyl ester (1000 g, 3.95 mol), 2600 mL of water, 300 mL of ethanol and 700 g (11.2 mol) of potassium hydroxide were refluxed at 88–92° C. for 55 minutes. Thin layer chromatography (ethyl acetate:hexane:acetic acid 4:6:0.5) showed a new spot at the origin and the absence of starting material. The mixture was cooled to 10° C. and 1200 mL of 10 N hydrochloric acid were added to a pH of 2.5. The maximum temperature reached was 14° C. The mixture was stirred in an ice bath for 1 hour. The solids were collected by vacuum filtration and washed twice with 200 mL of water each time. The solids were used wet in the decarboxylation step.

4-Carboxymethyl-3,5-dimethyl-1H-pyrrole-2-carboxylic acid wet mixture (778 g, 3.95 mol), 880 mL of 9 N potassium hydroxide and 880 mL of water were heated to an internal temperature of 65° C., removed from the heat, and 800 mL of 10 N hydrochloric acid were slowly added with stirring to a pH of 2.5. The temperature increased to 68° C. and then decreased to 58° C. with the evolution of carbon dioxide. Thin layer chromatography (ethyl acetate:hexane:acetic acid 4:6:0.5) showed a major spot at Rf 0.7 and a small spot at the origin. The mixture was cooled to 4° C. The solids were collected by vacuum filtration and washed 3 times with 200 mL of water each time. The solid was air dried to give 240 g (40% yield) of (2,4-dimethyl-1H-pyrrol-3-yl)-acetic acid as a brown solid. $^1$H-NMR (dimethylsulfoxide-d6) δ 1.89, 2.06 (2×s, 2×3H, 2×CH$_3$), 3.17 (s, 2H, CH$_2$), 6.26 (s, 1H, pyrrole CH), 10.02 (s, 1H, NH), 11.74 (br s, 1H, COOH).

Dimethylformamide (230 mL, 3.13 mol) and 1200 mL of dichloromethane were cooled to 4° C. and 222 mL of phosphorus oxychloride was added with stirring. The temperature increased to 20° C. The mixture was cooled to 2° C. (2,4-Dimethyl-1H-pyrrol-3-yl)-acetic acid (240 g, 1.57 mol) was slowly added. The mixture was refluxed for 20 minutes. Thin layer chromatography (ethyl acetate:hexane:acetic acid 4:6:0.5) showed no starting material at Rf 0.7 and a heavy spot at the origin. The mixture was cooled to 5° C. and 1200 mL of ice water were added. The maximum temperature reached was 30° C. The mixture was stirred in an ice bath for 30 minutes. The dichloromethane layer was separated and discarded. The aqueous layer was cooled to 9° C. and adjusted to pH 12 with about 1650 mL of 9 N potassium hydroxide. The maximum temperature reached was 50° C. The mixture was cooled in an ice bath and adjusted to pH 3 with about 800 mL of 10 N hydrochloric acid. The solids were collected by vacuum filtration, washed three times with 300 mL of water each time and air dried to give 274 g (96% yield) of (5-formyl-2,4-dimethyl-1H-pyrrol-3-yl)-acetic acid as a brown solid. $^1$H-NMR (dimethylsulfoxide-d6) δ 2.15, 2.18 (2×s, 2×3H, 2×CH$_3$), 3.28 (s, 2H, CH$_2$), 9.44 (s, 1H, CHO), 11.50 (s, 1H, pyrrole NH), 12.07 (s, 1H, COOH). MS m/z 182, [M+1].

(5-Formyl-2,4-dimethyl-1H-pyrrol-3-yl)-acetic acid was reacted with 1-(2-aminoethyl)pyrrolidine using General Amidation Procedure 1 to give 2-(5-formyl-2,4-dimethyl-1H-pyrrol-3-yl)-N-(2-pyrrolidin-1-yl-ethyl)-acetamide. MS m/z 278 [M+1].

A-11 5-Formyl-2,4-dimethyl-1H-pyrrole-3-carboxylic acid (2-diethylamino-ethyl)-amide

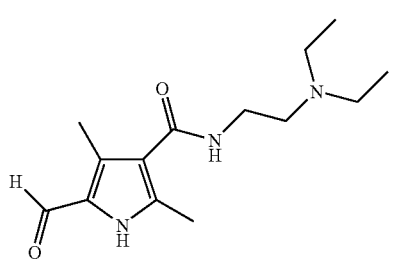

5-Formyl-2,4-dimethyl-1H-pyrrole-3-carboxylic acid (0.5 g, 2.99 mmol) was reacted with dimethylaminoethylamine (0.32 mL) to give 0.37 g (52% yield) of 5-formyl-2,4-dimethyl-1H-pyrrole-3-carboxylic acid (2-dimethylamino-ethyl)-amide by using General Amidation Procedure 1, 1H-NMR (360 MHz, dimethylsulfoxide-d6) δ 11.84 (br s, 1H, NH), 9.52 (s, 1H, CHO), 7.47 (m, 1H, NH), 3.3 (m, 2H, CH$_2$), 2.55 (m, 2H, CH$_2$), 2.35 (s, 3H, CH$_3$), 2.29 (s, 6H, 2×CH$_3$), 2.30 (s, 3H, CH$_3$). MS m/z 266 [M+1].

A-12 N-(2-Diethylamino-ethyl)-2-(5-formyl-2,4-dimethyl-1H-pyrrol-3-yl)-acetamide

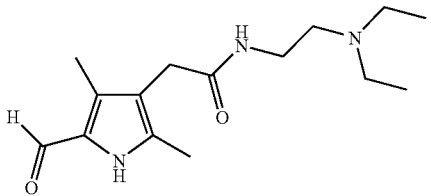

(5-Formyl-2,4-dimethyl-1H-pyrrol-3-yl)-acetic acid was reacted with diethylaminoethylamine using General Amidation Procedure 1 to give N-(2-diethylamino-ethyl)-2-(5-formyl-2,4-dimethyl-1H-pyrrol-3-yl)-acetamide. MS m/z 280 [M+1].

A-13 3-(3-Dimethylamino-propyl)-6,6-dimethyl-4,5,6,7-tetrahydro-1H-indole-2-carbaldehyde

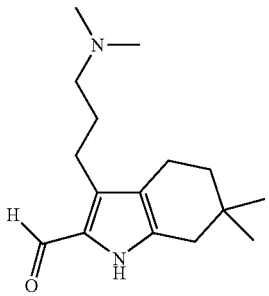

To a suspension of 3-(6,6-dimethyl-4-oxo-4,5,6,7-tetrahydro-1H-indol-3-yl)-propionic acid (1.65 g, 7 mmol) in dichloromethane (15 mL) was added 1.36 g (8.4 mmol) of carbonyldiimidazole. The mixture was stirred at room temperature until the solution became clear. To the mixture was added dimethylamine (14 mL of a 2.0M solution in tetrahydrofuran). The mixture was stirred at room temperature overnight and then concentrated. The residue was redissloved in dichloromethane, washed with brine and concentrated. The solid was washed with ethyl acetate until it became white and dried to give 1.4 g (78% yield) of 3-(6,6-dimethyl-4-oxo-4,5,6,7-tetrahydro-1H-indol-3-yl)-N,N-dimethyl-propionamide. $^1$H-NMR (360 MHz, diemthylsulfoxide-d6) δ10.93 (br s, 1H, NH), 6.48 (s, 1H), 2.94 (s, 3H, CH$_3$), 2.79 (s, 3H, CH$_3$), 2.72 (m, 2H, CH$_2$), 2.57 (s, 2H, CH$_2$), 2.48 (m, 2H, CH$_2$), 2.17 (s, 2H, CH$_2$), 1.00 (m, 6H, 2×CH$_3$). MS m/z 262 [M+].

To a suspension of 3-(6,6-dimethyl-4-oxo-4,5,6,7-tetrahydro-1H-indol-3-yl)-N,N-dimethyl-propionamide (1.2 g, 4.68 mmol) in tetrahydrofuran (30 mL) was added dropwise a solution of lithium aluminum hydride (0.69 g, 18.3 mmol) in tetrahydrofuran. The mixture was refluxed overnight. Ice was added to the cooled reaction until no more gas was generated followed by 15% sodium hydroxide and water. The reaction was stirred at room temperature for 30 minutes and the insolubles removed by vacuum filtration. The filtrate was concentrated to give [3-(6,6-dimethyl-4,5,6,7-tetrahydro-1H-indol-3-yl)-propyl]-dimethyl-amine as an oil. $^1$H-NMR (360 MHz, dimethylsulfoxide-d6) δ 9.75 (br s, 1H, NH), 6.24 (s, 1H), 3.36 (m, 2H, CH$_2$), 2.07–2.3 (m, 14H, 7×CH$_2$), 1.53 (m, 2H, CH$_2$), 1.40 (m, 2H, CH$_2$), 0.92 (s, 6H, 2×CH$_3$). MS m/z 234 [M+].

Phosphorus oxychloride (0.5 mL, 5.1 mmol) was added dropwise to ice-cooled dimethylformamide (1.1 mL, 14.1 mmol) and then stirred at room temperature for 30 minutes. A solution of [3-(6,6-dimethyl-4,5,6,7-tetrahydro-1H-indol-3-yl)-propyl]-dimethyl-amine (1.1 g, 4.6 mmol) in dimethylformamide (2 mL) was added dropwise at −5° C. The mixture was stirred at room temperature overnight. Ice cubes were added to the reaction mixture followed by the addition of 10 N potassium hydroxide to pH 11–12 and stirring for one hour. The mixture was extracted with ethyl acetate and the extract washed with brine and concentrated. The residue was chromatographed (5%-10% methanol in dichloromethane) to give 650 mg of 3-(3-dimethylamino-propyl)-6,6-dimethyl-4,5,6,7-tetrahydro-1H-indole-2-carbaldehyde as a brown solid. $^1$H-NMR (360 MHz, dimethylsulfoxide-d6) δ 11.25 (br s, 1H, NH), 9.41 (s, 1H, CHO), 2.62 (t, 2H, CH$_2$), 2.36 (t, 2H, CH$_2$), 2.30 (s, 2H, CH$_2$), 2.21 (t, 2H, CH$_2$), 2.12 (s, 6H, 2×CH$_3$), 1.60 (m, 2H, CH$_2$), 1.46 (t, 2H, CH$_2$), 0.93 (s, 6H, 2×CH$_3$). MS m/z 262 [M+].

A-14 2-(5-Formyl-2,4-dimethyl-1H-pyrrol-3-yl)-N-(2-morpholin-4-yl-ethyl)-acetamide

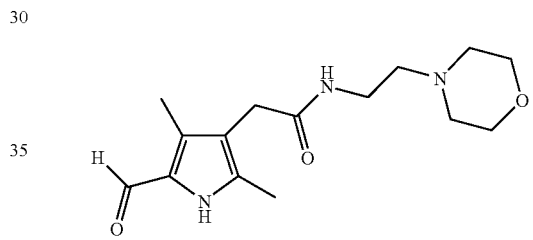

MS m/z 294 [M+1].

A-15 3-(3-Diethylamino-propyl)-6,6-dimethyl-4,5,6,7-tetrahydro-1H-indole-2-carbaldehyde

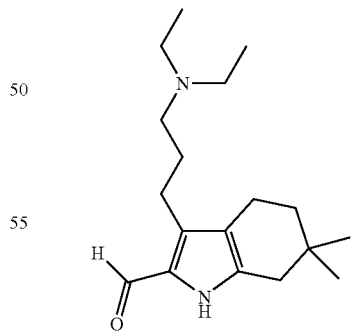

A mixture of 5-aminolevulinic acid hydrochloride (1.68 g, 10 mmol), 5,5-dimethyl-1,3-cyclohexandione (1.4 g, 10 mmol) and sodium acetate (1.64 g, 20 mmol) in water (10 mL) was heated to at 110° C. for 4 hours and then cooled. The resulting solid was collected by vacuum filtration, washed with 30% ethanol in water and dried under vacuum to give 1.6 g (68% yield) of 3-(6,6-dimethyl-4-oxo-4,5,6,7- tetrahydro-1H-indol-3-yl)-propionic acid. ¹H-NMR (360 MHz, dimethylsulfoxide-d6) δ 11.89 (br s, 1H, COOH), 10.94 (br s, 1H, NH), 6.45 (d, 1H), 2.76 (t, 2H, CH₂), 2.57 (s, 2H, CH₂), 2.44 (t, 2H, CH₂), 2.16 (s, 2H, CH₂), 0.99 (s, 6H, 2×CH₃). MS m/z 235 [M+].

To a suspension of 1.18 g of 3-(6,6-dimethyl-4-oxo-4,5, 6,7-tetrahydro-1H-indol-3-yl)-propionic acid (5 mmol) in dichloromethane (25 mL) was added 0.97 g (6 mmol) of carbonyldiimidazole. After stirring at room temperature for 2 hours, 2.1 mL (20 mmol) of diethylamine was added. The mixture was stirred at room temperature overnight. The reaction was concentrated and the residue dissolved in dichloromethane, washed with brine, dried and concentrated to give 1.2 g (83% yield) of 3-(6,6-dimethyl-4-oxo-4,5,6,7-tetrahydro-1H-indol-3-yl)-N,N-diethyl-propionamide as a white solid. ¹H-NMR (360 MHz, dimethylsulfoxide-d6) δ 10.91 (br s, 1H, NH), 6.46 (s, 1H), 3.20–3.29 (m, 4H, 2×CH₂), 2.72–2.76 (m, 2H, CH₂), 2.57 (s, 2H, CH₂), 2.45 (m, 2H, CH₂), 2.17 (s, 2H, CH₂), 0.96–1.06 (m, 12H, 4×CH₃). MS m/z 290 [M+].

To a suspension of 3-(6,6-dimethyl-4-oxo-4,5,6,7-tetrahydro-1H-indol-3-yl)-N,N-diethyl-propionamide (1.1 g, 3.8 mmol) in tetrahydrofuran (80 mL) was added dropwise a solution of lithium aluminum hydride (0.57 g, 15.1 mmol) in tetrahydrofuran. The mixture was refluxed overnight. To the cooled reaction was added enough ice until no more gas was generated followed by 15% sodium hydroxide and water. The reaction was stirred at room temperature for 30 minutes and the insolubles removed by vacuum filtration. The filtrate was concentrated to give 0.9 g of [3-(6,6-dimethyl-4,5,6,7-tetrahydro-1H-indol-3-yl)-propyl]-diethyl-amine as a light yellow oil. ¹H-NMR (360 MHz, dimethylsulfoxide-d6) δ 9.75 (br s, 1H, NH), 6.24 (s, 1H), 2.19–2.44 (m, 14H, 7×CH₂), 1.53 (m, 2H, CH₂), 1.40 (m, 2H, CH₂), 0.88–0.92 (m, 12H, 4×CH₃). MS m/z 262 [M+].

Phosphorus oxychloride (0.35 mL, 3.74 mmol) was added dropwise to cooled dimethylformamide (0.8 mL, 10.3 mmol). After stirring at room temperature for 30 minutes, the mixture was cooled to –5° C. and a solution of [3-(6,6-dimethyl-4,5,6,7-tetrahydro-1H-indol-3-yl)-propyl]-diethyl-amine (0.9 g, 3.4 mmol) in dimethylformamide (2 mL) was added dropwise. The mixture was stirred at room temperature for 3 hours. The reaction was quenched with ice, followed by 10 N potassium to adjust the pH to 10–11. After stirring at room temperature for 1 hour, the reaction was extracted with ethyl acetate and the extract was washed with brine, dried and concentrated to give 0.55 g of 3-(3-diethylamino-propyl)-6,6-dimethyl-4,5,6,7-tetrahydro-1H-indole-2-carbaldehyde. ¹H-NMR (360 MHz, dimethylsulfoxide-d6) δ 11.23 (br, s, 1H, NH), 9.41 (s, 1H, CHO), 2.61 (t, 2H, CH₂), 2.30–2.43 (m, 10 H, 5×CH₂), 1.58 (m, 2H, CH₂), 1.45 (t, 2H, CH₂), 0.93 (s, 6H, 2×CH₃), 0.89 (t, 6H, CH₃). MS m/z 290 [M+].

A-16 5-Formyl-2,4-dimethyl-1H-pyrrole-3-carboxylic acid (2-pyrrolidin-1-yl-ethyl)-amide 5-Formyl-2,4-dimethyl-1H-pyrrole-3-carboxylic acid (0.5 g, 2.99 mmol) was reacted with 1-(2-aminoethyl)pyrrolidine (0.42 mL) to give 0.57 g (73% yield) of 5-formyl-2,4-dimethyl-1H-pyrrole-3-carboxylic acid (2-pyrrolidin-1-yl-ethyl)-amide using General Amidation Procedure 1. ¹H-NMR (360 MHz, dimethylsulfoxide-d6) δ 11.79 (br s, 1H, NH), 9.53 (s, 1H, CHO), 7.41 (m, 1H, NH), 3.28–3.34 (m, 2H, CH₂), 2.53–2.60 (m, 6H, CH₂ and 2×CH₂), 2.35 (s, 3H, CH₃), 2.3 (s, 3H, CH₃), 1.68 (m, 4H, 2×CH₂). MS m/z 264 [M+1].

A-17 2-Ethyl-5-formyl-4-methyl-1H-pyrrole-3-carboxylic acid (2-pyrrolidin-1-yl-ethyl)-amide

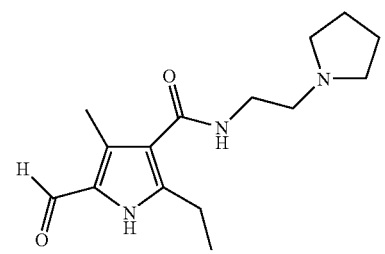

MS m/z 278 [M+1].

A-18 5-Formyl-2-methyl-4-[3-(4-methyl-piperazin-1-yl)-propyl]-1H-pyrrole-3-carboxylic acid ethyl ester

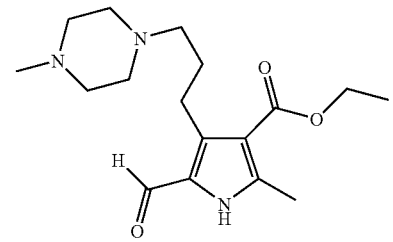

MS m/z 322 [M+1].

A-19 5-Formyl-2-methyl-4-(3-morpholin-4-yl-propyl)-1H-pyrrole-3-carboxylic acid ethyl ester

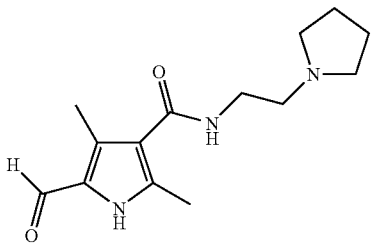

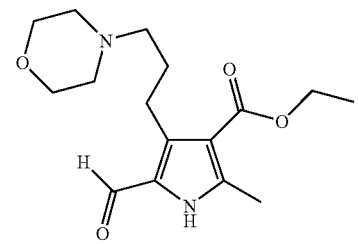

MS m/z 309 [M+1].

A-20 4-(3-Dimethylamino-propyl)-5-formyl-2-methyl-1H-pyrrole-3-carboxylic acid ethyl ester

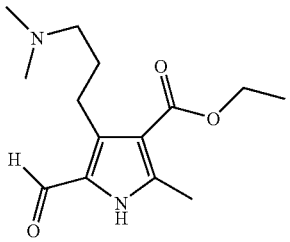

To a suspension of 4-(2-carboxy)ethyl-3-ethoxycarbonyl-2-methylpyrrole (2 g, 8.88 mmol) (Bulter, A. R., and George, S. D. (1993) Tetrahedron 49: 7017–7026) in 18 mL of dimethylformamide was added 1.73 g (10.65 mmol) of carbonyldiimidazole followed by the dropwise addition of 8.9 mL (17.76 mmol) of 2M dimethylamine in tetrahydrofuran. After stirring for 2 hours, the reaction was diluted with water (200 mL) and cooled. The precipitate was collected by vacuum filtration, washed with water and dried to give 1.0 g of the product as a white crystalline solid. The filtrate was extracted with ethyl acetate, the organic layer was washed with brine, dried and concentrated to give 0.9 g of the product. A total of 1.9 g (85% yield) of 4-(2-dimethylcarbamoyl-ethyl)-2-methyl-1H-pyrrole-3-carboxylic acid ethyl ester was obtained. $^1$H-NMR (360 MHz, dimethylsulfoxide-d6) δ 10.89 (br s, 1H, NH), 6.40 (d, 1H), 4.13 (q, 2H, OCH$_2$), 2.92 (s, 3H, NCH$_3$), 2.79 (s, 3H, NCH$_3$), 2.75 (m, 2H, CH$_2$), 2.45 (m, 2H, CH$_2$), 2.35 (s, 3H, CH$_3$), 1.23 (t, 3H, CH$_3$). MS m/z 252 [M+].

To a heterogeneous mixture of 4-(2-dimethylcarbamoyl-ethyl)-2-methyl-1H-pyrrole-3-carboxylic acid ethyl ester (1.01 g, 4 mmol) in tetrahydrofuran (9 mL) was added dropwise 8 mL of borane-tetrahydrofuran complex (1M solution in tetrahydrofuran). The mixture was heated to reflux overnight. Nine mL of methanol was added slowly to the reaction and the heating was continued for another 2 hours. The cooled reaction was quenched with 1 N hydrochloric acid and extracted with ethyl acetate. The aqueous layer was basified with aqueous potassium hydroxide, extracted with ethyl acetate, and the organic layer washed with brine, dried and concentrated to give 616 mg (65% yield) of 4-(3-dimethylamino-propyl)-2-methyl-1H-pyrrole-3-carboxylic acid ethyl ester as a faint orange oil. $^1$H-NMR (360 MHz, dimethylsulfoxide-d6) δ 10.84 (br s, 1H, NH), 6.36 (d, 1H), 4.12 (q, 2H, OCH$_2$), 2.52 (m, 2H, CH$_2$), 2.34 (s, 3H, CH$_3$), 2.17 (m, 2H, CH$_2$), 2.08 (s, 6H, N(CH$_3$)$_2$), 1.57 (m, 2H, CH$_2$), 1.23 (t, 3H, CH$_3$).

MS m/z 238 [M+].

4-(3-Dimethylamino-propyl)-2-methyl-1H-pyrrole-3-carboxylic acid ethyl ester (600 mg, 2.5 mmol) was formylated using phosphorus oxychloride and dimethylformamide to give 645 mg (96% yield) of 4-(3-dimethylamino-propyl)-5-formyl-2-methyl-1H-pyrrole-3-carboxylic acid ethyl ester. $^1$H-NMR (360 MHz, dimethylsulfoxide-d6) δ 12.15 (br s, 1H, NH), 9.59 (s, 1H, CHO), 4.19 (q, 2H, OCH$_2$), 2.93 (m, 2H, CH$_2$), 2.41 (s, 3H, CH$_3$), 2.18 (m, 2H, CH$_2$), 2.09 (s, 6H, N(CH$_3$)$_2$), 1.63 (m, 2H, CH$_2$), 1.27 (t, 3H, CH$_3$). MS m/z 266 [M+].

A-21 3-Methyl-5-(4-methyl-piperazine-1-carbonyl)-1H-pyrrole-2-carbaldehyde

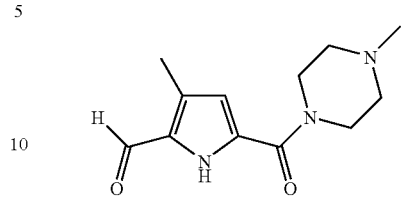

Dimethylformamide (3 mL, 6 equivalents) was cooled with stirring in an ice bath. To this was added phosphorus oxychloride (1.1 equivalents, 0.67 mL). After 30 minutes, a solution of 4-methyl-2-pyrrolecarboxylic acid ethyl ester (1 g, 6.53 mmol) in dimethylformamide (2M, 3 mL) was added to the reaction and stirring continued. After 1 hour, the reaction was warmed to room temperature. After another 2.5 hours, the reaction mixture was diluted with water (100 mL) and basified to pH 11 with 1 N sodium hydroxide solution. The precipitate was collected by vacuum filtration, washed with water and dried to afford 0.8 g (68% yield) 5-formyl-4-methyl-1H-pyrrole-2-carboxylic acid ethyl ester as a white solid. $^1$H-NMR (360 MHz, dimethylsulfoxide-d6) δ 12.6 (br s, 1H, NH), 9.78 (s, 1H, CHO), 6.68 (s, 1H, CH), 4.26 (q, 2H, OCH$_2$), 2.28 (s, 3H, CH$_3$), 1.28 (t, 3H, CH$_3$). MS m/z 181 [M+].

5-Formyl-4-methyl-1H-pyrrole-2-carboxylic acid ethyl ester was dissolved in water (35 mL) and ethanol (15 mL) with stirring. Potassium hydroxide (2 equivalents, 0.5 g) was added and the mixture heated to 100° C. After 1 hour the mixture was cooled to room temperature and concentrated to about ⅔ volume. The water layer was acidified to pH 3 using 2 N hydrochloric acid. The white solid was collected by vacuum filtration and washed with water to afford 0.67 g (68% yield) of 5-formyl-4-methyl-1H-pyrrole-2-carboxylic acid as a tan solid. $^1$H-NMR (360 MHz, dimethylsulfoxide-d6) δ 12.92 (br s, 1H, COOH), 12.48 (br s, 1H, NH), 9.76 (s, 1H, CHO), 6.63 (s, 1H, pyrrole CH), 2.28 (s, 3H, CH$_3$). MS m/z 152 [M+−1].

5-Formyl-4-methyl-1H-pyrrole-2-carboxylic acid was amidated with 1-methylpiperazine using General Amidation Procedure 1 to give 3-Methyl-5-(4-methyl-piperazine-1-carbonyl)-1H-pyrrole-2-carbaldehyde. MS m/z 236 [M+1].

A-22 5-(4-Methyl-piperazine-1-carbonyl)-1H-pyrrole-2-carbaldehyde

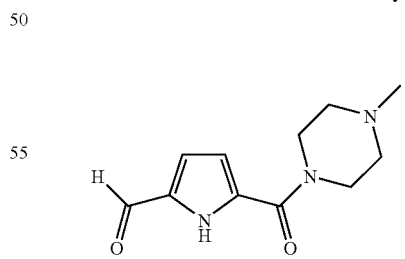

To a solution of dimethylformamide (21 mL, 0.27 mol) in 75 mL of dichloroethane was added a solution of phosphorus oxychloride (25 mL, 0.27 mol) in 75 mL of dichloroethane at 0° C. The mixture was stirred at room temperature for 30 minutes and cooled to 0° C. To the mixture was added a solution of ethyl pyrrole-2-carboxylate (25 g, 0.18 mol) in 50 mL of dichloroethane dropwise. The resulting mixture was stirred at room temperature for 30 minutes and then at 40° C. for 1 hour. The mixture was poured into ice and basified to pH 11 with 5 N sodium hydroxide solution. The mixture was extracted with ethyl acetate and the extract washed with water, brine and dried over anhydrous sodium sulfate. The two products were separated by column chromatography (1:3 ethyl acetate:hexane) to give 15 g (50% yield) of 5-formyl-1H-pyrrole-2-carboxylic acid ethyl ester and 2 g (7% yield) of 4-formyl-1H-pyrrole-2-carboxylic acid ethyl ester. $^1$H-NMR (5-formyl-1H-pyrrole-2-carboxylic acid ethyl ester) (300 MHz, dimethylsulfoxide) δ 13.02 (br s, 1H, NH), 9.69 (s, 1H, CHO), 6.95 (d, 1H), 6.86 (d, 1H), 4.27 (q, 2H, CH$_3$), 1.28 (t, 3H, CH$_3$). MS m/z 167 [M+].

Refluxing 4-formyl-1H-pyrrole-2-carboxylic acid ethyl ester in 2 equivalents of potassium hydroxide in methanol:water followed by acidification to pH 3 at 0° C. gave 4-formyl-1H-pyrrole-2-carboxylic acid as a solid. MS m/z 140 [M+1].

5-Formyl-4-methyl-1H-pyrrole-2-carboxylic acid was dissolved in dimethylformamide (0.3M) with stirring. To this was added 1-ethyl-3-(3-dimethylamino-propylcarbodiimide hydrochloride (1.2 equivalents), 1-hydroxybenzotriazole (1.2 equivalents) followed by triethylamine (2 equivalents) and 1-methylpiperazine (1 equivalent) and the reaction stirred for 12 hours (General Amidation Procedure 1). The reaction was diluted with saturated sodium bicarbonate solution, sodium hydroxide solution, brine, solid sodium chloride and extracted twice with 10% methanol in dichloromethane. The combined organic layers were washed with brine, dried over anhydrous magnesium sulfate and concentrated. The resulting oil was re-concentrated from toluene and precipitated from diethyl ether:hexanes to afford 5-(4-methyl-piperazine-1-carbonyl)-1H-pyrrole-2-carbaldehyde as a solid. MS m/z 222 [M+1].

A-23 3-(3-Pyrrolidin-1-yl-propyl)-4,5,6,7-tetrahydro-1H-indole-2-carbaldehyde

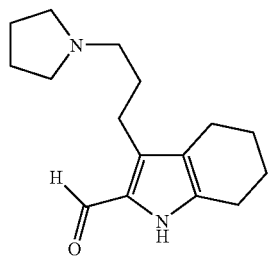

A mixture of 5-aminolevulinic acid hydrochloride (1 equivalent), 1,3-cyclohexanedione (1 equivalent) and sodium acetate (2 equivalents) in water (1M) was heated at 110° C. for 12 hours and then cooled. The resulting solid was collected by vacuum filtration, washed with 30% ethanol in water and dried under vacuum to give 3-(4-oxo-4,5,6,7,tetrahydro-1H-indol-3-yl-propionic acid in 60% yield. $^1$H-NMR (360 MHz, dimethylsulfoxide-d6) δ 11.91 (br s, 1H, COOH), 10.99 (br s, 1H, NH), 6.45 (d, 1H), 2.76 (t, 2H, CH$_2$), 2.69 (t, 2H, CH$_2$), 2.44 (t, 2H, CH$_2$), 2.26 (t, 2H, CH$_2$), 1.96 (m, 2H, CH$_2$). MS m/z 207 [M+].

To a suspension of 10 g of 3-(4-oxo-4,5,6,7,tetrahydro-1H-indol-3-yl-propionic acid (48 mmol) in 60 mL of dichloromethane was added 9.3 g (57.6 mmol) of carbonyldiimidazole. After stirring at room temperature for 2 hours, 12 mL (144 mmol) of pyrrolidine was added. The dark red reaction mixture was then stirred at room temperature overnight. The reaction was poured into water and the organic layer washed with brine, dried and concentrated to give 3-(3-oxo-3-pyrrolidin-1-yl-propyl)-1,5,6,7-tetrahydro-indol-4-one (12 g, 96% yield). $^1$H-NMR (300 MHz, dimethylsulfoxide-d6) δ 11.05 (br s, 1H, NH), 6.46 (d, 1H), 3.35 (m, 2H, CH$_2$), 2.24 (m, 2H, CH$_2$), 2.66–2.73 (m, 4H, 2×CH$_2$), 2.44 (m, 2H, CH$_2$), 2.26 (m, 2H, CH$_2$), 1.96 (m, 2H, CH$_2$), 1.82 (m, 2H, CH$_2$), 1.73 (m, 2H, CH$_2$). MS m/z 260 [M+].

To a suspension of 3-(3-oxo-3-pyrrolidin-1-yl-propyl)-1,5,6,7-tetrahydro-indol-4-one (5 g, 19.2 mmol) in tetrahydrofuran was added lithium aluminum hydride (2.9 g, 4 equivalents). The mixture was heated to reflux overnight and cooled to room temperature. To the reaction was added water (2.9 mL), 15% sodium hydroxide (2.9 mL) and water (2.9 ml). The mixture was stirred at room temperature for 30 minutes, filtered and the solids washed with ethyl acetate. The filtrate was concentrated to give 4.5 g (100% yield) of the product as a light yellow oil. $^1$H-NMR (300 MHz, dimethylsulfoxide-d6) δ 9.82 (br s, 1H, NH), 6.22 (s, 1H), 2.2–2.5 (m, 12H, 6×CH$_2$), 1.5–1.64 (m, 1OH, 5×CH$_2$). MS m/z 232 [M+].

Phosphorus oxychloride (2.0 mL, 21.2 mmol) was added dropwise to ice-cooled dimethylformamide (4.5 mL) and stirred at room temperature for 30 minutes. To the mixture at −5° C. was added a suspension of 3-(3-pyrrolidin-1-yl-propyl)-4,5,6,7-tetrahydro-1H-indole (4.5 g, 19.3 mmol) in 10 mL of dimethylformamide. The mixture was stirred at room temperature overnight. Ice cubes were added to the reaction followed by 10 N potassium hydroxide to pH 11–12. The mixture was stirred for 1 hour, extracted with ethyl acetate and the extract washed with brine and concentrated. The residue was dissolved in dichloromethane and filtered through silica gel eluting with 7% methanol in dichloromethane to give 3.8 g (76% yield) of the product. $^1$H-NMR (300 MHz, diemthylsulfoxide-d6) δ 11.28 (br, s, 1H, NH), 9.38 (s, 1H, CHO), 2.59 (t, 2H, CH$_2$), 2.46 (m, 2H, CH$_2$), 2.3–2.44 (m, 8H, 4×CH$_2$), 1.55–1.65 (m, 10H, 5×CH$_2$). MS m/z 260 [M+].

A-24 3-[3-(4-Methyl-piperazin-1-yl)-propyl]-4,5,6,7-tetrahydro-1H-indole-2-carbaldehyde

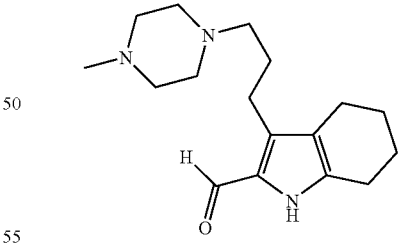

A mixture of 5-aminolevulinic acid hydrochloride (1 equivalent), 1,3-cyclohexanedione (1 equivalent) and sodium acetate (2 equivalents) in water (1M) was heated to at 110° C. for 12 hours and then cooled. The resulting solid was collected by vacuum filtration, washed with 30% ethanol in water and dried under vacuum to give 3-(4-oxo-4,5,6,7tetrahydro-1H-indol-3-yl-propionic acid in 60% yield. $^1$H-NMR (360 MHz, DMSO-d6) δ 11.91 (br s, 1H, COOH), 10.99 (br s, 1H, NH), 6.45 (d, 1H), 2.76 (t, 2H, CH$_2$), 2.69 (t, 2H, CH$_2$), 2.44 (t, 2H, CH$_2$), 2.26 (t, 2H, CH$_2$), 1.96 (m, 2H, CH$_2$). MS m/z 207 [M+].

To a suspension of 10 g of 3-(4-oxo-4,5,6,7,tetrahydro-1H-indol-3-yl-propionic acid (48 mmol) in 60 mL of dichloromethane was added 9.3 g (57.6 mmol) of carbonyldiimidazole. After stirring at room temperature for 2 hours, 5.3 mL (48 mmol) of 1-methylpiperazine and 8.4 mL (48 mmol) of N,N-diisopropylethylamine were added. The dark red reaction mixture was stirred at room temperature overnight. The reaction was poured into water and the organic layer washed with brine, dried and concentrated to give 8 g (57% yield) of 3-[3-(4-methyl-piperazin-1-yl)-3-oxo-propyl]-1,5,6,7-tetrahydro-indol-4-one. $^1$H-NMR (360 MHz, dimethylsulfoxide-d6) δ 10.97 (br s, 1H, NH), 6.47 (d, 1H), 3.43 (m, 4H, 2×CH$_2$), 2.67–2.75 (m, 4H, 2×CH$_2$), 2.51 (m, 2H, CH$_2$), 2.27 (m, 2H, CH$_2$), 2.20 (m, 4H, 2×CH$_2$), 2.15 (s, 3H, CH$_3$), 1.97 (m, 2H, CH$_2$). MS m/z 289 [M+].

To a suspension of 3-[3-(4-methyl-piperazin-1-yl)-3-oxo-propyl]-1,5,6,7-tetrahydro-indol-4-one (5 g, 17 mmol) in 300 mL of tetrahydrofuran was added dropwise a solution of lithium aluminum hydride in tetrahydrofuran (2.6 g, 68 mmol). The mixture was heated to reflux overnight. To the cooled reaction was sequentially added 2.6 mL each of water, 15% sodium hydroxide and water. The reaction was stirred at room temperature for 30 minutes and the insolubles removed by vacuum filtration. The filtrate was concentrated to give 4.5 g (100% yield) of 3-[3-(4-methyl-piperazin-1-yl)-propyl]-4,5,6,7-tetrahydro-1H-indole. $^1$H-NMR (360 MHz, dimethylsulfoxide-d6) δ 9.79 (br s, 1H, NH), 6.22 (d, 1H), 2.44 (m, 2H, CH$_2$), 2.21–2.30 (m, 14H, 7×CH$_2$), 2.12 (s, 3H, CH$_3$), 1.65 (m, 4H, 2×CH$^2$), 1.53 (m, 2H, CH$_2$). MS m/z 261 [M+].

Phosphorus oxychloride (1.8 mL, 18.9 mmol) was added dropwise to cooled dimethylformamide (3.8 mL, 51.6 mmol). After stirring at room temperature for 30 minutes, it was cooled to −5° C. and a solution of 3-[3-(4-methyl-piperazin-1-yl)-propyl]-4,5,6,7-tetrahydro-1H-indole (4.5 g, 17.2 mmol) in dimethylformamide (9 mL) was added dropwise. The mixture was stirred at room temperature overnight. The reaction was quenched with ice, followed by 10 N sodium hydroxide to pH 10–11. After stirring at room temperature for 1 hour, the reaction was extracted with ethyl acetate, washed with brine, dried and concentrated to give 3.1 g (62% yield) of 3-[3-(4-methyl-piperazin-1-yl)-propyl]-4,5,6,7-tetrahydro-1H-indole-2-carbaldehyde. $^1$H-NMR (360 MHz, diemthylsulfoxide-d6) δ 11.24 (br, s, 1H, NH), 9.42 (s, 1H, CHO), 2.60 (t, 2H, CH$_2$), 2.51 (m, 2H, CH$_2$), 2.35 (m, 2H, CH$_2$), 2.28 (m, 8H, 4×CH$_2$), 2.21 (m, 2H, CH$_2$), 2.12 (s, 3H, CH$_3$), 1.57–1.68 (m, 6H, 3×CH$_2$). MS m/z 289 [M+].

A-25 3-(3-Morpholin-4-yl-propyl)-4,5,6,7-tetrahydro-1H-indole-2-carbaldehyde

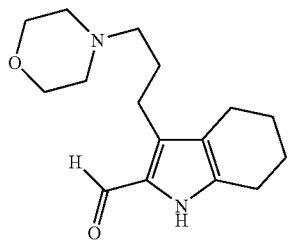

To a suspension of 1.9 g (50 mmol) of lithium aluminum hydride in 30 mL of tetrahydrofuran was added dropwise a solution of 11.3 g (43 mmol) of 1-morpholin-4-yl-3-(4,5,6,7-tetrahydro-1H-indol-3-yl)-propan-1-one in 20 mL of tetrahydrofuran. The reaction mixture was stirred at 80° C. for 2.5 hours and then cooled in an ice bath. Ice cubes were slowly added to the reaction mixture until no more gas was generated. A few drops of 2 N sodium hydroxide were added and the reaction mixture was stirred at room temperature for 30 minutes, extracted with ethyl acetate and the extract dried over anhydrous sodium sulfate and concentrated to give 9.2 g (89% yield) of 3-(3-morpholin-4-yl-propyl)-4,5,6,7-tetrahydro-1H-indole as a red oil which was used without further purification.

To an ice-cooled solution of 0.32 mL (4.1 mmol) of dimethylformamide in 3 mL of dichloromethane was added dropwise 0.4 mL (4.1 mmol) of phosphorus oxychloride. The reaction mixture was stirred at room temperature for 15 minutes and a solution of 680 mg (2.7 mmol) of 3-(3-morpholin-4-yl-propyl)-4,5,6,7-tetrahydro-1H-indole in 20 mL of dichloromethane was added dropwise at 0° C. The mixture was refluxed at 60° C. for 4 hours and cooled in an ice bath. Ice cubes were slowly added to the mixture followed by addition of 2 N sodium hydroxide to pH 12. The mixture was stirred at room temperature for 30 minutes and extracted with ethyl acetate. The organic layer was washed with brine, dried over anhydrous sodium sulfate and concentrated to give crude product which was purified on a silica gel column eluting with dichloromethane-methanol-ammonium hydroxide (98:2:1) to give 600 mg (83% yield) of 3-(3-morpholin-4-yl-propyl)-4,5,6,7-tetrahydro-1H-indole-2-carbaldehyde as a dark red oil. $^1$H-NMR (360 MHz, dimethylsulfoxide-d6) δ 11.33 (s, br, 1H, NH). MS m/z 277 [M+1].

A-26 6,6-Dimethyl-3-(3-morpholin-4-yl-propyl)-4,5,6,7-tetrahydro-1H-indole-2-carbaldehyde

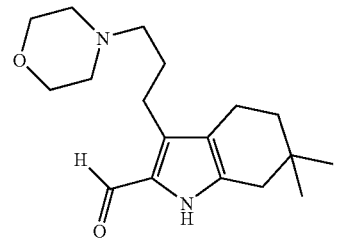

To a suspension of 1.65 g (7 mmol) of 3-(4-oxo-4,5,6,7-6,6-dimethyl-tetrahydro-1H-indol-3-yl-propionic acid) in 25 mL of dichloromethane was added 1.36 g (8.4 mmol) of carbonyldiimidazole. After stirring at room temperature for 2 hours, 0.6 mL (7 mmol) of morpholine and 1.2 mL (7 mmol) of N,N-diisopropylethylamine were added. The dark red reaction mixture was stirred at room temperature overnight. The reaction was poured into water and the organic layer washed with brine, dried and concentrated to give 1.9 g of 6,6-dimethyl-3-(3-morpholin-4-yl-3-oxo-propyl)-1,5,6,7-tetrahydro-indol-4-one as a white solid. $^1$H-NMR (360 MHz, dimethylsulfoxide-d6) δ 10.94 (br s, 1H, NH), 6.49 (s, 1H), 3.42–3.50 (m, 8H, 4×CH$_2$), 2.74 (m, 2H, CH$_2$), 2.57 (s, 2H, CH$_2$), 2.48 (m, 2H, CH$_2$), 2.17 (s, 2H, CH$_2$), 1.00 (s, 6H, 2×CH$_3$). MS m/z 304 [M+].

To a suspension of 1.1 g (30 mmol) of lithium aluminum hydride in 10 mL of tetrahydrofuran was added dropwise a solution of 1.8 g (43 mmol) of 6,6-dimethyl-3-(3-morpholin- 4-yl-3-oxo-propyl)-1,5,6,7-tetrahydro-indol-4-one in 10 mL of tetrahydrofuran. The mixture was stirred at 80° C. for 2.5 hours and then cooled in an ice bath. Ice cubes were added to the reaction mixture slowly until no more gas was generated. A few drops of 2 N sodium hydroxide were added and the reaction mixture was stirred at room temperature for 30 minutes, extracted with ethyl acetate, and the extract dried over anhydrous sodium sulfate and concentrated to give 1.6 g of 6,6-dimethyl-3-(3-morpholin-4-yl-propyl)-4,5,6,7-tetrahydro-1H-indole as a white solid which was used without further purification. $^1$H-NMR (360 MHz, dimethylsulfoxide-d6) δ 9.75 (br s, 1H, NH), 6.24 (s, 1H), 3.54 (m, 4H, 2×CH$_2$), 2.23–2.31 (m, 12H, 6×CH$_2$), 1.58 (m, 2H, CH$_2$), 1.40 (m, 2H, CH$_2$), 0.92 (s, 6H, 2×CH$_3$). MS m/z 276 [M+].

6,6-Dimethyl-3-(3-morpholin-4-yl-propyl)-4,5,6,7-tetrahydro-1H-indole was formylated and recrystallized from 20% ethyl acetate in hexane to give 0.5 g of 6,6-dimethyl-3-(3-morpholin-4-yl-propyl)-4,5,6,7-tetrahydro-1H-indole-2-carbaldehyde as a light yellow solid. $^1$H-NMR (360 MHz, dimethylsulfoxide-d6) δ 11.25 (br, s, 1H, NH), 9.43 (s, 1H, CHO), 3.54 (m, 4H, 2×CH$_2$), 2.63 (t, 2H, CH$_2$), 2.20–2.37 (m, 10 H, 5×CH$_2$), 1.62 (m, 2H, CH$_2$), 1.45 (t, 2H, CH$_2$), 0.93 (s, 6H, 2×CH$_3$). MS m/z 304 [M+].

A-27 3,5-Dimethyl-4-(morpholine-4-carbonyl)-1H-pyrrole-2-carbaldehyde

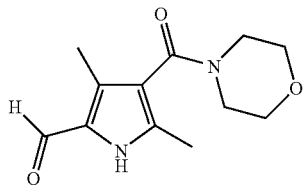

MS m/z 236 [M+1].

A-28 3,5-Dimethyl-4-[4-(4-methyl-piperazine-1-carbonyl)-phenyl]-1H-pyrrole-2-carbaldehyde

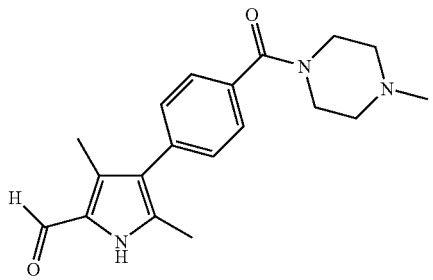

3,5-Dimethyl-1H-pyrrole-2-carboxylic acid ethyl ester (204 g), 177 g of potassium carbonate and 1428 mL of acetonitrile were stirred and cooled to 4° C. in an ice bath. N-Bromosuccinimide (228 g) was added in portions with vigorous stirring keeping the temperature below 17° C. The mixture was warmed to 20° C. and 2856 mL of water was slowly added. The mixture was stirred for 30 minutes. The precipitate was collected by vacuum filtration and washed three times with 400 mL of ethanol:water 1:2 each time. The solids were dried under vacuum at 60° C. to give 228 g (76% yield) of 4-bromo-3,5-dimethyl-1H-pyrrole-2-carboxylic acid ethyl ester as an off-white solid. $^1$H-NMR (dimethylsulfoxide-d6) δ 1.26 (t, 3H, CH$_3$), 2.14, 2.17 (2×s, 2×3H, 2×CH$_3$), 4.20 (d, 2H, CH$_2$O), 11.75 (br s, 1H, NH). MS m/z 246, 248 [M+1].

4-Bromo-3,5-dimethyl-1H-pyrrole-2-carboxylic acid ethyl ester (16.5 g), 12.5 g of 4-carboxyphenylboronic acid, 2.6 g of tetrakis(triphenylphosphine)palladium(0), 33.4 g of potassium carbonate, 169 mL of dimethylformamide and 85 mL of water were purged with nitrogen and refluxed for 18 hours at 110–112° C. A black and gray precipitate replaced the original yellow-brown solid catalyst. The mixture was cooled to room temperature and decanted, leaving black and gray solids on the walls of the flask. The mixture was vacuum filtered to remove remaining black and gray precipitate and the solids washed with 10 mL of ethanol:water 1:1. Water (1000 mL) and 15 mL of 9 N potassium hydroxide were slowly added to the combined filtrates to give a gray precipitate which was collected and discarded. The filtrate was cooled in an ice bath and acidified to pH 2.5 with 10 N hydrochloric acid and then diluted with 500 mL of water. The solids were collected by vacuum filtration, washed three times with 20 mL of water each time, and dried under vacuum at 60° C. to give 13.6 g (69% yield) of 4-(4-carboxy-phenyl)-3,5-dimethyl-1H-pyrrole-2-carboxylic acid ethyl ester as a light pink solid. $^1$H-NMR (dimethylsulfoxide-d6) δ 1.28 (t, 3H, CH$_3$), 2.20, 2.22 (2×s, 2×3H, 2×CH$_3$), 4.21 (d, 2H, CH$_2$O), 7.34, 7.93 (multiplets, 4H, aromatic), 11.63 (br s, 1H, NH), 12.80 (br s, 1H, COOH). MS m/z 288 [M+1].

4-(4-Carboxy-phenyl)-3,5-dimethyl-1H-pyrrole-2-carboxylic acid ethyl ester (11.8 g), 11.8 mL of ethylene glycol, 36 mL of water and 13.6 mL of 9 N potassium hydroxide were refluxed at 105° C. for 25 minutes. Thin layer chromatography (ethyl acetate:hexane:acetic acid 4:6:0.5) showed conversion of all starting material at Rf 0.5 to a new product at Rf 0.3. The mixture was cooled to 98° C. and 13 mL of 10 N hydrochloric acid was added to a pH of 2.0 accompanied by rapid release of carbon dioxide gas. The maximum temperature reached was 103° C. which dropped to 95° C. by the end of the gas evolution. The mixture was cooled in an ice bath and vigorously stirred for 30 minutes. The solids were collected by vacuum filtration and washed three times with 20 mL of water each time to give 8.7 g (99% yield) of 4-(2,4-dimethyl-1H-pyrrol-3-yl)-benzoic acid as a light purple solid. $^1$H-NMR (dimethylsulfoxide-d6) δ 2.00, 2.18 (2×s, 2×3H, 2×CH$_3$), 6.46 (s, 1H, pyrrole CH), 7.34, 7.90 (multiplets, 4H, aromatic), 10.49 (br s, 1H, NH), 12.70 (br s, 1H, COOH). MS m/z 216 [M+1].

Dimethylformamide (7.5 g) and 45 mL of dichloromethane were cooled to 6° C. and 7.3 mL of phosphorus oxychloride were added with stirring. 4-(2,4-Dimethyl-1H-pyrrol-3-yl)-benzoic acid (11.1 g) was slowly added. The mixture was refluxed for 30 minutes. Thin layer chromatography (ethyl acetate:hexane:acetic acid 4:6:0.5) showed no starting material at Rf 0.5 and a new spot at the origin. The mixture was cooled to 5° C. and 50 mL of ice water were added. Potassium hydroxide (9 N, 60 mL total) was slowly added with cooling. The final pH was 12–13. The maximum temperature reached was 48° C. Water (100 mL) was added along with 15 mL of dichloromethane, some of which had boiled off. The aqueous phase was isolated at a temperature of about 35° C. to prevent precipitation. The aqueous phase was adjusted to pH 3 by slow addition of about 21 mL of 10 N hydrochloric acid with stirring and cooling in an ice bath. The solids were collected by vacuum filtration and washed 3 times with 15 mL of water each time to give 5.6 g (50% yield) of 4-(5-formyl-2,4-dimethyl-1H-pyrrol-3-yl)-benzoic acid as a tan solid. $^1$H-NMR (dimethylsulfoxide-d6) δ 2.23, 2.27 (2×s, 2×3H, 2×CH$_3$), 7.40, 7.95 (multiplets, 4H, aromatic), 9.56 (s, 1H, CHO), 11.85 (br s, 1H, NH), 12.90 (br s, 1H, COOH). MS m/z 244 [M+1].

4-(5-Formyl-2,4-dimethyl-1H-pyrrol-3-yl)-benzoic acid was reacted with 1-methylpiperazine using General Amidation Procedure 1 to give 3,5-dimethyl-4-[4-(4-methyl-piperazine-1-carbonyl)-phenyl]-1H-pyrrole-2-carbaldehyde. MS m/z 326 [M+1].

A-29 3,5-Dimethyl-4-[3-(morpholine-4-carbonyl)-phenyl]-1H-pyrrole-2-carbaldehyde

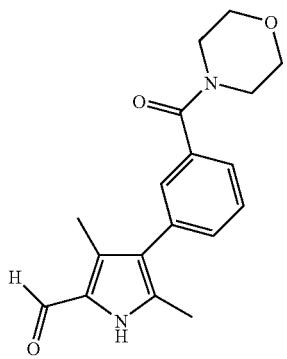

3,5-Dimethyl-1H-pyrrole-2-carboxylic acid ethyl ester (204 g), 177 g of potassium carbonate and 1428 mL of acetonitrile were stirred and cooled to 4° C. in an ice bath. N-Bromosuccinimide (228 g) was added in portions with vigorous stirring keeping the temperature under 17° C. The mixture was warmed to 20° C. and 2856 mL of water was slowly added. The precipitate was collected by vacuum filtration and washed three times with 400 mL of ethanol:water 1:2 each time. The solids were dried under vacuum at 60° C. to give 228 g (76% yield) of 4-bromo-3,5-dimethyl-1H-pyrrole-2-carboxylic acid ethyl ester as an off-white solid. $^1$H-NMR (dimethylsulfoxide-d6) δ 1.26 (t, 3H, CH$_3$), 2.14, 2.17 (2×s, 2×3H, 2×CH$_3$), 4.20 (d, 2H, CH$_2$O), 11.75 (br s, 1H, NH). MS m/z 246, 248 [M+1].

4-Bromo-3,5-dimethyl-1H-pyrrole-2-carboxylic acid ethyl ester (23.6 g), 17.5 g of 3-carboxyphenylboronic acid, 3.6 g of tetrakis(triphenylphosphine)palladium(0), 47.1 g of potassium carbonate, 190 mL of dimethylformamide and 95 mL of water were purged with nitrogen and refluxed for 4.5 hours at 110–112° C. A black and gray precipitate replaced the original yellow-brown solid catalyst. Thin layer chromatography (ethyl acetate:hexane:acetic acid 4:6:0.5) showed a trace of starting material at Rf 0.8, the presence of product at Rf 0.6 and minor spots at Rf 0.7 and Rf 0.5. The mixture was cooled to room temperature and vacuum filtered to removed the black and gray precipitate. The filter cake was washed with 20 mL of ethanol:water 1:1. Water (1140 mL) and 20 mL of 9 N potassium hydroxide were slowly added to the combined filtrates to give a gray precipitate which was collected and washed twice with 20 mL of ethanol:water 1:1. The filtrate was cooled in an ice bath and acidified to pH 2.5 with about 85 mL of 10 N hydrochloric acid. The solids were collected by vacuum filtration, washed three times with 30 mL of water each time, and dried under vacuum at 60° C. to give 18.8 g (68% yield) of crude 4-(3-carboxy-phenyl)-3,5-dimethyl-1H-pyrrole-2-carboxylic acid ethyl ester as a light pink solid. The crude was recrystallized three times from approximately 12 mL of ethanol per gram each time to give 11.7 g (62% yield for the recrystallization) of 4-(3-carboxy-phenyl)-3,5-dimethyl-1H-pyrrole-2-carboxylic acid ethyl ester as an off-white solid. $^1$H-NMR (dimethylsulfoxide-d6) δ 1.28 (t, 3H, CH$_3$), 2.17, 2.20 (2×s, 2×3H, 2×CH$_3$), 4.21 (d, 2H, CH$_2$O), 7.45, 7.75 (multiplets, 4H, aromatic), 11.46 (br s, 1H, NH), 12.93 (br s, 1H, COOH). MS m/z 288 [M+1].

4-(3-Carboxy-phenyl)-3,5-dimethyl-1H-pyrrole-2-carboxylic acid ethyl ester (15.0 g), 15 mL of ethylene glycol, 45 mL of water and 17.4 mL of 9 N potassium hydroxide were refluxed at 105° C. for 30 minutes. Thin layer chromatography (ethyl acetate:hexane:acetic acid 4:6:0.5) showed conversion of all starting material at Rf 0.5 to a new product at Rf 0.3. The mixture was cooled 100° C. and 21 mL of 10 N hydrochloric acid were added to a pH of 2.5 accompanied by rapid release of carbon dioxide gas. The mixture was cooled to ambient temperature and vigorously stirred for 30 minutes. The solids were collected by vacuum filtration and washed three times with 20 mL of water each time to give 10.9 g (97% yield) of 3-(2,4-dimethyl-1H-pyrrol-3-yl)-benzoic acid as a light purple solid. $^1$H-NMR (dimethylsulfoxide-d6) δ 2.08, 2.16 (2×s, 2×3H, 2×CH$_3$), 6.45 (s, 1H, pyrrole CH), 7.46, 7.75 (multiplets, 4H, aromatic), 10.42 (br s, 1H, NH), 12.81 (br s, 1H, COOH). MS m/z 216 [M+1].

Dimethylformamide (7.5 mL) and 55 mL of dichloromethane were cooled to 3° C. and 7.2 mL of phosphorus oxychloride were added with stirring. 4-(2,4-Dimethyl-1H-pyrrol-3-yl)-benzoic acid (10.9 g) was slowly added. The mixture was refluxed for 30 minutes. Thin layer chromatography (ethyl acetate:hexane:acetic acid 4:6:0.5) showed no starting material at Rf 0.6 and a new spot at the origin. The mixture was cooled to 5° C. and 55 mL of ice water were added. Potassium hydroxide (9 N, 50 mL total) was slowly added with cooling. The final pH was 12–13. The maximum temperature reached was 48° C. Water (100 mL) was added along with 15 mL of dichloromethane to replace that which had boiled off. The aqueous phase was isolated at a temperature of about 35° C. The aqueous phase was adjusted to pH 3 by slow addition of about 21 mL of 10 N hydrochloric acid with stirring and cooling in an ice bath. The solids were collected by vacuum filtration and washed 3 times with 15 mL of water each time to give 6.1 g (50% yield) of 3-(5-formyl-2,4-dimethyl-1H-pyrrol-3-yl)-benzoic acid as a reddish solid. $^1$H-NMR (dimethylsulfoxide-d6) δ 2.20, 2.24 (2×s, 2×3H, 2×CH$_3$), 7.53, 7.78, 7.85 (multiplets, 4H, aromatic), 9.55 (s, 1H, CHO), 11.85 (br s, 2H, and COOH). MS m/z 244 [M+1].

3-(5-Formyl-2,4-dimethyl-1H-pyrrol-3-yl)-benzoic acid was reacted with morpholine using General Amidation Procedure 1 to give 3,5-dimethyl-4-[3-(morpholine-4-carbonyl)-phenyl]-1H-pyrrole-carbaldehyde. MS m/z 326 [M+1].

A-30 4-(4-Hydroxy-piperidin-1-ylmethyl)-3,5-dimethyl-1H-pyrrole-2-carbaldehyde

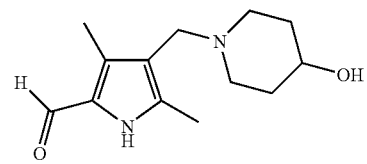

MS m/z 237 [M+1].

A-31 3,5-Diethyl-4-morpholin-4-ylmethyl-1H-pyrrole-2-carbaldehyde

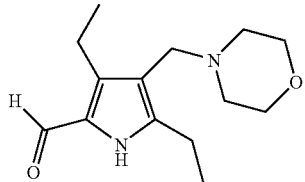

MS m/z 251 [M+1].

A-32 3,5-Dimethyl-4-[4-(morpholine-4-carbonyl)-phenyl]-1H-pyrrole-2-carbaldehyde

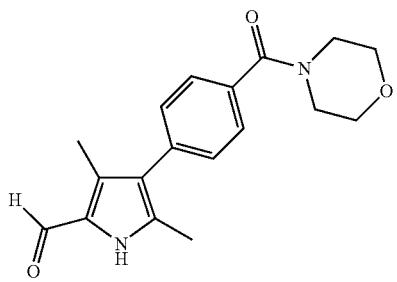

4-(5-Formyl-2,4-dimethyl-1H-pyrrol-3-yl)-benzoic acid was reacted with morpholine using General Amidation Procedure 1 to give 3,5-dimethyl-4-[4-(morpholine-4-carbonyl)-phenyl]-1H-pyrrole-2-carbaldehyde. MS m/z 313 [M+1].

A-33 3,5-Dimethyl-4-[3-(4-methyl-piperazine-1-carbonyl)-phenyl]-1H-pyrrole-2-carbaldehyde

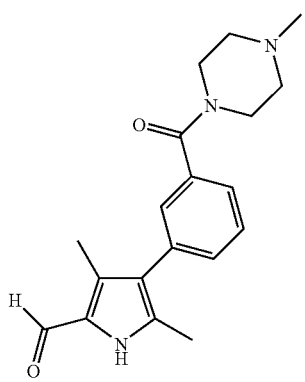

3-(5-Formyl-2,4-dimethyl-1H-pyrrol-3-yl)-benzoic acid was reacted with 1-methylpiperazine using General Amidation Procedure 1 to give 3,5-dimethyl-4-[3-(4-methyl-piperazine-1-carbonyl)-phenyl]-1H-pyrrole-2-carbaldehyde. MS m/z 326 [M+1].

A-34 3-Nitro-1H-pyrrole-2-carbaldehyde

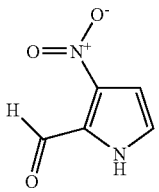

MS m/z 141 [M+1].

A-35 4-Nitro-1H-pyrrole-2-carbaldehyde

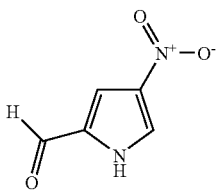

MS m/z 141 [M+1].

2. Oxindoles

Oxindoles can be prepared based on known literature method.

O-1 5-(6-Chloro-2,3-dihydro-indole-1-sulfonyl)-1,3-dihydro-indol-2-one

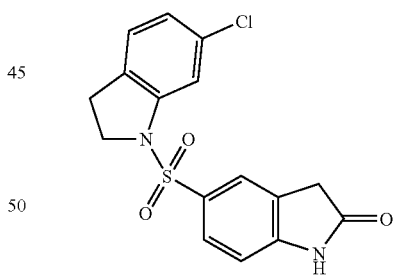

6-Chloroindole (1 g, 6.6 mmol) in glacial acetic acid (10 mL) was treated with sodium cyanoborohydride (829 mg, 13.2 mmol) portionwise at room temperature with stirring. After 1 hour, the reaction was diluted with water (25 mL) and basified with 40% sodium hydroxide with cooling. The mixture was then extracted with dichloromethane (3×50 mL), dried and concentrated to give 1 g of 6-chloroindoline. It was used in the next step without further purification. $^1$HNMR (300 MHz, dimethylsulfoxide-d6) δ 6.95 (d, 1H), 6.46 (dd, 1H), 6.43 (d, 1H), 5.74 (br s, 1H, NH), 3.42 (t, 2H, CH$_2$), 2.85 (t, 2H, CH$_2$). MS m/z 349 [M+1].

O-2 5-(5-Fluoro-2,3-dihydro-indole-1-sulfonyl)-1,3-dihydro-indol-2-one

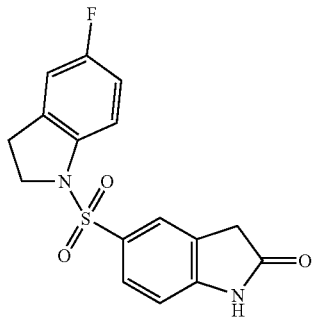

5-Fluoroindole (3 g, 22.2 mmol) in glacial acetic acid (35 mL) was treated with sodium cyanoborohydride (2.79 mg, 44.4 mmol) portionwise at room temperature with stirring. After one hour, the reaction was diluted with water and basified with 40% sodium hydroxide with cooling. The mixture was extracted 3 times with dichloromethane, dried and concentrated to give 5-fluoroindoline. It was used in the next step without further purification. $^1$H-NMR (300 MHz, dimethylsulfoxide-d6) δ 6.86 (m, 1H), 6.68 (dt, 1H), 6.42 (dd, 1H), 5.32 (br s, 1H, NH), 3.38 (m, 2H, CH$_2$), 2.87 (t, 2H, CH$_2$).

A mixture of 5-fluoroindoline from above, 5-chlorosulfonyl-2-oxindole (6.1 g, 1.2 equivalent) and pyridine (7.1 mL) in dichloromethane (40 mL) was stirred at room temperature overnight. The reaction was concentrated and the residue was recrystallized from methanol to give 5 g (68% yield) of 5-(5-fluoro-2,3-dihydro-indole-1-sulfonyl)-1,3-dihydro-indol-2-one as a pink-colored solid. $^1$H-NMR (360 MHz, dimethylsulfoxide-d6) δ 10.75 (br s, 1H, NH), 7.60 (m, 2H), 7.60 (dd, 1H), 7.02 (m, 2H), 6.90 (d, 1H), 3.89 (t, 2H, CH$_2$), 3.52 (s, 2H, CH$_2$), 2.87 (t, 2H, CH$_2$). MS 331 [M+−1].

O-3 5-(3,4-Dihydro-1H-isoquinoline-2-sulfonyl)-1,3-dihydro-indol-2-one

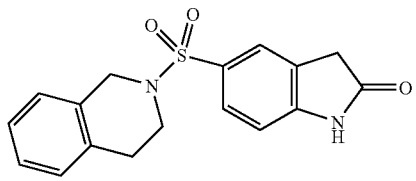

MS m/z 329 [M+1].

O-4 5-(5-Bromo-2,3-dihydro-indole-1-sulfonyl)-1,3-dihydro-indol-2-one

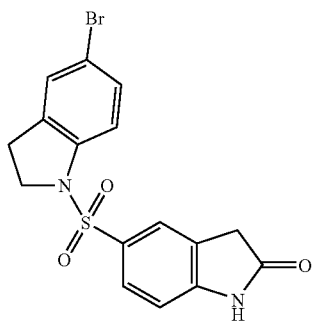

MS m/z 393 [M+1].

O-5 5-(3,4-Dihydro-2H-quinoline-1-sulfonyl)-1,3-dihydro-indol-2-one

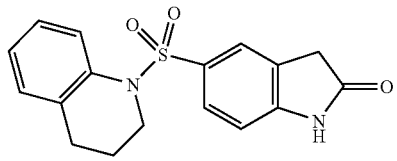

A mixture of 1,2,3,4-tetrahydroquinoline (Aldrich), 5-chlorosulfonyl-2-oxindole and pyridine in dichloromethane was stirred at room temperature overnight. The reaction was concentrated and the residue recrystallized from methanol to vie 5-(3,4,-dihydro-2H-quinoline-1-sulfonyl)-1,3-dihydro-indol-2-one. $^1$H-NMR (360 MHz, dimethylsulfoxide-d6) δ 10.74 (s, 1H, NH), 7.84–7.90 (d, 1H, SO2NH), 7.67–7.72 (m, 2H, 2×CH), 7.01–7.16 (m, 4H, aromatic), 6.95–6.97(d, 1H, CH), 4.28–4.29 (m, 1H), 3.58 (s, 2H, CH$_2$), 2.59–2.65 (m, 2H), 1.75–1.77 (m, 2H), 1.53–1.61 (m, 2H). MS m/z 329 [M+1].

O-6 5-(2,3-Dihydro-indole-1-sulfonyl)-1,3-dihydro-indol-2-one

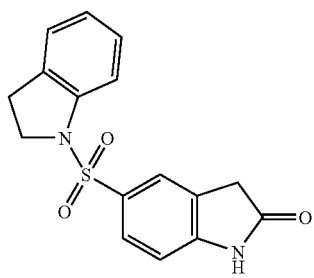

To a mixture of 5-chlorosulfonyl-2-oxindole (5 g, 21.6 mmol) and indoline (2.9 mL, 26 mmol) in tetrahydrofuran (20 mL) was added pyridine (3.4 g, 43 mmol). After stirring at room temperature for 1 day the precipitate was collected by vacuum filtration, washed with water in ethanol (20%), dried, washed with 60 mL of hot ethanol and dried under vacuum to give 7.5 g of 5-(2,3-dihydro-indole-1-sulfonyl)-1,3-dihydro-indol-2-one as a pink solid. $^1$H-NMR (360 MHz, dimethylsulfoxide-d6) δ 10.76 (br s, 1H, NH), 7.62 (m, 2H), 7.43 (d, 1H), 7.13–7.18 (m, 2H), 6.95 (dt, 1H), 6.90 (d, 1H), 3.87 (t, 2H, CH$_2$), 3.51 (s, 2H, CH$_2$), 2.91 (t, 2H, CH$_2$). MS m/z 315 [M+1].

O-7 5-(5-Methoxy-2,3-dihydro-indole-1-sulfonyl)-1,3-dihydro-indol-2-one

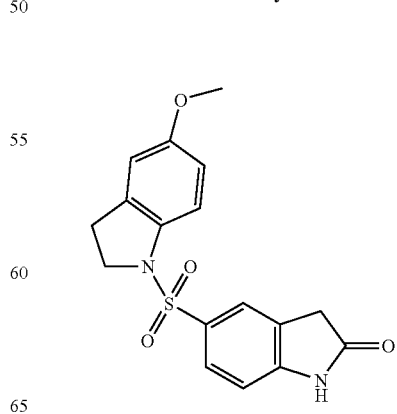

MS m/z 345 [M+1].

O-8 5-(4-Chloro-2,3-dihydro-indole-1-sulfonyl)-1,3-dihydro-indol-2-one

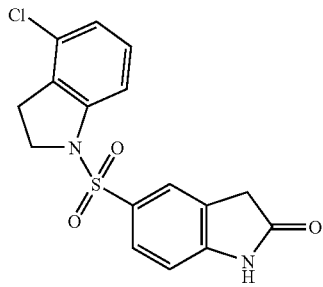

MS m/z 337 [M+1].

O-9 2-Oxo-2,3-dihydro-1H-indole-5-sulfonic acid (4-chloro-2-fluoro-phenyl)-amide

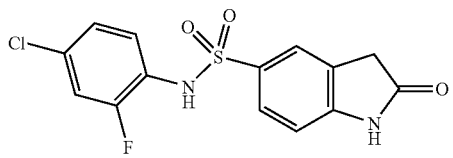

To a mixture of 5-chlorosulfonyl-2-oxindoel (5 g, 21.6 mmol) and 4-chloro-2-fluoroaniline (2.9 mL, 26 mmol) in tetrahydrofuran (30 mL) was added pyridine (3.4 g, 43 mmol). The mixture was stirred at room temperature for 1 day. The precipitate was collected by vacuum filtration, washed with water in methanol (20%), dried, washed with 60 mL of hot ethanol and dried to give 6.3 g (85%) of 2-oxo-2,3-dihydro-1H-indole-5-sulfonic acid (4-chloro-2-fluoro-phenyl)-amide as a light pink-colored solid. $^1$H-NMR (300 MHz, dimethylsulfoxide-d6) δ 10.79 (br s, 1H, NH), 10.12 (br s, 1H, NH), 7.54 (m, 2H), 7.39 (dd, 1H), 7.17–7.27 (m, 2H), 6.90 (d, 1H), 3.54 (s, 2H, CH$_2$). MS m/z 340 [M+].

O-10 2-Oxo-2,3-dihydro-1H-indole-5-sulfonic acid amide

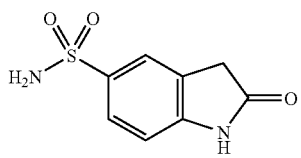

To a 100 mL flask charged with 27 mL of chlorosulfonic acid was added slowly 13.3 g of 2-oxindole. The reaction temperature was maintained below 30° C. during the addition. After the addition the reaction mixture was stirred at room temperature for 1.5 hour, heated to 68° C. for 1 hour, cooled, and poured into water. The precipitate was washed with water and dried in a vacuum oven to give 11.0 g (50% yield) of 5-chlorosulfonyl-2-oxindole which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of 5-aminosulfonyl-2-oxindole as an off-white solid. $^1$H-NMR (360 MHz, dimethylsulfoxide-d6) δ 10.67 (s, 1H, NH), 7.63–7.66 (m, 2H), 7.13 (s, 2H, 5-SO$_2$NH$_2$), 6.91 (d, 1H), 3.56 (s, 2H, CH$_2$). MS m/z 211 [M–1]+.

O-11 2-Oxo-2,3-dihydro-1H-indole-5-sulfonic acid methylamide

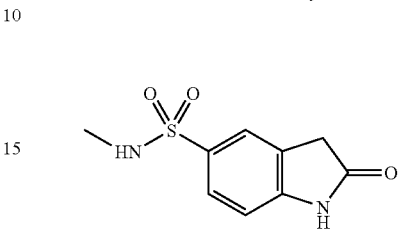

A suspension of 3.38 g of 5-chlorosulfonyl-2-oxindole in 10 mL of 2M methylamine in tetrahydrofuran was stirred at room temperature for 4 hours. The precipitate was collected by vacuum filtration, washed twice with 5 mL of water each time and dried under vacuum at 40° C. overnight to give 3.0 g (88% yield) of 5-methylaminosulfonyl-2-oxindole. $^1$H-NMR (300 MHz, DMSO-d6) δ 10.87 (br s, 1H, NH), 7.86 (br s, 1H, SO$_2$NH), 7.61 (d, 1H), 7.32 (d, 1H), 6.97 (d, 1H), 2.53 (s, 2H, CH$_2$), 2.36 (s, 3H, NHCH$_3$). MS m/z 226 [M].

O-12 2-Oxo-2,3-dihydro-1H-indole-5-sulfonic acid dimethylamide

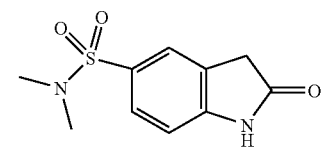

A suspension of 2.3 g of 5-chlorosulfonyl-2-oxindole in 10 mL of 2M dimethylamine in methanol was stirred at room temperature for 4 hours. The precipitate was collected by vacuum filtration, washed with 5 mL of 1 N sodium hydroxide and 5 mL of 1 N hydrochloric acid and dried under vacuum at 40° C. overnight to give 1.9 g (79% yield) of 5-dimethylaminosulfonyl-2-oxindole. $^1$H-NMR (300 MHz, DMSO-d6) δ 10.87 (br s, 1H, NH), 7.73 (d, 1H, CH), 7.58 (dd, 1H, CH), 7.02 (d, 1H, CH), 2.59 (s, 3H, CH$_3$), 2.54 (s, 2H, CH$_2$), 2.36 (s, 3H, CH$_3$). MS m/z 241 [M+1].

O-13 2-Oxo-2,3-dihydro-1H-indole-5-sulfonic acid thiazol-2-ylamide

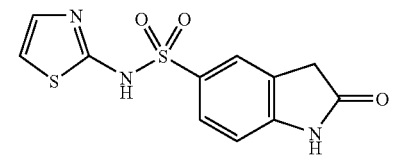

MS m/z 295 [M+1].

Synthesis of Amidosulfonyl-indolinones Indolinones

General Condensation Method for Condensed Indolinones

1. Condensation of an Oxindole and an Aldehyde Containing an Acid Group

A mixture of an appropriately substituted oxindole, an appropriately substituted aldehyde (1 equivalent) and piperidine (excess) in ethanol (0.2M) was stirred at between room temperature and 100° C. After completion, the mixture was concentrated and then triturated with dilute hydrochloric acid solution. The resulting precipitate was collected by vacuum filtration, washed with water and dried to give the desired product.

2. Condensation of an Oxindole and an Aldehyde Not Containing an Acid Group

A mixture of an appropriately substituted oxindole, an appropriately substituted aldehyde (1 equivalent) and piperidine (catalytic amount) in ethanol (0.2M) was stirred at between room temperature and 100° C. After completion, the reaction was cooled to room temperature and the resulting precipitate was collected by vacuum filtration, washed with ethanol and dried to give the desired product.

The following examples were prepared using Condensation Method 1 or 2.

Example 1

5-(6-Chloro-2,3-dihydro-indole-1-sulfonyl)-3-[1-[3,5-dimethyl-4-(piperazine-1-carbonyl)-1H-pyrrol-2-yl]-meth-(Z)-ylidene]-1,3-dihydro-indol-2-one FW 566.08

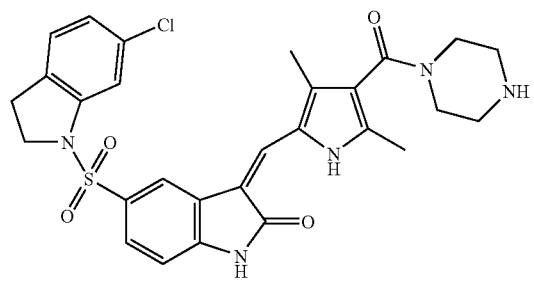

MS m/z 566 [M+1].

Example 2

5-(6-Chloro-2,3-dihydro-indole-1-sulfonyl)-3-[1-[4-(3,5-dimethyl-piperazine-1-carbonyl)-3,5-dimethyl-1H-pyrrol-2-yl]-meth-(Z)-ylidene]-1,3-dihydro-indol-2-one FW 594.14

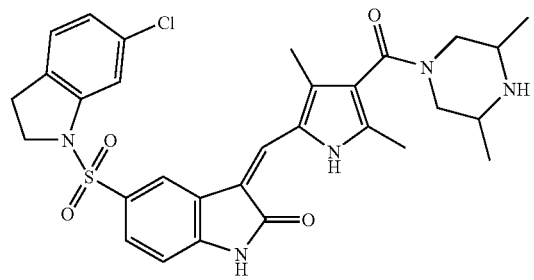

MS m/z 594 [M+1].

Example 3

3-[1-[4-(3,5-Dimethyl-piperazine-1-carbonyl)-3,5-dimethyl-1H-pyrrol-2-yl]-meth-(Z)-ylidene]-5-(5-fluoro-2,3-dihydro-indole-1-sulfonyl)-1,3-dihydro-indol-2-one FW 577.68

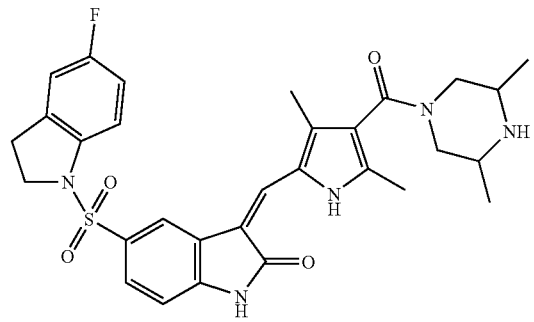

MS m/z 578 [M+1].

Example 4

5-(5-Fluoro-2,3-dihydro-indole-1-sulfonyl)-3-[1-{4-[4-(2-hydroxy-ethyl)-piperazine-1-carbonyl]-3,5-dimethyl-1H-pyrrol-2-yl}-meth-(Z)-ylidene]-1,3-dihydro-indol-2-one FW 593.68

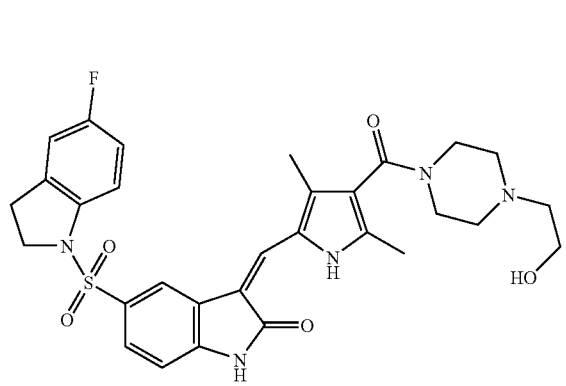

MS m/z 594 [M+1].

Example 5

3-[1-[3,5-Dimethyl-4-(piperazine-1-carbonyl)-1H-pyrrol-2-yl]-meth-(Z)-ylidene]-5-(5-fluoro-2,3-dihydro-indole-1-sulfonyl)-1,3-dihydro-indol-2-one FW 549.63

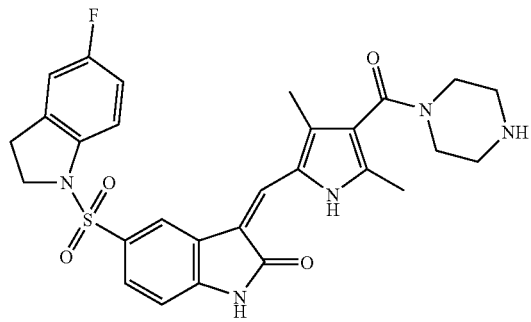

MS m/z 550 [M+1].

Example 6

5-[5-(3,4-Dihydro-2H-quinoline-1-sulfonyl)-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide FW 616.79

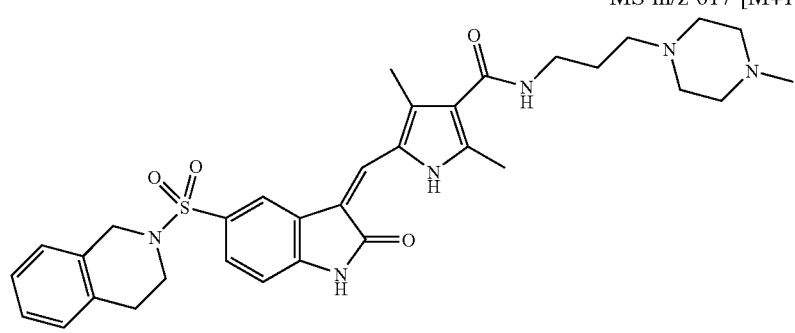

MS m/z 617 [M+1].

Example 7

5-[5-(5-Bromo-2,3-dihydro-indole-1-sulfonyl)-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide FW 681.66

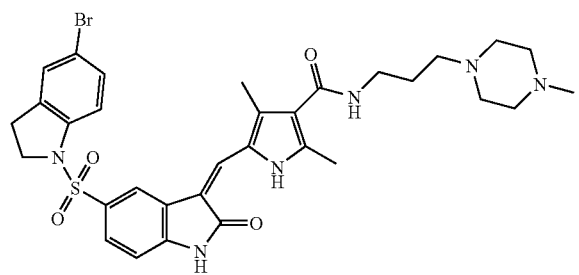

MS m/z 681 [M+1].

Example 8

5-[5-(3,4-Dihydro-2H-quinoline-1-sulfonyl)-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide FW 616.79

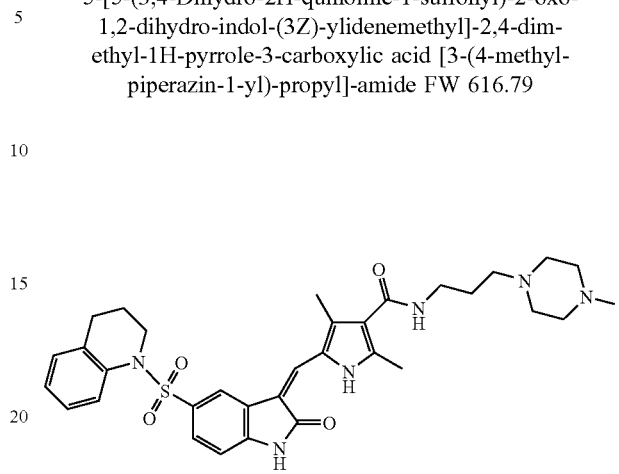

MS m/z 617 [M+1].

Example 9

5-[5-(2,3-Dihydro-indole-1-sulfonyl)-2-oxo-1,2-dihydro-indol-(3Z)-ylidenemethyl]-1H-pyrrole-2-carboxylic acid FW 435.46

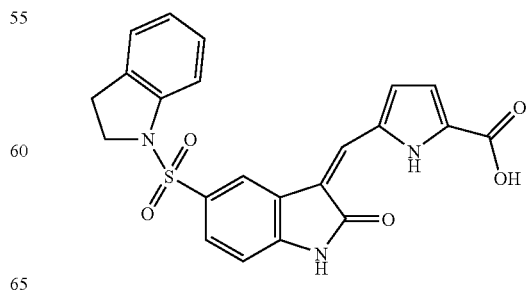

MS m/z 436 [M+1].

Example 10

5-[5-(3,4-Dihydro-2H-quinoline-1-sulfonyl)-2-oxo-1,2-dihydro-indol-(3Z)-ylidenemethyl]-1H-pyrrole-2-carboxylic acid FW 449.49

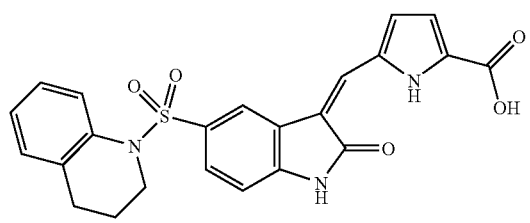

MS m/z 450 [M+1].

Example 11

5-[5-(3,4-Dihydro-1H-isoquinoline-2-sulfonyl)-2-oxo-1,2-dihydro-indol-(3Z)-ylidenemethyl]-1H-pyrrole-2-carboxylic acid FW 449.49

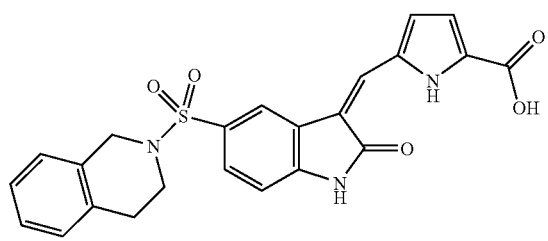

MS m/z 450 [M+1].

Example 12

5-[5-(5-Bromo-2,3-dihydro-indole-1-sulfonyl)-2-oxo-1,2-dihydro-indol-(3Z)-ylidenemethyl]-1H-pyrrole-2-carboxylic acid FW 514.36

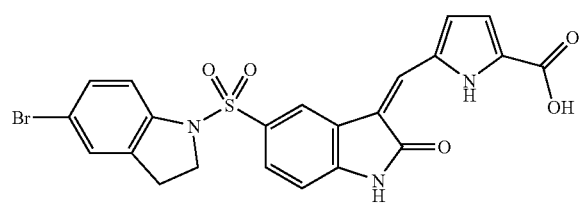

MS m/z 514 [M+1].

Example 13

3-[1-[3,5-Dimethyl-4-(4-methyl-piperazine-1-carbonyl)-1H-pyrrol-2-yl]-meth-(Z)-ylidene]-5-(5-methoxy-2,3-dihydro-indole-1-sulfonyl)-1,3-dihydro-indol-2-one FW 575.69

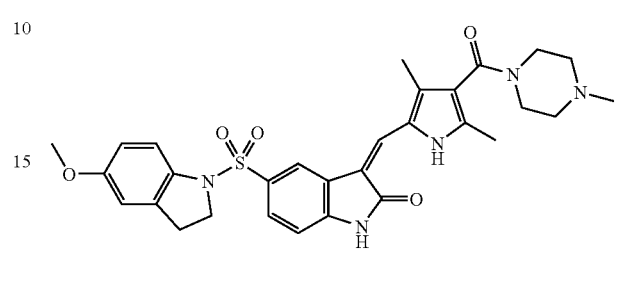

MS m/z 576 [M+1].

Example 14

3-[1-[3,5-Dimethyl-4-(3-morpholin-4-yl-propyl)-1H-pyrrol-2-yl]-meth-(Z)-ylidene]-5-(5-methoxy-2,3-dihydro-indole-1-sulfonyl)-1,3-dihydro-indol-2-one FW 576.72

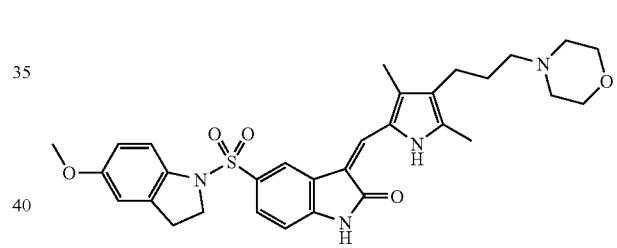

MS m/z 577 [M+1].

Example 15

5-(4-Chloro-2,3-dihydro-indole-1-sulfonyl)-3-[1-[3-(2-hydroxy-ethyl)-4-(4-methyl-piperazine-1-carbonyl)-1H-pyrrol-2-yl]-meth-(Z)-ylidene]-1,3-dihydro-indol-2-one FW 596.11

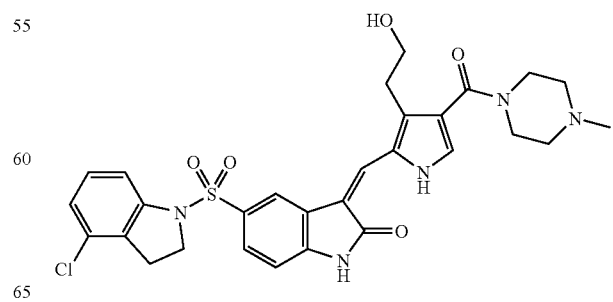

MS m/z 596 [M+1].

Example 16

2-{5-[5-(2,3-Dihydro-indole-1-sulfonyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide FW 573.72

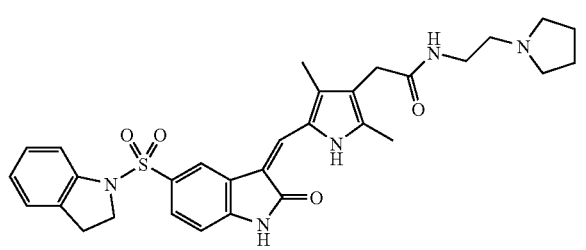

MS m/z 574 [M+1].

Example 17

5-[5-(5-Methoxy-2,3-dihydro-indole-1-sulfonyl)-2-oxo-1,2-dihydro-indol-(3Z)-ylidenemethyl]-2,4-dimethyl-1H-pyrrole-3-carboxylic acid (2-diethylamino-ethyl)-amide FW 591.74

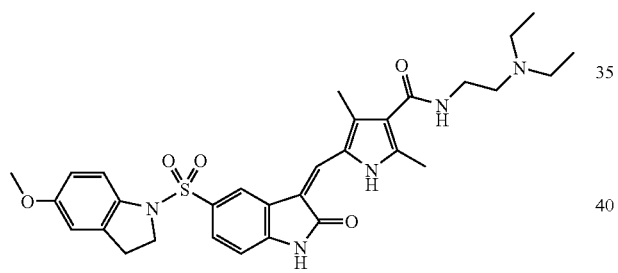

MS m/z 592 [M+1].

Example 18

N-(2-Diethylamino-ethyl)-2-{5-[5-(2,3-dihydro-indole-1-sulfonyl)-2-oxo-1,2-dihydro-indol-(3Z)-ylidenemethyl]-2,4-dimethyl-1H-pyrrol-3-yl}-acetamide FW 575.74

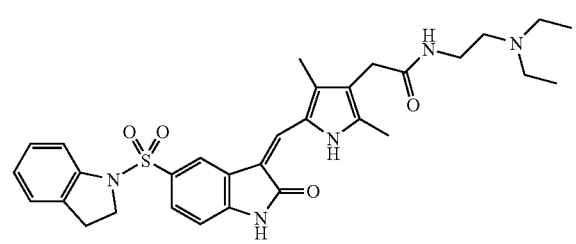

MS m/z 576 [M+1].

Example 19

5-(2,3-Dihydro-indole-1-sulfonyl)-3-[1-[3-(3-dimethylamino-propyl)-6,6-dimethyl-4,5,6,7-tetrahydro-1H-indol-2-yl]-meth-(Z)-ylidene]-1,3-dihydro-indol-2-one FW 558.75

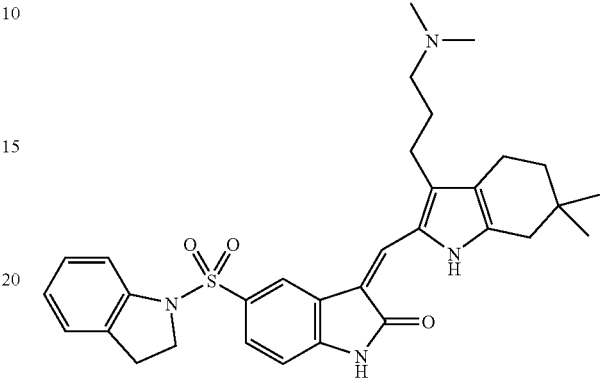

MS m/z 559 [M+1].

Example 20

5-(2,3-Dihydro-indole-1-sulfonyl)-3-[1-[3,5-dimethyl-4-(piperazine-1-carbonyl)-1H-pyrrol-2-yl]-meth-(Z)-ylidene]-1,3-dihydro-indol-2-one FW 531.64

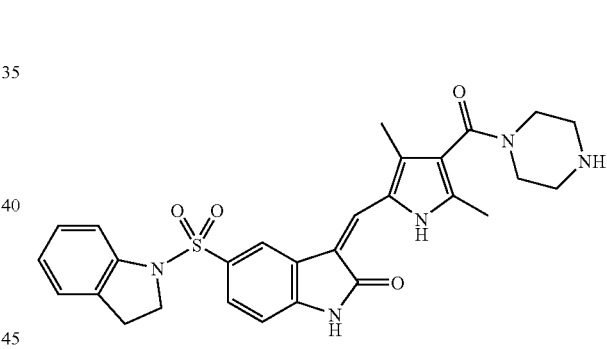

MS m/z 532 [M+1].

Example 21

2-{5-[5-[(3-Chloro-phenyl)-methyl-sulfamoyl]-2-oxo-1,2-dihydro-indol-(3Z)-ylidenemethyl]-2,4-dimethyl-1H-pyrrol-3-yl}-N-(2-morpholin-4-yl-ethyl)-acetamide FW 612.15

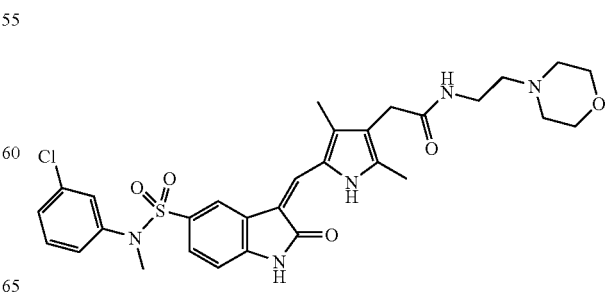

MS m/z 612 [M+1].

Example 22

3-[1-[3-(2-Hydroxy-ethyl)-4-(4-methyl-piperazine-1-carbonyl)-1H-pyrrol-2-yl]-meth-(Z)-ylidene]-5-(5-methoxy-2,3-dihydro-indole-1-sulfonyl)-1,3-dihydro-indol-2-one FW 591.69

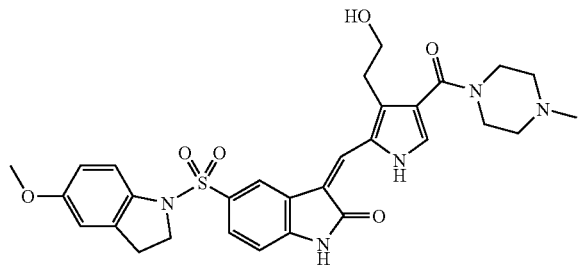

MS m/z 592 [M+1].

Example 23

2-{5-[5-(2,3-Dihydro-indole-1-sulfonyl)-2-oxo-1,2-dihydro-indol-(3Z)-ylidenemethyl]-2,4-dimethyl-1H-pyrrol-3-yl}-N-(2-morpholin-4-yl-ethyl)-acetamide FW 589.72

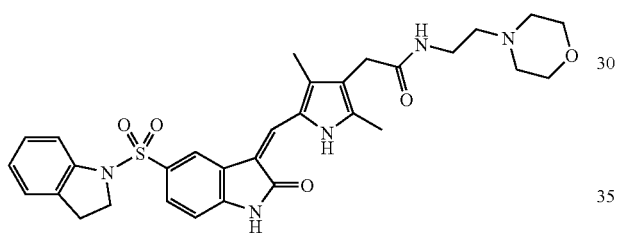

MS m/z 590 [M+1].

Example 24

3-[1-[3-(3-Diethylamino-propyl)-6,6-dimethyl-4,5,6,7-tetrahydro-1H-indol-2-yl]-meth-(Z)-ylidene]-5-(2,3-dihydro-indole-1-sulfonyl)-1,3-dihydro-indol-2-one FW 586.80

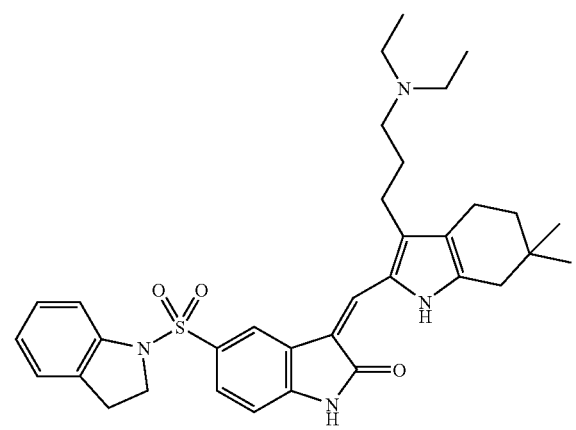

MS m/z 587 [M+1].

Example 25

5-[5-(2,3-Dihydro-indole-1-sulfonyl)-2-oxo-1,2-dihydro-indol-(3Z)-ylidenemethyl]-2,4-dimethyl-1H-pyrrole-3-carboxylic acid (2-diethylamino-ethyl)-amide FW 561.71

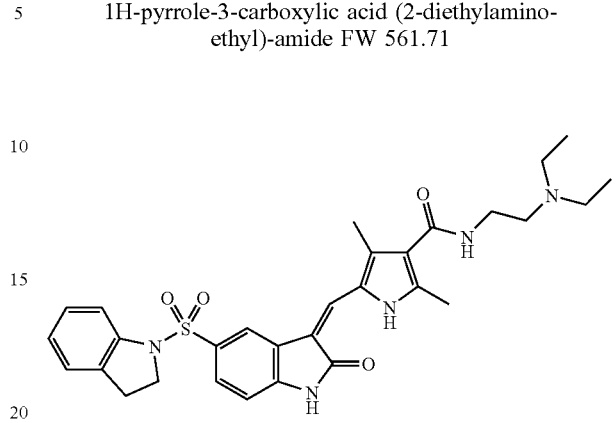

MS m/z 562 [M+1].

Example 26

5-[5-(2,3-Dihydro-indole-1-sulfonyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide FW 559.69

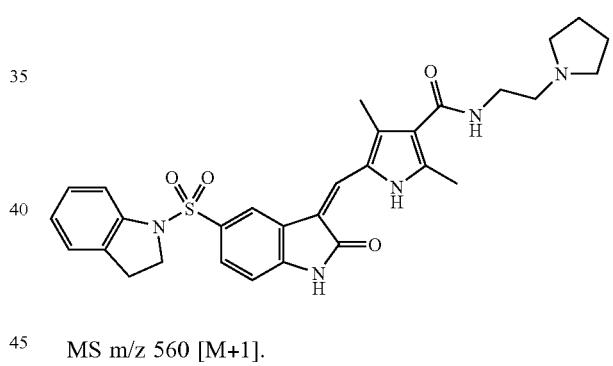

MS m/z 560 [M+1].

Example 27

5-(4-Chloro-2,3-dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 580.11

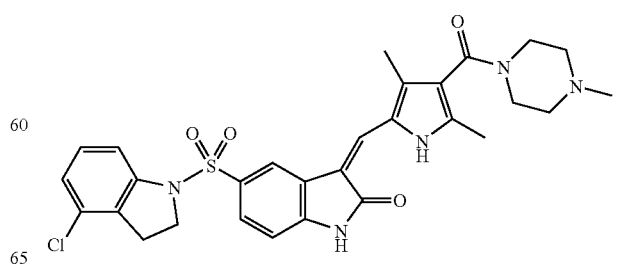

MS m/z 580 [M+1].

Example 28

5-(2,3-Dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 545.67

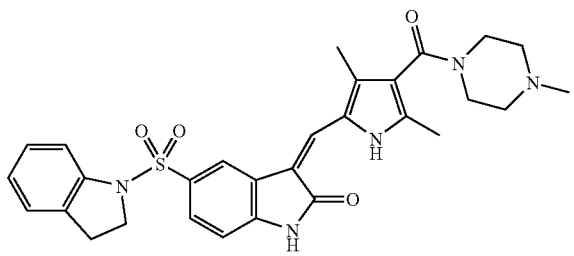

MS m/z 546 [M+1].

Example 29

5-[5-(2,3-Dihydro-indole-1-sulfonyl)-2-oxo-1,2-dihydro-indol-(3Z)-ylidenemethyl]-2-ethyl-4-methyl-1H-pyrrole-3-carboxylic acid (2-pyrrolidin-1-yl-ethyl)-amide FW 573.72

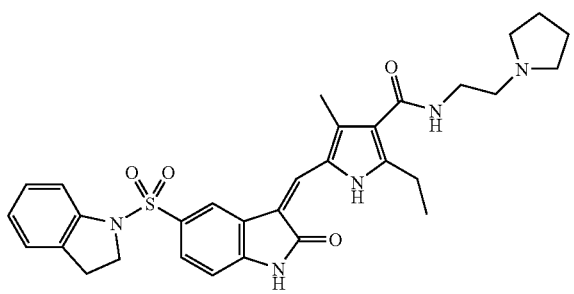

MS m/z 574 [M+1].

Example 30

5-[5-(2,3-Dihydro-indole-1-sulfonyl)-2-oxo-1,2-dihydro-indol-(3Z)-ylidenemethyl]-2,4-dimethyl-1H-pyrrole-3-carboxylic acid [3-(4-methyl-piperazin-1-yl)-propyl]-amide FW 602.76

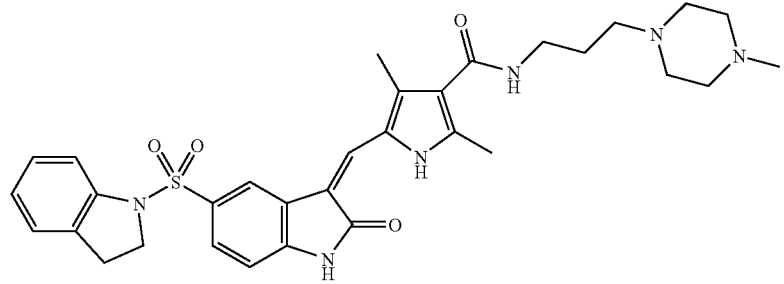

MS m/z 603 [M+1].

Example 31

5-[5-(2,3-Dihydro-indole-1-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester FW 617.77

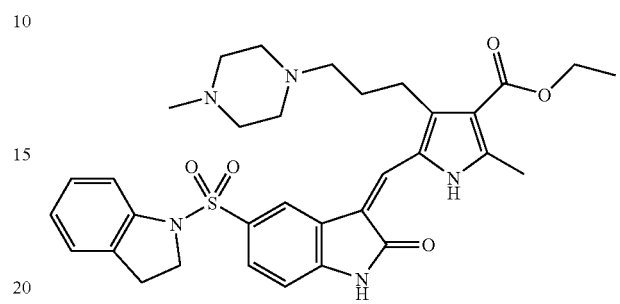

MS m/z 618 [M+1].

Example 32

5-[5-(2,3-Dihydro-indole-1-sulfonyl)-2-oxo-1,2-dihydro-indol-(3Z)-ylidenemethyl]-2-methyl-4-(3-morpholin-4-yl-propyl)-1H-pyrrole-3-carboxylic acid ethyl ester FW 604.73

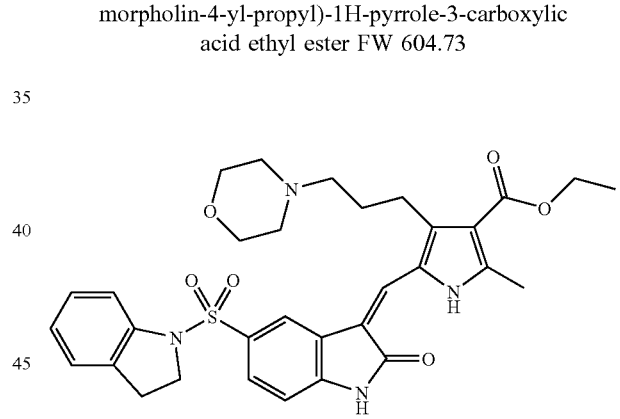

MS m/z 605 [M+1].

Example 33

5-[5-(2,3-Dihydro-indole-1-sulfonyl)-2-oxo-1,2-dihydro-indol-(3Z)-ylidenemethyl]-4-(3-dimethylamino-propyl)-2-methyl-1H-pyrrole-3-carboxylic acid ethyl ester FW 562.69

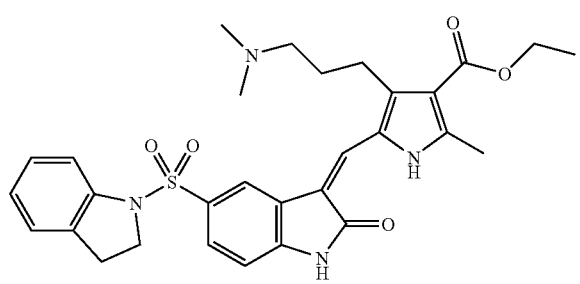

MS m/z 563 [M+1].

Example 34

5-(2,3-Dihydro-indole-1-sulfonyl)-3-[1-[3-methyl-5-(4-methyl-piperazine-1-carbonyl)-1H-pyrrol-2-yl]-meth-(Z)-ylidene]-1,3-dihydro-indol-2-one FW 531.64

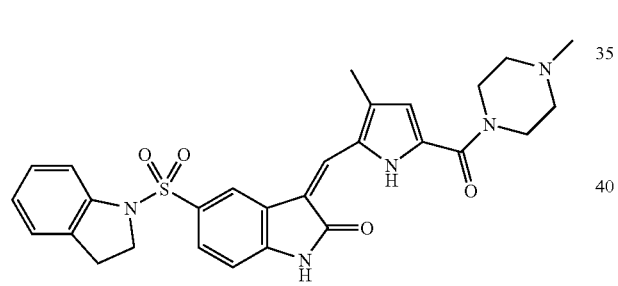

MS m/z 532 [M+1].

Example 35

5-(2,3-Dihydro-indole-1-sulfonyl)-3-[1-[5-(4-methyl-piperazine-1-carbonyl)-1H-pyrrol-2-yl]-meth-(Z)-ylidene]-1,3-dihydro-indol-2-one FW 517.61

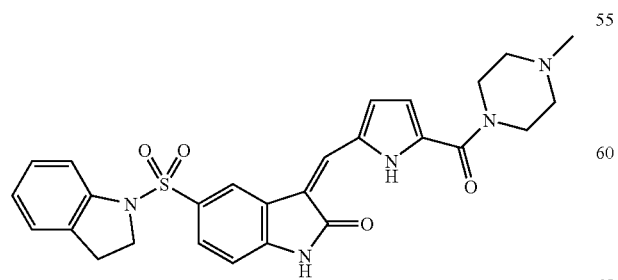

MS m/z 518 [M+1].

Example 36

5-(2,3-Dihydro-indole-1-sulfonyl)-3-[1-[3-(3-pyrrolidin-1-yl-propyl)-4,5,6,7-tetrahydro-1H-indol-2-yl]-meth-(Z)-ylidene]-1,3-dihydro-indol-2-one FW 556.73

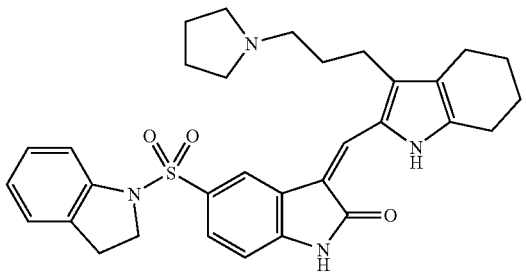

MS m/z 557 [M+1].

Example 37

5-(2,3-Dihydro-indole-1-sulfonyl)-3-[1-{3-[3-(4-methyl-piperazin-1-yl)-propyl]-4,5,6,7-tetrahydro-1H-indol-2-yl}-meth-(Z)-ylidene]-1,3-dihydro-indol-2-one FW 585.77

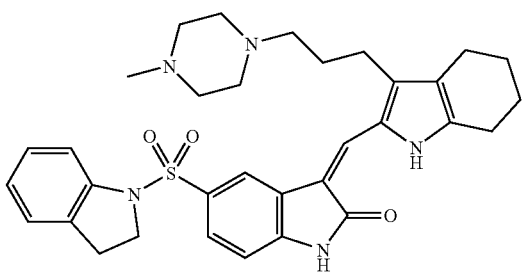

MS m/z 586 [M+1].

Example 38

5-(2,3-Dihydro-indole-1-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one FW 572.73

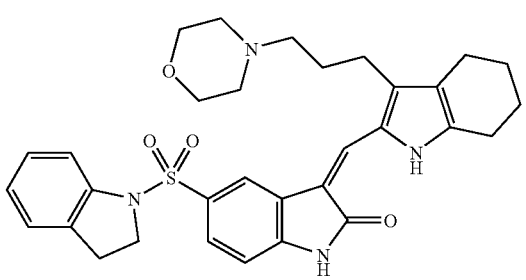

MS m/z 573 [M+1].

Example 39

5-(2,3-Dihydro-indole-1-sulfonyl)-3-[1-[6,6-dimethyl-3-(3-morpholin-4-yl-propyl)-4,5,6,7-tetrahydro-1H-indol-2-yl]-meth-(Z)-ylidene]-1,3-dihydro-indol-2-one FW 600.79

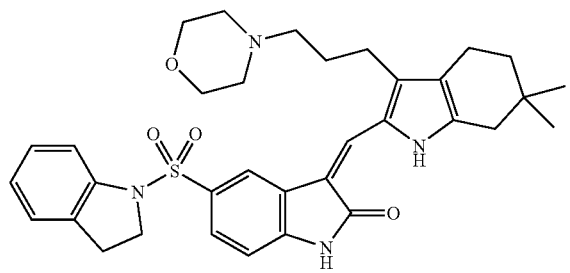

MS m/z 601 [M+1].

Example 40

5-(3,4-Dihydro-1H-isoquinoline-2-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 559.69

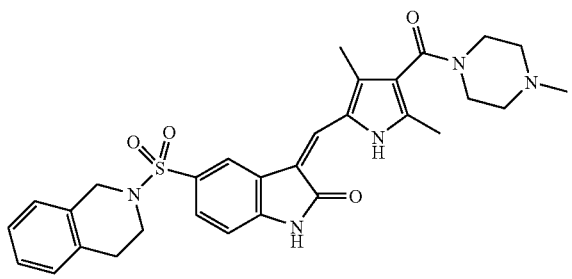

MS m/z 560 [M+1].

Example 41

5-(5-Bromo-2,3-dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 624.56

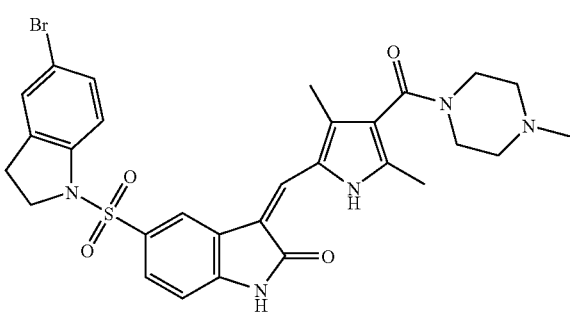

MS m/z 624 [M+1].

Example 42

5-(3,4-Dihydro-2H-quinoline-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 559.69

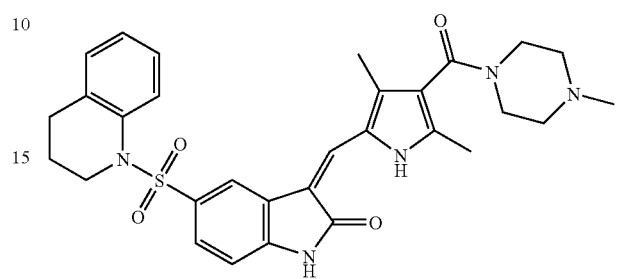

MS m/z 560 [M+1].

Example 43

5-[5-(5-Bromo-2,3-dihydro-indole-1-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester FW 696.67

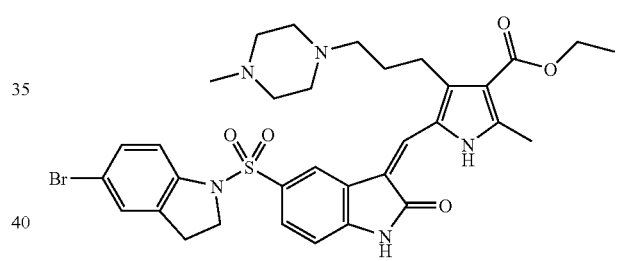

MS m/z 696 [M+1].

Example 44

5-[5-(3,4-Dihydro-1H-isoquinoline-2-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester FW 631.80

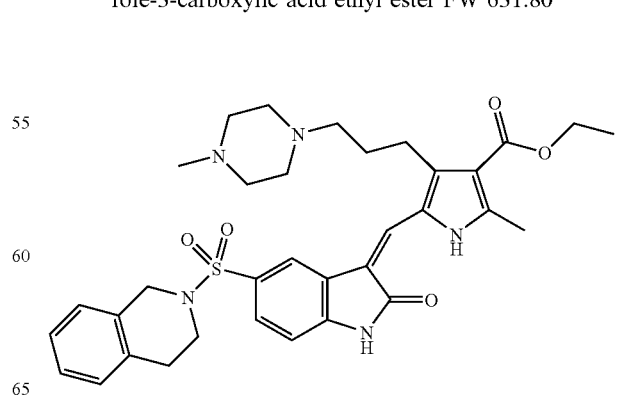

MS m/z 632 [M+1].

Example 45

5-[5-(3,4-Dihydro-2H-quinoline-1-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester FW 631.80

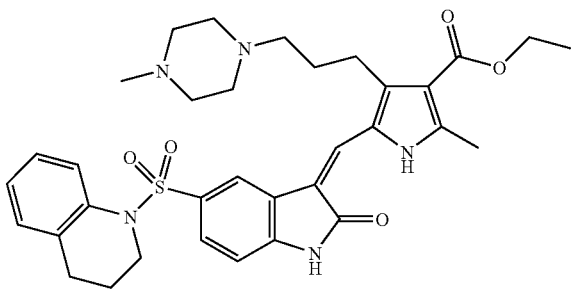

MS m/z 632 [M+1].

Example 46

5-(6-Chloro-2,3-dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one FW 580.11

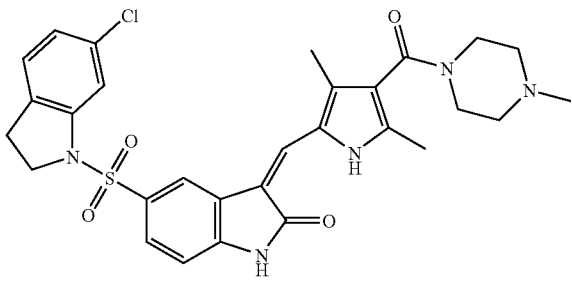

MS m/z 580 [M+1].

Example 47

5-(6-Chloro-2,3-dihydro-indole-1-sulfonyl)-3-[1-[3,5-dimethyl-4-(morpholine-4-carbonyl)-1H-pyrrol-2-yl]-meth-(Z)-ylidene]-1,3-dihydro-indol-2-one FW 567.07

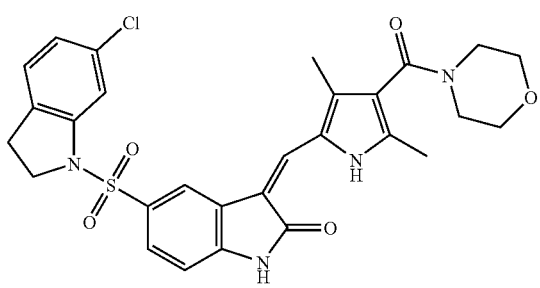

MS m/z 567 [M+1].

Example 48

3-[1-[3,5-Dimethyl-4-(4-methyl-piperazine-1-carbonyl)-1H-pyrrol-2-yl]-meth-(Z)-ylidene]-5-(5-fluoro-2,3-dihydro-indole-1-sulfonyl)-1,3-dihydro-indol-2-one FW 563.66

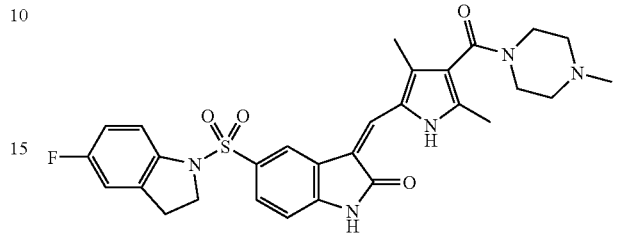

MS m/z 564 [M+1].

Example 49

3-[1-[3,5-Dimethyl-4-(morpholine-4-carbonyl)-1H-pyrrol-2-yl]-meth-(Z)-ylidene]-5-(5-fluoro-2,3-dihydro-indole-1-sulfonyl)-1,3-dihydro-indol-2-one FW 550.61

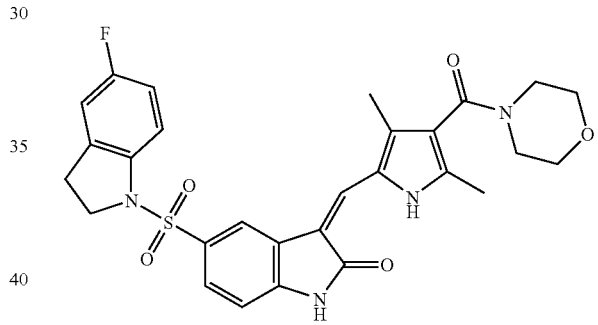

MS m/z 551 [M+1].

Example 50

5-[5-(5-Fluoro-2,3-dihydro-indole-1-sulfonyl)-2-oxo-1,2-dihydro-indol-(3Z)-ylidenemethyl]-2,4-dimethyl-1H-pyrrole-3-carboxylic acid (2-diethylamino-ethyl)-amide FW 579.70

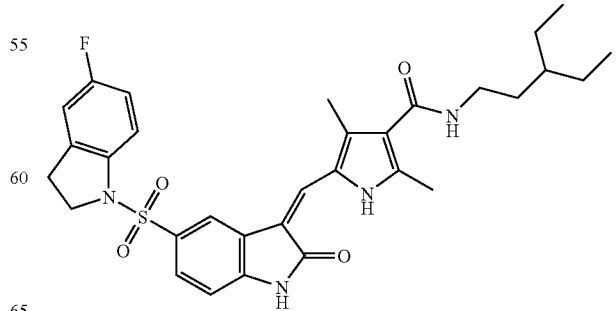

MS m/z 580 [M+1].

Example 51

5-(5-Bromo-2,3-dihydro-indole-1-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one FW 651.63

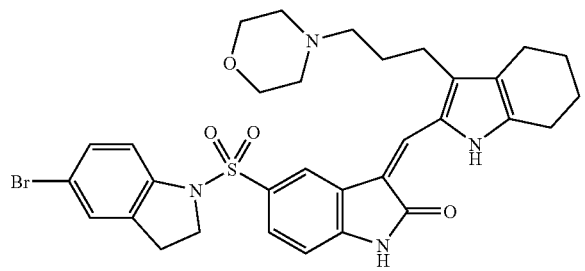

MS m/z 651 [M+1].

Example 52

5-(3,4-Dihydro-1H-isoquinoline-2-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one SU11384 FW 586.76

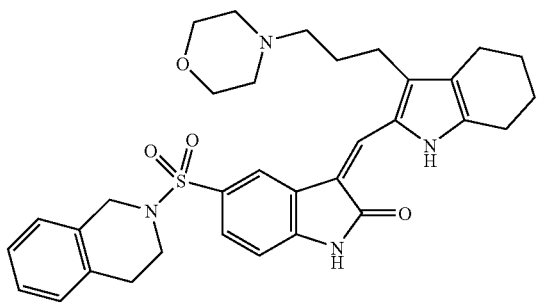

MS m/z 587 [M+1].

Example 53

5-(3,4-Dihydro-2H-quinoline-1-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one FW 586.76

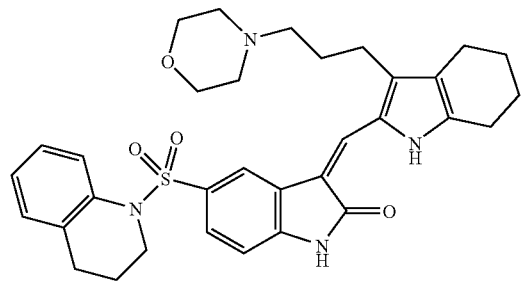

MS m/z 587 [M+1].

Example 54

5-(6-Chloro-2,3-dihydro-indole-1-sulfonyl)-3-[1-{4-[4-(2-hydroxy-ethyl)-piperazine-1-carbonyl]-3,5-dimethyl-1H-pyrrol-2-yl}-meth-(Z)-ylidene]-1,3-dihydro-indol-2-one FW 610.14

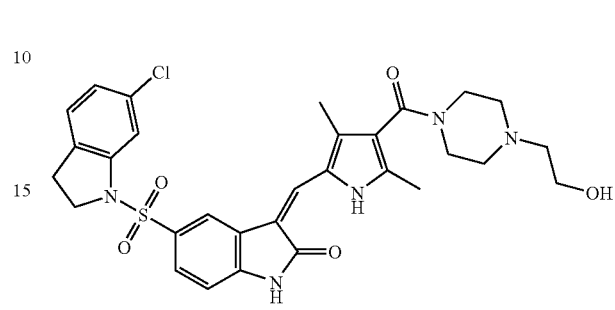

MS m/z 610 [M+1].

Example 55

2-{2,4-Dimethyl-5-[2-oxo-5-sulfamoyl-1,2-dihydro-indol-(3Z)-ylidenemethyl]-1H-pyrrol-3-yl}-N-(2-pyrrolidin-1-yl-ethyl)-acetamide FW 471.58

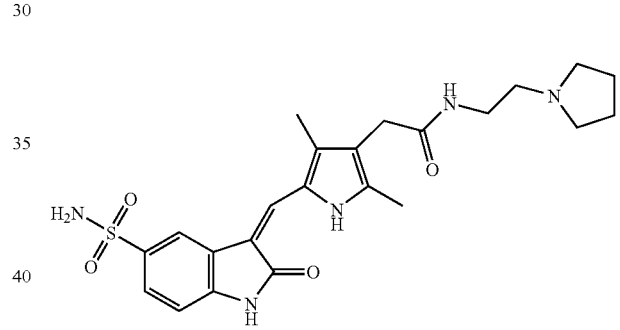

MS m/z 472 [M+1].

Example 56

2-{2,4-Dimethyl-5-[5-methylsulfamoyl-2-oxo-1,2-dihydro-indol-(3Z)-ylidenemethyl]-1H-pyrrol-3-yl}-N-(2-pyrrolidin-1-yl-ethyl)-acetamide FW 485.61

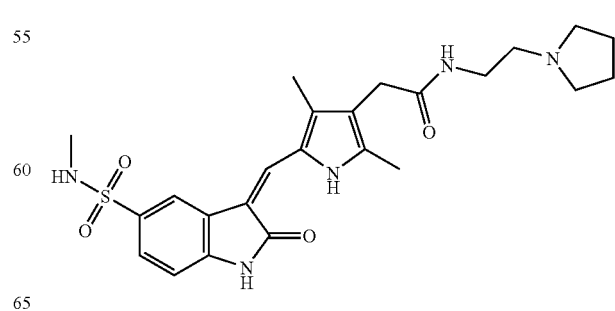

MS m/z 486 [M+1].

Example 57

2-{5-[5-Dimethylsulfamoyl-2-oxo-1,2-dihydro-indol-(3Z)-ylidenemethyl]-2,4-dimethyl-1H-pyrrol-3yl}-N-(2-pyrrolidin-1-yl-ethyl)-acetamide FW 499.64

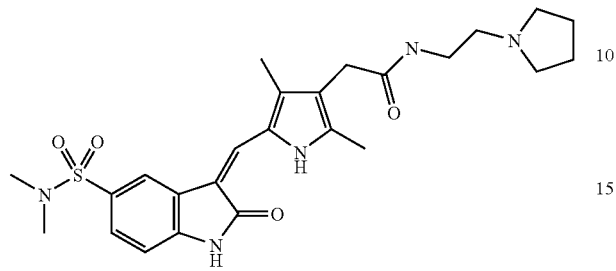

MS m/z 500 [M+1].

Example 58

2-{5-[5-(2,3-Dihydro-indole-1-sulfonyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamideFW 573.71

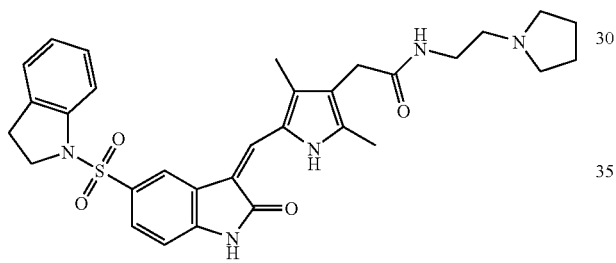

MS m/z 574 [M+1].

Example 59

3-[1-{3,5-Dimethyl-4-[4-(4-methyl-piperazin-1-carbonyl)-phenyl]-1H-pyrrol-2-yl}-meth-(Z)-ylidene]-2-oxo-2,3-dihydro-1H-indole-5-sulfonic acid dimethylamide FW 547.68

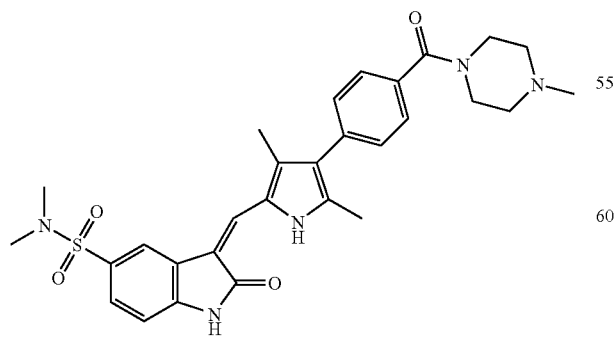

MS m/z 548 [M+1].

Example 60

3-[1-{3,5-Dimethyl-4-[3-(morpholine-4-carbonyl)-phenyl]-1H-pyrrol-2-yl}-meth-(Z)-ylidene]-2-oxo-2,3-dihydro-1H-indole-5-sulfonic acid amide FW 506.58

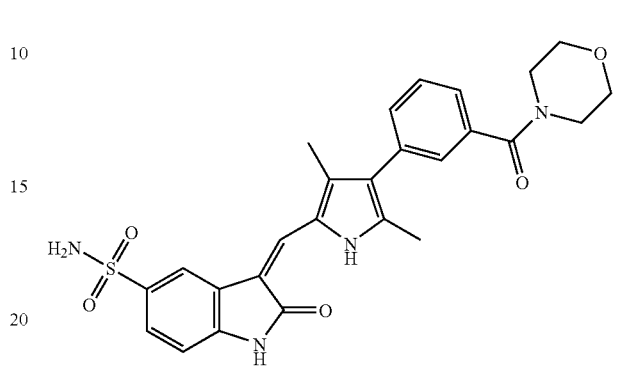

MS m/z 507 [M+1].

Example 61

3-[1-[4-(4-Hydroxy-piperidin-1-ylmethyl)-3,5-dimethyl-1H-pyrrol-2-yl]-meth-(Z)-ylidene]-2-oxo-2,3-dihydro-1H-indole-5-sulfonic acid thiazol-2-ylamide FW 513.64

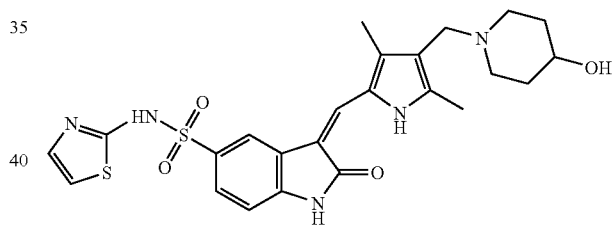

MS m/z 514 [M+1].

Example 62

2-{5-[5-[(3-Chloro-phenyl)-methyl-sulfamoyl]-2-oxo-1,2-dihydro-indol-(3Z)-ylidenemethyl]-2,4-dimethyl-1H-pyrrol-3-yl}-N-(2-pyrrolidin-1-yl-ethyl)-acetamide FW 596.15

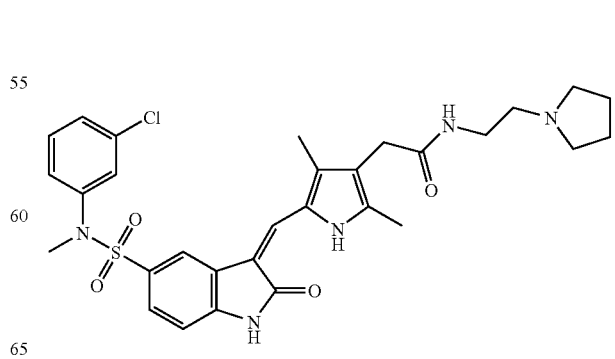

MS m/z 596 [M+1].

Example 63

N-(2-Diethylamino-ethyl)-2-{2,4-dimethyl-5-[2-oxo-5-sulfamoyl-1,2-dihydro-indol-(3Z)-ylidenemethyl]-1H-pyrrol-3-yl}-acetamide FW 473.60

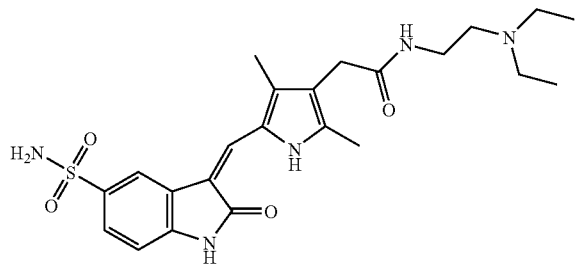

MS m/z 474 [M+1].

Example 64

N-(2-Diethylamino-ethyl)-2-{2,4-dimethyl-5-[5-methylsulfamoyl-2-oxo-1,2-dihydro-indol-(3Z)-ylidenemethyl]-1H-pyrrol-3-yl}-acetamide FW 487.63

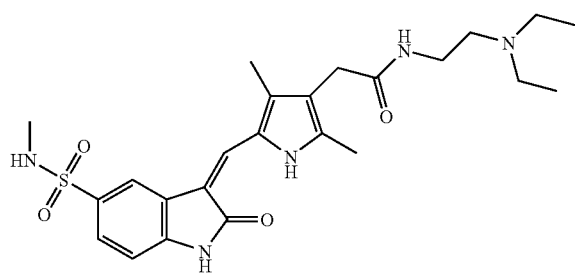

MS m/z 488 [M+1].

Example 65

2-{2,4-Dimethyl-5-[2-oxo-5-sulfamoyl-1,2-dihydro-indol-(3Z)-ylidenemethyl]-1H-pyrrol-3-yl}-N-(2-morpholin-4-yl-ethyl)-acetamide FW 487.58

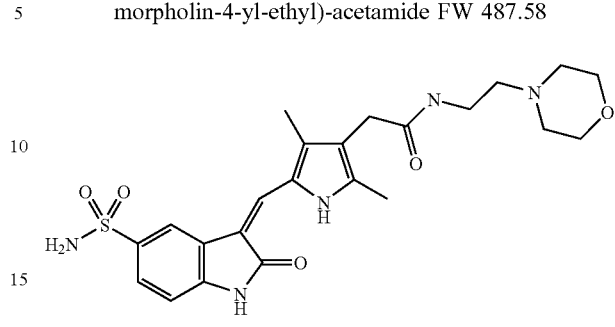

MS m/z 488 [M+1].

Example 66

3-[1-{3,5-Dimethyl-4-[3-(morpholine-4-carbonyl)-phenyl]-1H-pyrrol-2-yl}-meth-(Z)-ylidene]-2-oxo-2,3-dihydro-1H-indole-5-sulfonic acid methylamide FW 520.61

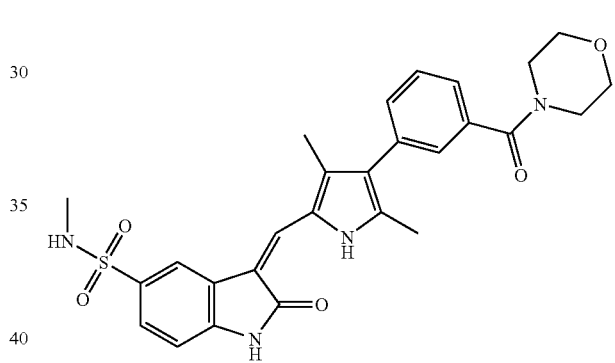

MS m/z 521 [M+1].

Example 67

3-[1-{3,5-Dimethyl-4-[3-(morpholine-4-carbonyl)-phenyl]-1H-pyrrol-2-yl}-meth-(Z)-ylidene]-2-oxo-2,3-dihydro-1H-indole-5-sulfonic acid dimethylamide FW 534.64

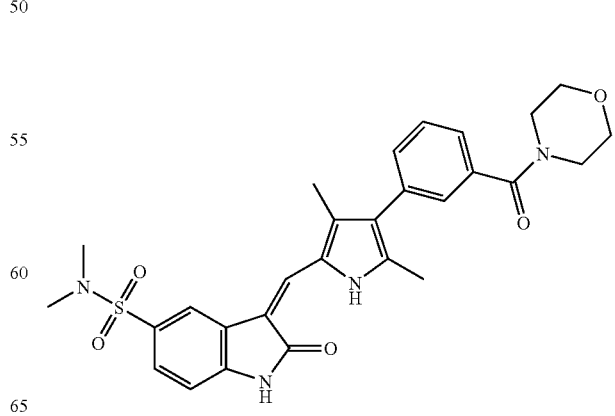

MS m/z 535 [M+1].

Example 68

2-{5-[5-[(3-Chloro-phenyl)-methyl-sulfamoyl]-2-oxo-1,2-dihydro-indol-(3Z)-ylidenemethyl]-2,4-dimethyl-1H-pyrrol-3-yl}-N-(2-diethylamino-ethyl)-acetamide FW 598.17

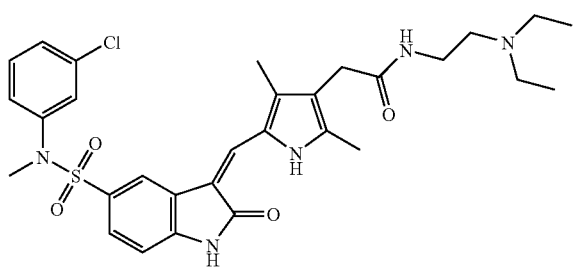

MS m/z 598 [M+1].

Example 69

2-{2,4-Dimethyl-5-[5-methylsulfamoyl-2-oxo-1,2-dihydro-indol-(3Z)-ylidenemethyl]-1H-pyrrol-3-yl}-N-(2-morpholin-4-yl-ethyl)-acetamide FW 501.61

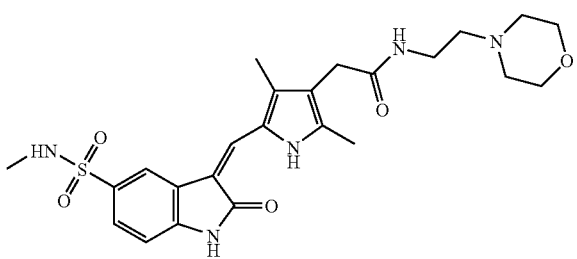

MS m/z 502 [M+1].

Example 70

2-{5-[5-Dimethylsulfamoyl-2-oxo-1,2-dihydro-indol-(3Z)-ylidenemethyl]-2,4-dimethyl-1H-pyrrol-3-yl}-N-(2-morpholin-4-yl-ethyl)-acetamide FW 515.64

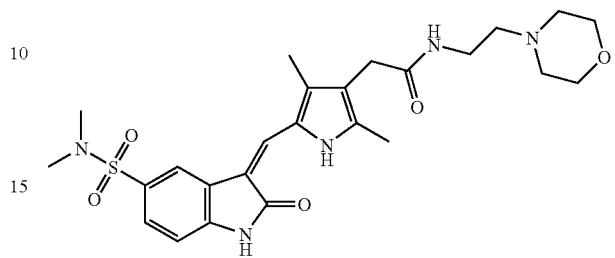

MS m/z 516 [M+1].

Example 71

3-[1-(3,5-Diethyl-4-morpholin-4-ylmethyl-1H-pyrrol-2-yl)-meth-(Z)-ylidene]-2-oxo-2,3-dihydro-1H-indole-5-sulfonic acid amide FW 444.56

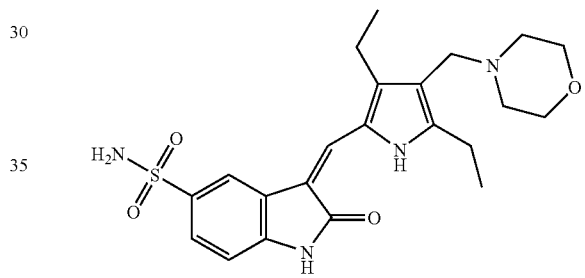

MS m/z 445 [M+1].

Example 72

3-[1-{3,5-Dimethyl-4-[4-(morpholine-4-carbonyl)-phenyl]-1H-pyrrol-2-yl}-meth-(Z)-ylidene]-2-oxo-2,3-dihydro-1H-indole-5-sulfonic acid amide FW 506.58

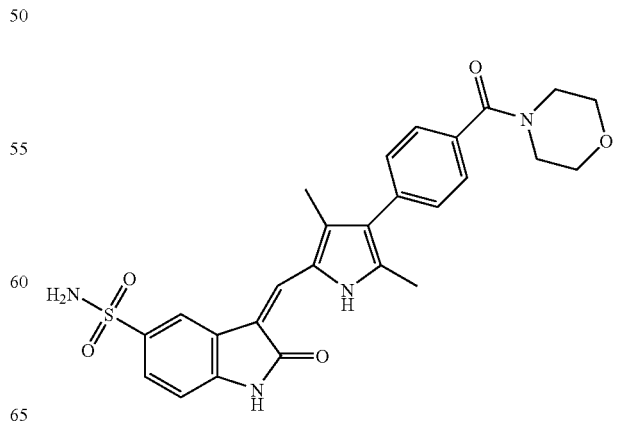

MS m/z 507 [M+1].

Example 73

3-[1-{3,5-Dimethyl-4-[3-(4-methyl-piperazine-1-carbonyl)-phenyl]-1H-pyrrol-2-yl}-meth-(Z)-ylidene]-2-oxo-2,3-dihydro-1H-indole-5-sulfonic acid amide FW 519.63

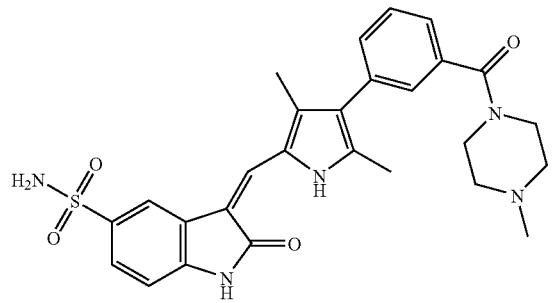

MS m/z 520 [M+1].

Example 74

3-[1-{3,5-Dimethyl-4-[3-(4-methyl-piperazine-1-carbonyl)-phenyl]-1H-pyrrol-2-yl}-meth-(Z)-ylidene]-2-oxo-2,3-dihydro-1H-indole-5-sulfonic acid methylamide FW 533.65

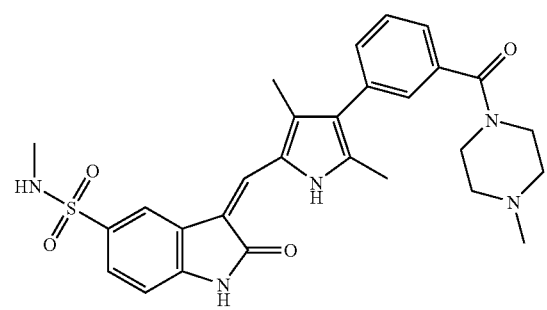

MS m/z 534 [M+1].

Example 75

N-(2-Diethylamino-ethyl)-2-{5-[5-dimethylsulfamoyl-2-oxo-1,2-dihydro-indol-(3Z)-ylidenemethyl]-2,4-dimethyl-1H-pyrrol-3-yl}-acetamide FW 501.65

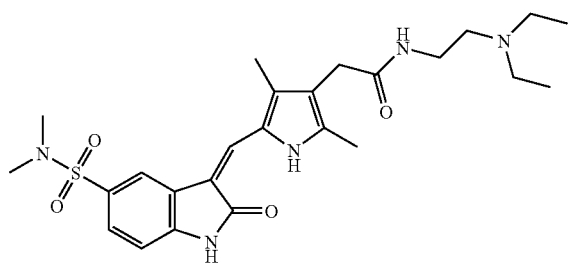

MS m/z 502 [M+1].

Example 76

3-[1-{3,5-Dimethyl-4-[4-(morpholine-4-carbonyl)-phenyl]-1H-pyrrol-2-yl}-meth-(Z)-ylidene]-2-oxo-2,3-dihydro-1H-indole-5-sulfonic acid methylamide FW 520.61

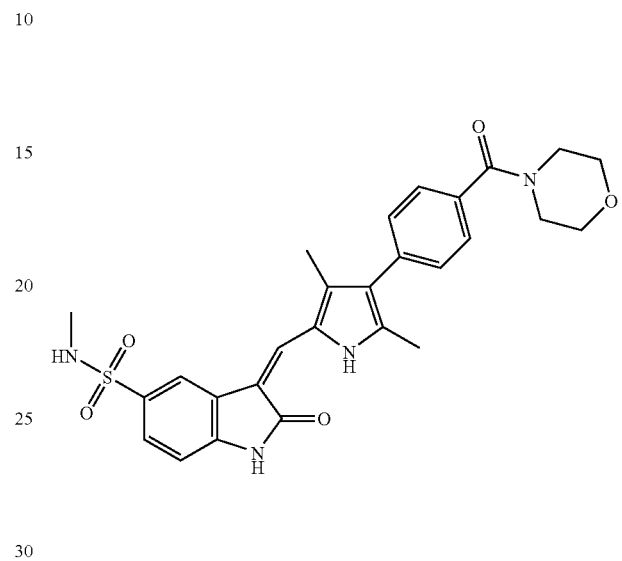

MS m/z 521 [M+1].

Example 77

3-[1-{3,5-Dimethyl-4-[4-(morpholine-4-carbonyl)-phenyl]-1H-pyrrol-2-yl}-meth-(Z)-ylidene]-2-oxo-2,3-dihydro-1H-indole-5-sulfonic acid dimethylamide PHA710283 FW 534.64

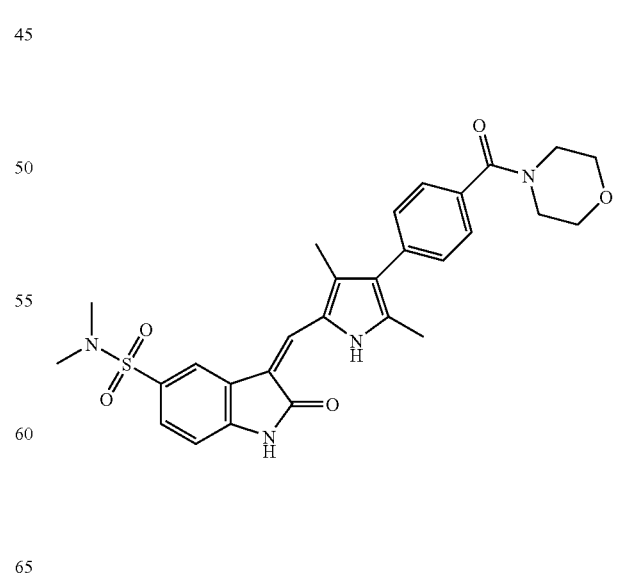

MS m/z 535 [M+1].

Example 78

3-[1-{3,5-Dimethyl-4-[4-(4-methyl-piperazine-1-carbonyl)-phenyl]-1H-pyrrol-2-yl}-meth-(Z)-ylidene]-2-oxo-2,3-dihydro-1H-indole-5-sulfonic acid amide FW 519.63

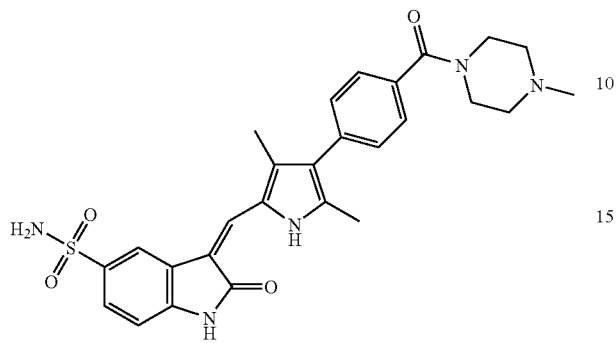

MS m/z 520 [M+1].

Example 79

3-[1-{3,5-Dimethyl-4-[4-(4-methyl-piperazine-1-carbonyl)-phenyl]-1H-pyrrol-2-yl}-meth-(Z)-ylidene]-2-oxo-2,3-dihydro-1H-indole-5-sulfonic acid methylamide FW 533.65

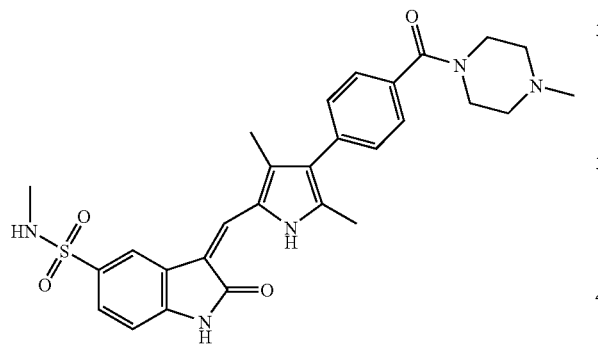

MS m/z 534 [M+1].

Example 80

3-[1-{3,5-Dimethyl-4-[3-(4-methyl-piperazine-1-carbonyl)-phenyl]-1H-pyrrol-2-yl}-meth-(Z)-ylidene]-2-oxo-2,3-dihydro-1H-indole-5-sulfonic acid dimethylamide FW 547.68

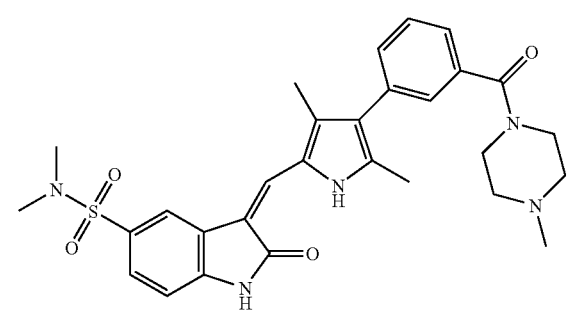

MS m/z 548 [M+1].

Example 81

3-[1-(3-Nitro-1H-pyrrol-2-yl)-meth-(Z)-ylidene]-2-oxo-2,3-dihydro-1H-indole-5-sulfonic acid methylamide FW 348.34

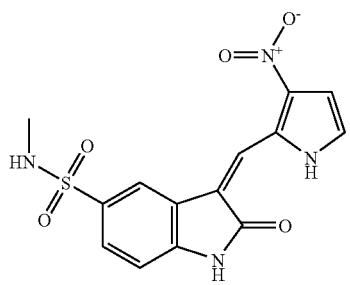

MS m/z 349 [M+1].

Example 82

3-[1-(4-Nitro-1H-pyrrol-2-yl)-meth-(Z)-ylidene]-2-oxo-2,3-dihydro-1H-indole-5-sulfonic acid methylamide FW 348.34

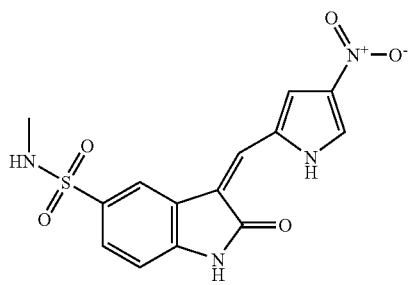

MS m/z 349 [M+1].

It will be appreciated that, in any given series of compounds, a range of biological activities will be observed. In its presently preferred aspects, this invention relates to novel 5-sulfonamido substituted indolinones capable of modulating, regulating and/or inhibiting protein kinase activity. The following assays may be employed to select those compounds demonstrating the optimal degree of the desired activity.

Assay Procedures

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-Flk-1 Bioassay

This assay analyzes the tyrosine kinase activity of GST-Flk1 on poly(glu-tyr) peptides.

Materials and Reagents:

1. Corning 96-well ELISA plates (Corning Catalog No. 25805-96).
2. poly(glu-tyr) 4:1, lyophilizate (Sigma Catalog No. P0275), 1 mg/ml in sterile PBS.
3. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
4. PBST Buffer: to 1 L of PBS Buffer, add 1.0 ml Tween-20.
5. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
6. 1% BSA in PBS: add 10 g BSA to approx. 990 ml PBS buffer, stir to dissolve. Adjust total volume to 1 L with PBS buffer, filter to remove particulate matter.
7. 50 mM Hepes pH 7.5.
8. GST-Flk1cd purified from sf9 recombinant baculovirus transformation (SUGEN, Inc.).
9. 4% DMSO in $dH_2O$.
10. 10 mM ATP in $dH_2O$.
11. 40 mM $MnCl_2$
12. Kinase Dilution Buffer (KDB): mix 10 ml Hepes (pH 7.5), 1 ml 5M NaCl, 40µL 100 mM sodium orthovanadate and 0.4 ml of 5% BSA in $dH_2O$ with 88.56 ml $dH_2O$.
13. NUNC 96-well V bottom polypropylene plates, Applied Scientific Catalog # AS-72092
14. EDTA: mix 14.12 g ethylenediaminetetraacetic acid (EDTA) with approx. 70ml $dH_2O$. Add 10 N NaOH until EDTA dissolves. Adjust pH to 8.0. Adjust total volume to 100 ml with $dH_2O$.
15. $1°$ and $2°$ Antibody Dilution Buffer: mix 10 ml of 5% BSA in PBS buffer with 89.5 ml TBST.
16. Anti-phosphotyrosine rabbit polyclonal antisera (SUGEN, Inc.)
17. Goat anti-rabbit HRP conjugate.
18. ABST solution: To approx. 900 ml $dH_2O$ add 19.21 g citric acid and 35.49 g $Na_2HPO_4$. Adjust pH to 4.0 with phosphoric acid. Add 2,2'-Azinobis(3-ethyl-benzthiazoline-6-sulfonic acid (ABTS, Sigma, Cat. No. A-1888, hold for approx. ½ hour, filter.
19. 30% Hydrogen Peroxide.
20. ABST/$H_2O_2$: add 3 µl of $H_2O_2$ to 15 ml of ABST solution.
21. 0.2M HCl.

Procedure:

1. Coat Corning 96-well ELISA plates with 2 µg of polyEY in 100 µl PBS/well, hold at room temperature for 2 hours or at 4° C. overnight. Cover plates to prevent evaporation.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5, 150 µl/well).
6. Dilute test compound with $dH_2O$/4% DMSO to 4 times the desired final assay concentration in 96-well polypropylene plates.
7. Add 25 µl diluted test compound to each well of ELISA plate. In control wells, place 25 µl of $dH_2O$/4% DMSO.
8. Dilute GST-Flk1 0.005 µg (5 ng)/well in KDB.
9. Add 50 µl of diluted enzyme to each well.
10. Add 25 µl 0.5M EDTA to negative control wells.
11. Add 25 µl of 40 mM $MnCl_2$ with 4× ATP (2 µM) to all wells (100 µl final volume, 0.5 µM ATP final concentration in each well).
12. Incubate, with shaking, for 15 minutes at room temperature.
13. Stop reaction by adding 25 µl of 500 mM EDTA to each well.
14. Wash 3× with TBST and pat plate on paper towel to remove excess liquid.
15. Add 100 µl per well anti-phosphotyrosine antisera, 1:10,000 dilution in antibody dilution buffer. Incubate, with shaking, for 90 min. at room temperature.
16. Wash as in step 14.
17. Add 100 µl/well of goat anti-rabbit HRP conjugate (1:6,000 in antibody dilution buffer). Incubate, with shaking, for 90 minutes are room temperature.
18. Wash as in Step 14.
19. Add 100 µl room temperature ABST/$H_2O_2$ solution to each well.
20. Incubate, with shaking for 15 to 30 minutes at room temperature.
21. If necessary, stop reaction by adding 100 µl of 0.2M HCl to each well.
22. Read results on Dynatech MR7000 ELISA reader with test filter at 410 nM and reference filter at 630 nM.

PYK2 Bioassay

This assay is used to measure the in vitro kinase activity of HA epitope-tagged full length pyk2 (FL.pyk2-HA) in an ELISA assay.

Materials and Reagents:
1. Corning 96-well ELISA plates.
2. 12CA5 monoclonal anti-HA antibody (SUGEN, Inc.)
3. PBS (Dulbecco's Phosphate-Buffered Saline (Gibco Catalog # 450-1300EB)
4. TBST Buffer: for 1 L, mix 8.766 g NaCl, 6.057 g TRIS and 1 ml of 0.1% Triton X-100 in approx. 900 ml dH$_2$O. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue H$_2$O.
8. 10 mM ATP in dH$_2$O.
9. 1M MnCl$_2$.
10. 1M MgCl$_2$.
11. 1M Dithiothreitol (DTT).
12. 10× Kinase buffer phosphorylation: mix 5.0 ml 1M Hepes (pH 7.5), 0.2 ml 1M MnCl$_2$, 1.0 ml 1M MgCl$_2$, 1.0 ml 10% Triton X-100 in 2.8 ml dH2O. Just prior to use, add 0.1 ml 1M DTT.
13. NUNC 96-well V bottom polypropylene plates.
14. 500 mM EDTA in dH$_2$O.
15. Antibody dilution buffer: for 100 mL, 1 mL 5% BSA/PBS and 1 mL 10% Tween-20 in 88 mL TBS.
16. HRP-conjugated anti-Ptyr (PY99, Santa Cruz Biotech Cat. No. SC-7020).
17. ABTS, Moss, Cat. No. ABST-2000.
18. 10% SDS.

Procedure:
1. Coat Corning 96 well ELISA plates with 0.5 µg per well 12CA5 anti-HA antibody in 100 µl PBS. Store overnight at 4° C.
2. Remove unbound HA antibody from wells by inverting plate. Wash plate with dH$_2$O. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 Bioassay
This assay is used to measure the in vitro kinase activity of FGF1-R in an ELISA assay.

Materials and Reagents:
1. Costar 96-well ELISA plates (Corning Catalog # 3369).
2. Poly(Glu-Tyr) (Sigma Catalog # PO275).
3. PBS (Gibco Catalog # 450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer.
Mix 500 µl 1M Hepes (GIBCO), 20 µl 5% BSA/PBS, 10 µl 100 mM sodium orthovanadate and 50 µl 5M NaCl.
8. 10 mM ATP
9. ATP/MnCl$_2$ phosphorylation mix: mix 20 µL ATP, 400 µL 1M MnCl$_2$ and 9.56 ml dH$_2$O.
10. NUNC 96-well V bottom polypropylene plates (Applied Scientific Catalog # AS-72092).
11. 0.5M EDTA.
12. 0.05% TBST
Add 500 µL TWEEN to 1 liter TBS.
13. Rabbit polyclonal anti-phosphotyrosine serum (SUGEN, Inc.).
14. Goat anti-rabbit IgG peroxidase conjugate (Biosource, Catalog # ALI0404).
15. ABTS Solution.
16. ABTS/H$_2$O$_2$ solution.

Procedure:
1. Coat Costar 96 well ELISA plates with 1 µg per well Poly(Glu-Tyr) in 100 µl PBS. Store overnight at 4° C.
2. Wash coated plates once with PBS.
3. Add 150 µL of 5% BSA/PBS Blocking Buffer to each well. Incubate, with shaking, for 1 hr at room temperature.
4. Wash plate 2× with PBS, then once with 50 mM Hepes. Pat plates on a paper towel to remove excess liquid and bubbles.
5. Add 25 µL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 µL of diluted kinase to each well.
8. Start kinase reaction by adding 25 µl/well of freshly prepared ATP/Mn++ (0.4ml 1M MnCl$_2$, 40 µL 10 mM ATP, 9.56 ml dH$_2$O), freshly prepared).
9. Stop reaction with 25 µL of 0.5M EDTA.
10. Wash plate 4× with fresh TBST.
11. Make up Antibody Dilution Buffer: For 50 ml, mix 5 ml of 5% BSA, 250 µl of 5% milk and 50 µl of 100 mM sodium vanadate, bring to final volume with 0.05% TBST.
12. Add 100 µl per well of anti-phosphotyrosine (1:10000 dilution in ADB). Incubate, with shaking for 1 hr. at room temperature.
13. Wash as in step 10.
14. Add 100 µl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 µl of ABTS/H$_2$O$_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

PDGFR Bioassay
This assay is used to the in vitro kinase activity of PDGFR in an ELISA assay.

Materials and Reagents:
1. Corning 96-well ELISA plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 μl 1M TRIS, 200 μl 5M NaCl, 100 μl 1M $MnCl_2$ and 50 μl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/$H_2O_2$.
19. 0.2M HCl.

Procedure:
1. Coat Corning 96 well ELISA plates with 0.5 μg 28D4C10 in 100 μl PBS per well, hold overnight at 4° C.
2. Remove unbound 28D4C10 from wells by inverting plate to remove liquid. Wash 1× with $dH_2O$. Pat the plate on a paper towel to remove excess liquid.
3. Add 150 μl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 μg lysate/100 μl HNTG).
6. Add 100 μl of diluted lysate to each well. Shake at room temperature for 60 min.
7. Wash plates as described in Step 4.
8. Add 80 μl working kinase buffer mix to ELISA plate containing captured PDGFR.
9. Dilute test compound 1:10 in TBS in 96-well polypropylene plates.
10. Add 10 μl diluted test compound to ELISA plate. To control wells, add 10 μl TBS+10% DMSO. Incubate with shaking for 30 minutes at room temperature.
11. Add 10 μl ATP directly to all wells except negative control well (final well volume should be approximately 100 μl with 20 μM ATP in each well.) Incubate 30 minutes with shaking.
12. Stop reaction by adding 10 μl of EDTA solution to each well.
13. Wash 4× with deionized water, twice with TBST.
14. Add 100 μl anti-phosphotyrosine (1:3000 dilution in TBST) per well. Incubate with shaking for 30–45 min. at room temperature.
15. Wash as in Step 4.
16. Add 100 μl Biosource Goat anti-rabbit IgG peroxidase conjugate (1:2000dilution in TBST) to each well. Incubate with shaking for 30 min. at room temperature.
17. Wash as in Step 4.
18. Add 100 μl of ABTS/$H_2O_2$ solution to each well.
19. Incubate 10 to 30 minutes with shaking. Remove any bubbles.
20. If necessary stop reaction with the addition of 100 μl 0.2M HCl per well.
21. Read assay on Dynatech MR7000 ELISA reader with test filter at 410 nM and reference filter at 630 nM.

CDK2/ Cyclin A Assay

This assay is used to measure the in vitro serine/threonine kinase activity of human cdk2/ cyclin A in a Scintillation Proximity Assay (SPA).

Materials and Reagents.
1. Wallac 96-well polyethylene terephthalate (flexi) plates (Wallac Catalog # 1450-401).
2. Amersham Redivue [$\gamma^{33}$P] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/ cyclin A enzyme complex purified from Sf9 cells (SUGEN, Inc.).
5. Biotinylated peptide substrate (Debtide). Peptide biotin-X-PKTPKKAKKL is dissolved in $dH_2O$ at a concentration of 5 mg/ml.
6. 20% DMSO in $dH_2O$.
7. Kinase buffer: for 10 ml, mix 9.1 ml $dH_2O$, 0.5 ml TRIS (pH 7.4), 0.2 ml 1M $MgCl_2$, 0.2 ml 10% NP40 and 0.02 ml 1M DTT, added fresh just prior to use.
8. 10 mM ATP in $dH_2O$.
9. 1M Tris, pH adjusted to 7.4 with HCl.
10. 1M $MgCl_2$.
11. 1M DTT.
12. PBS (Gibco Catalog # 14190-144).
13. 0.5M EDTA.
14. Stop solution: For 10 ml, mix 9.25 ml PBS, 0.05 ml 10 mM ATP, 0.1 ml 0.5M EDTA, 0.1 ml 10% Triton X-100 and 1.5 ml of 50 mg/ml SPA beads.

Procedure:
1. Prepare solutions of test compounds at 4× the desired final concentration in 5% DMSO. Add 10 μL to each well. For positive and negative controls, use 10 μL 20% DMSO alone in wells.
2. Dilute the peptide substrate (deb-tide) 1:250 with $dH_2O$ to give a final concentration of 0.02 mg/ml.
3. Mix 24 μL 0.1 mM ATP with 24 μCi $\gamma^{33}$P ATP and enough $dH_2O$ to make 600 μL.
4. Mix diluted peptide and ATP solutions 1:1 (600 μL+600 μL per plate). Add 10 μL of this solution to each well.
5. Dilute 5 μL of cdk2/ cyclin A solution into 2.1 ml 2× kinase buffer (per plate). Add 20 μL enzyme per well. For negative controls, add 20 μL 2× kinase buffer without enzyme.
6. Mix briefly on a plate shaker; incubate for 60 minutes.
7. Add 200 μL stop solution per well.
8. Let stand at least 10 min.
9. Spin plate at approx. 2300 rpm for 10–15 min.
10. Count plate on Trilux reader.

MET Transphosphorylation Assay

This assay is used to measure phosphotyrosine levels on a poly(glutamic acid:tyrosine, 4:1) substrate as a means for identifying agonists/antagonists of met transphosphorylation of the substrate.

Materials and Reagents:
1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain, SUGEN, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1M sodium orthovanadate and 1 mL 5M sodium chloride in 88.4 mL $dH_2O$.
11. 4× ATP Reaction Mixture: for 10 mL, mix 0.4 mL 1M manganese chloride and 0.02 mL 0.1M ATP in 9.56 mL $dH_2O$.
12. 4× Negative Controls Mixture: for 10 mL, mix 0.4 mL 1M manganese chloride in 9.6 mL $dH_2O$.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2 μL $H_2O_2$ five minutes before use.
20. 0.2M HCl Procedure:
1. Coat ELISA plates with 2 μg Poly(Glu-Tyr) in 100 μL PBS, hold overnight at 4° C.
2. Block plate with 150 μL of 5% BSA/PBS for 60 min.
3. Wash plate twice with PBS then once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in dH2O) for controls to plate.
6. Incubate the kinase/compound mixture for 15 minutes.
7. Add 25 μL of 40 mM $MnCl_2$ to the negative control wells.
8. Add 25 μL ATP/$MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/$H_2O_2$ solution to each well.
16. If necessary, stop the development reaction with the addition of 100 μl of 0.2M HCl per well.
17. Read plate on Dynatech MR7000 ELISA reader with the test filter at 410 nM and the reference filter at 630 nM.

IGF-1 Transphosphorylation Assay
This assay is used to measure the phosphotyrosine level in poly(glutamic acid:tyrosine, 4:1) for the identification of agonists/antagonists of gst-IGF-1transphosphorylation of a substrate.

Materials and Reagents:
1. Corning 96-well ELISA plates.
2. Poly(Glu-Tyr), 4:1, Sigma Cat. No. P 0275.
3. PBS, Gibco Catalog # 450-1300EB.
4. 50 mM HEPES
5. TBB Blocking Buffer: for 1 L, mix 100 g BSA, 12.1 gTRIS (pH 7.5), 58.44 g sodium chloride and 10 mL 1% TWEEN-20.
6. Purified GST fusion protein containing the IGF-1 kinase domain (SUGEN, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2× Kinase Dilution Buffer: for 100 mL, mix 10 mL 1M HEPES (pH 7.5), 0.4mL 5% BSA in $dH_2O$, 0.2 mL 0.1M sodium orthovanadate and 1 mL 5M sodium chloride with enough $dH_2O$ to make 100 mL.
11. 4× ATP Reaction Mixture: for 10 mL, mix 0.4 mL 1M $MnCl_2$ and 0.008 mL 0.01M ATP and 9.56 mL $dH_2O$.
12. 4× Negative Controls Mixture: mix 0.4 mL 1M $MnCl_2$ in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk in PBS and 0.1 mL 0.1M sodium orthovanadate in 88.4 mL TBST.
16. Rabbit Polyclonal antiphosphotyrosine antibody, SUGEN, Inc.
17. Goat anti-rabbit HRP conjugated antibody, Biosource.
18. ABTS Solution.
20. ABTS/$H_2O_2$: mix 15 mL ABTS with 2 μL $H_2O_2$ 5 minutes before using.
21. 0.2M HCl in $dH_2O$.

Procedure:
1. Coat ELISA plate with 2.0 μg/well Poly(Glu, Tyr), 4:1 (Sigma P0275) in 100 μl PBS. Store plate overnight at 4° C.
2. Wash plate once with PBS.
3. Add 100 μl of TBB Blocking Buffer to each well. Incubate plate for 1 hour with shaking at room temperature.
4. Wash plate once with PBS, then twice with 50 mM Hepes buffer pH 7.5.
5. Add 25 μL of test compound in 4% DMSO (obtained by diluting a stock solution of 10 mM test compound in 100% DMSO with $dH_2O$) to plate.
6. Add 10.0 ng of gst-IGF-1 kinase in 50 μl Kinase Dilution Buffer to all wells.
7. Start kinase reaction by adding 25 μl 4× ATP Reaction Mixture to all test wells and positive control wells. Add 25 μl 4× Negative Controls Mixture to all negative control wells. Incubates for 10 minutes, with shaking, at room temperature.

8. Add 25 μl 0.5M EDTA (pH 8.0) to all wells.

9. Wash plate 4× with TBST Buffer.

10. Add rabbit polyclonal anti-phosphotyrosine antisera at a dilution of 1:10,000 in 100 μl Antibody Dilution Buffer to all wells. Incubate, with shaking, at room temperature for 1 hour.

11. Wash plate as in step 9.

12. Add 100 μL Biosource anti-rabbit HRP at a dilution of 1:10,000 in Antibody dilution buffer to all wells. Incubate, with shaking, at room temperature for 1 hour.

13. Wash plate as in step 9, follow with one wash with PBS to remove bubbles and excess Tween-20.

14. Develop by adding 100 μl/well ABTS/$H_2O_2$ to each well

15. After about 5 minutes, read on ELISA reader with test filter at 410 nm and referenced filter at 630 nm.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:

1. The appropriate ligand.

2. The appropriate engineered cells.

3. BrdU Labeling Reagent: 10 mM, in PBS, pH7.4 (Roche Molecular Biochemicals, Indianapolis, Ind.).

4. FixDenat: fixation solution (Roche Molecular Biochemicals, Indianapolis, Ind.).

5. Anti-BrdU-POD: mouse monoclonal antibody conjugated with peroxidase (Chemicon, Temecula, Calif.).

6. TMB Substrate Solution: tetramethylbenzidine (TMB, ready to use, Roche Molecular Biochemicals, Indianapolis, Ind.).

7. PBS Washing Solution: 1× PBS, pH 7.4.

8. Albumin, Bovine (BSA), fraction V powder (Sigma Chemical Co., USA).

General Procedure:

1. Cells are seeded at 8000 cells/well in 10% CS, 2 mM Gln in DMEM, in a 96 well plate. Cells are incubated overnight at 37° C. in 5% $CO_2$.

2. After 24 hours, the cells are washed with PBS, and then are serum-starved in serum free medium (0% CS DMEM with 0.1% BSA) for 24 hours.

3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.

4. After 18 hours of ligand activation, diluted BrdU labeling reagent (1:100 in DMEM, 0.1% BSA) is added and the cells are incubated with BrdU (final concentration is 10 μM) for 1.5 hours.

5. After incubation with labeling reagent, the medium is removed by decanting and tapping the inverted plate on a paper towel. FixDenat solution is added (50 μl/well) and the plates are incubated at room temperature for 45 minutes on a plate shaker.

6. The FixDenat solution is removed by decanting and tapping the inverted plate on a paper towel. Milk is added (5% dehydrated milk in PBS, 200 μl/well) as a blocking solution and the plate is incubated for 30 minutes at room temperature on a plate shaker.

7. The blocking solution is removed by decanting and the wells are washed once with PBS. Anti-BrdU-POD solution is added (1:200 dilution in PBS, 1% BSA, 50 μl/well) and the plate is incubated for 90 minutes at room temperature on a plate shaker.

8. The antibody conjugate is removed by decanting and rinsing the wells 5 times with PBS, and the plate is dried by inverting and tapping on a paper towel.

9. TMB substrate solution is added (100 μl/well) and incubated for 20 minutes at room temperature on a plate shaker until color development is sufficient for photometric detection.

10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:

1. Mouse EGF, 201 (Toyobo Co., Ltd., Japan).

2. 3T3/ EGFRc7.

Remaining Materials and Reagents and Procedure, as above.

PDGF-Induced BrdU Incorporation Assay

Materials and Reagents:

1. Human PDGF B/B (Boehringer Mannheim, Germany).

2. 3T3/ EGFRc7.

Remaining Materials and Reagents and Procedure, as above.

FGF-Induced BrdU Incorporation Assay

Materials and Reagents:

1. Human FGF2/ bFGF (Gibco BRL, USA).

2. 3T3c7/ EGFr

Remaining Materials and Reagents and Procedure, as above.

IGF1-Induced BrdU Incorporation Assay

Materials and Reagents:

1. Human, recombinant (G511, Promega Corp., USA)

2. 3T3/ IGF1r.

Remaining Materials and Reagents and Procedure, as above.

Src Transphosphorylation Assay

This assay is used to screen for inhibitors of the tyrosine kinase Src.

Materials and Reagents:

1. Coating buffer: PBS containing sodium azide (0.2 mg/ml).

2. 1% w/v BSA in PBS.

3. Wash buffer: PBS containing 0.05% v/v Tween 20 (PBS-TWEEN)

4. 500 mM HEPES pH7.4.

5. ATP (40 μM)+$MgCl_2$ (80 mM) in distilled water.

6. $MgCl_2$ (80 mM) in distilled water (for no ATP blanks).

7. Test compounds, 10 mM in DMSO.

8. Assay Buffer: 100 mM HEPES, pH 7.4, containing 2 mM DTT, 0.2 mM sodium orthovanadate and 0.2 mgs/ml BSA.

9. Partially purified recombinant human Src (UBI (14-117)

10. Anti-phosphotyrosine (SUGEN rabbit polyclonal anti-PY).

11. HRP-linked goat anti-rabbit Ig (Biosource International #6430)

12. HRP substrate ABTS or Pierce Peroxidase substrate.

13. Corning ELISA plates.

Procedure:

1. Coat plates with 100 μl of 20 μg/ml poly(Glu-Tyr) (Sigma Cat. No.P0275) containing 0.01% sodium azide. Hold overnight at 4° C.

2. Block with 1% BSA at 100 μl/well for one hour at room temperature.

3. Plate test compounds (10 mM in DMSO) at 2 ul/well on a Costar plate ready for dilution with dH$_2$O and plating to reaction plates.

4. Dilute Src kinase 1:10,000 in Reaction Buffer, for 5 plates prepare 25 ml as follows: 2.5 mls 1M HEPES pH7.4 (stored sterile at 4° C.), 21.85 ml distilled water, 0.1 ml 5% BSA, 0.5 ml 10 mM sodium orthovanadate (stored sterile at 4° C.), 50 μl 1.0M DTT (stored 5. Add 48 μl of distilled water to the 2 μl of each compound in the dilution plate then add 25 μl/well of this to the reaction plate.

6. Add 50 μl of HRP to each reaction buffer well and then 25 μl ATP-MgCl$_2$/well (MgCl$_2$ only to no ATP blanks). Incubate at room temperature for 15 minutes on plate shaker. Stop reaction by adding 25 μl of 0.5M EDTA to each well.

7. Wash 4× with PBS-TWEEN.

8. Add 100 μl anti-phosphotyrosine (1:10,000 of anti-pTyr serum or 1:3,000 of 10% glycerol diluted PA-affinity purified antibody) in PBS-TWEEN containing 0.5% BSA, 0.025% Non-fat milk powder and 100 μM sodium orthovanadate. Incubate with continuous shaking at room temperature for one hour.

9. Wash plates 4× with PBS-TWEEN.

10. Add 100 μl HRP-linked Ig (1:5,000) in PBS-TWEEN containing 0.5% BSA, 0.025% Non-fat milk powder, 100 μM sodium orthovanadate. Incubate with shaking at room temperature for one hour.

11. Wash plates 4× with PBS-TWEEN and then once with PBS.

12. Develop plate using ABTS or other peroxidase substrate.

Cell Cycle Analysis:

A431 cells in standard growth medium are exposed to a desired concentration of a test compound for 20–24 hours at 37° C. The cells are then collected, suspended in PBS, fixed with 70% ice-cold methanol and stained with propidium iodide. The DNA content is then measured using a FACScan flow cytometer. Cell cycle phase distribution can then be estimated using CellFIT software (Becton-Dickinson).

HUV-EC-C Assay

This assay is used to measure a compound's activity against PDGF-R, FGF-R, VEGF, aFGF or Flk-1/KDR, all of which are naturally expressed by HUV-EC cells.

Day 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm$^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm$^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm$^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of $0.8–1.0\times10^5$ cells/ml.

3. Add cells to 96-well flat-bottom plates at 100 μl/well or $0.8–1.0\times10^4$ cells/well, incubate ~24 h at 37° C., 5% CO$_2$.

Day 1

1. Make up two-fold test compound titrations in separate 96-well plates, generally 50 μM on down to 0 μM. Use the same assay medium as mentioned in day 0, step 2 above. Titrations are made by adding 90 μl/well of test compound at 200 μM (4× the final well concentration) to the top well of a particular plate column. Since the stock test compound is usually 20 mM in DMSO, the 200 μM drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 μl/well. Take 60 μl from the 120 μl of 200 μM test compound dilution in the top well of the column and mix with the 60 μl in the second well of the column. Take 60 μl from this well and mix with the 60 μl in the third well of the column, and so on until two-fold titrations are completed. When the next-to-the-last well is mixed, take 60 μl of the 120 μl in this well and discard it. Leave the last well with 60 μl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 μl/well of the test compound dilutions to the 96-well assay plates containing the $0.8–1.0\times10^4$ cells/ 100 μl/well of the HUV-EC-C cells from day 0 and incubate ~2 h at 37° C., 5% CO$_2$.

3. In triplicate, add 50 μl/well of 80 μg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% CO$_2$. Each well will have 50 μl test compound dilution, 50 μl growth factor or media, and 100 μl cells, which calculates to 200 μl/well total. Thus the 4× concentrations of test compound and growth factors become 1× once everything has been added to the wells.

Day 2

1. Add $^3$H-thymidine (Amersham, catalogue no. TRK-686) at 1 μCi/well (10 μl/well of 100 μCi/ml solution made up in RPMI media+10% heat-inactivated fetal bovine serum) and incubate ~24 h at 37° C., 5% $CO_2$. RPMI is obtained from Gibco BRL, catalogue no. 11875-051.

Day 3

1. Freeze plates overnight at −20° C.

Day 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells, S114 (NIH3T3 fibroblast cell line genetically engineered for cMet and HGF expressions from NCI), U-87MG (human malignant glioma, ATCC HTB 14) and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Met Phosphorylation—Cellular Assay

Materials and Reagents:

1. Falcon 10 cm culture dishes.
2. A549 lung carcinoma cells.
3. F12K growth medium (with 2% FBS+2 mM glutamine.
4. F12K assay medium (with 0.1% BSA).
5. Fisher cell scrapers.
6. Lysis buffer (HNTG, 1 mM sodium orthovanidate, 1 mM PMSF and 2 mM sodium fluoride).
7. 1.5 ml Eppendorf tubes.
8. Eppendorf microcentrifuge.
9. BCA assay reagents A and B (#23223 and 23224, Pierce).
10. Sample tube rotator.
11. Gel blot container rotator.
12. 5× sample buffer.
13. Novex pre-cast tris-glycine 8% acrylamide gels.
14. Bio-Rad electrophoresis chamber.
15. SDS-PAGE buffer.
16. TBS (pH 7.6)+0.1% Triton X-100 (TBST), with and wihtout 5% milk.
17. Western blot transfer buffer.
18. Osmonics nitrocellulose paper.
19. Bio-Rad Transblot paper.
20. Gel transfer apparatus.
21. Anti-phosphotyrosine (mouse monoclonal).
22. Bio-Rad Kaleidoscope Prestained Standards (161-0324).
23. Anti-h-met (C-28) rabbit polyclonal, conjugated and non-conjugated with agarose (#sc-161 AC and sc-161, Santa Cruz Biotechnology, Inc.).
24. Donkey and anti-rabbit Ig-HRP (NA 934, Amersham).
25. Sheet anti-mouseIg-HRP (NA 931, Amersham).

26. SuperSignal West Pico Chemiluminescent Substrate (#34080, Pierce).
27. Saran Wrap.
28. Kodak BioMax exposure cassette.
29. Fuji X-ray film.
30. Kodak film developer.

Procedure:
1. Plate cells in 10 cm dishes with growth medium with 2% FBS+2 mM glutamine. Grow to near confluency.
2. Serum starve cells overnight in assay medium with 0.1% BSA.
3. Add drug to the plates, one dose per plate, usually in a 2-flod titration. Add asay medium (with the same DMSO concentration as the drugs) for no drug.
4. Incubate plates 4–5 hours with the drug, then add HG, 50 ng/ml for 10 minutes.
5. Wash plates once with PBS, add 400 µl lysis buffer, and scrape off the cells. Collect in 1.5 ml Eppendorf tubes.
6. After about 10–20 minutes in the lysis buffer, centrifuge lysates in a microcentrifuger at full speed (14,000 g) and collect the supernatants in a separate Eppendorf tube.
7. Determine protein concentration with the BCA assay reagents.
8. Adjust sample concentration to 0.5 mg protein in 0.4 ml using lysis buffer.
9. Add 15 µl anti-h-met AC for immunoprecipitation, rotate samples for 2 hours at 4° C.
10. Wash samples 3 times with lysis buffer and resuspend in 35 µl 5× sample buffer.
11. Boil sample at 100° C. for 10 minutes and microcentrifuge at highest setting for 30 minutes to pellet the agarose beads.
12. Load 15 µl each to 2 gels, one for anti-phosphorylation and the other for anti-h-met. Also load 10 µl of prestained standards, one lane per gel.
13. Run gel around 100–125 V, then transfer gel to nitrocellulose either overnight at 70 mAmps or 1 hour at 500 mAmps.
14. Block membranes on rotator for 1 hour in TBS+0.1% Triton X-100 (TBST)+5% PBS. All steps from this point are at room temperature unless otherwise unless otherwise noted.
15. Add 0.8 µg/ml antiphosphotyrosine and 0.25 µg/ml anti-h-met on rotator either for 2 hours or overnight.
16. Wash membranes 3 times 5 minutes each in TBST on rotator.
17. Add HRP-conjugated antibodies) sheep anti-mouse for the antiphosphotyroeins; donkey anti-rabbit for the nati-h-met) at 1:5000 for approximately 45 minutes on rotator.
18. Wash membranes 3 times for 5 minutes each in TBST on rotator.
19. Add the 2 reagents in th3e SuperSignal kit together in equal volumes (3 ml+3 ml for each blot), rotate for 1–2 minutes.
20. Wrap blots in Saran Wrap and tape securely inside the exposure cassette.
21. In the darkroom with only the safety light on, place a sheet of film inside the cassette. After an allotted time, remove film and place in the developer machine for automatic processing. Experiment with the exposure time to get proper exposure.

ZC1 Scintilation Proximity Assay

The Scintillation Proximity assay (SPA) is used to analyze the protein serine/threonine kinase activity of ZC1 in vitro to screen for inhibitors of ZC1 in a homogeneous assay. The assay described below is amenable for high throughput screening of ZC1 Inhibitors.

Materials and Solutions:
1. Wallac 96-well polyethylene terephthalate (flexi) plates (Wallac Catalog #1450-401)
2. NEN Easy-Tide [$\gamma 33P$] ATP (NEN Catalog #NEG602H)
3. Amersham streptavidin coated polyvinyltoluene SPA beads (Amersham catalog #NIF 107)—Reconstitute beads in PBS without magnesium or calcium, at 50 mg/mL. Store reconstituted beads at 4° C. (To achieve optimal counts, it is important that excess streptavidin SPA bead should be present in order to bind all of the biotinylated molecules in the assay.) Activated ZC1 enzyme purified from Sf9 cells—Final concentration of 300 ng/well.
4. Peptide substrate #902B (biotin-KRTLRRKRTLR-RKRTLRR)—Final concentration of 0.5 µM/well (2×Km)

Procedure:
1. Prepare solutions of inhibitors at 5× the desired final concentration in 5% DMSO. Add 10 µL to each well of the flexiplate. For positive and negative controls, add 10 µL 5% DMSO.
2. Prepare ATP mix as shown above (2.1 ml of ATP mix is sufficient for one assay plate). Add 20 µL to all wells.
3. Add 20 µL of 5M EDTA to negative control wells.
4. Prepare the enzyme solution in 2.5× kinase buffer (50 mM HEPES pH 7.4, 12.5 mM $MnCl_2$, 500 mM NaCl, and 1 mM DTT. The final enzyme concentration will be 0.30 µg/well (For example, given a 0.5 mg/mL stock, add 302 µL ZC1 enzyme to 10 mL Kinase Buffer.) Add 20 µL per well to start the reaction.
5. Allow kinase reaction to proceed at room temperature for 60 minutes.
6. To each well, add 200 µL of a stop solution containing 0.05 mM ATP, 5 mM EDTA, 0.1% Triton x-100, and 5 mg per ml Amersham streptavidin-coated polyvinyltoluene SPA beads (Cat # NIF 1077) in PBS. Incubate for 15 minutes.
7. Spin plate at 2300 rpm for 15 min.
8. Count plate on Trilux reader using SPA flexiplate protocol (including quench curve).

Aurora2 Scintilation Proximity Assay

The Scintillation Proximity assay (SPA) is used to analyze the protein serine/threonine kinase activity of Aurora2 in vitro to screen for inhibitors of Aurora2 in a homogeneous assay. The assay described below is amenable for high throughput screening of Aurora2 Inhibitors.

Materials and Solutions:
1. Wallac 96-well polyethylene terephthalate (flexi) plates (Wallac Catalog #1450-401)
2. NEN Easy-Tide [$\gamma^{33}P$] ATP (NEN Catalog #NEG602H)
3. Amersham streptavidin coated polyvinyltoluene SPA beads (Amersham catalog #NIF 107)—Reconstitute beads in PBS without magnesium or calcium, at 50 mg/mL. Store reconstituted beads at 4° C. (To achieve optimal counts, it is important that excess streptavidin SPA bead should be present in order to bind all of the biotinylated molecules in the assay.)
4. Enzyme: GST-Aurora2 enzyme purified from BL21 cells. 1.0 mg/ml; 500 µl aliquots. Use 0.125 mg/assay well.
5. Biotinylated peptide substrate: SUGEN peptide #800A. Biotin-LC-LC-LRRWSLGLRRWSLGLRRWSLGLR-RWSLG dissolved in DMSO at a concentration of 10 mg/ml. Stored at −20° C. in 500 µl aliquots-Final concentration of 0.012 mlg/well (2×Km).

Procedure:

1. Prepare solutions of inhibitors at 5× the desired final concentration in 5% DMSO. Add 10 μL to each well of the flexiplate. For positive and negative controls, add 10 μL 5% DMSO.

2. Prepare ATP mix as shown above (2.1 ml of ATP mix is sufficient for one assay plate). Add 20 μL to all wells.

| Reagent | Stock Solution | Amount per 10 ml | Working Concentration | Final Concentration |
|---|---|---|---|---|
| $dH_2O$ | | 9.94 ml | | |
| ATP | 10 mM | 0.015 ml | 0.015 mM | 0.006 mM |
| Peptide 800A | 10 mg/ml | 0.03 ml | 0.03 mg/ml | 0.012 mg/ml |
| $^{33}P$ ATP | 10 μCi/μl | 0.0165 ml | 16.5 μCi/ml | 6.6 μCi/μl |

3. Add 20 μL of 5M EDTA to negative control wells.

4. Prepare the enzyme solution in 2.5× kinase buffer (50 mM HEPES pH 7.4, 12.5 mM $MnCl_2$, 500 mM NaCl, and 1 mM DTT. The final enzyme concentration will be 0.125 μg/well. Add 20 μL per well to start the reaction.

5. Allow kinase reaction to proceed at room temperature for 60 minutes.

6. To each well, add 200 μL of a stop solution containing 0.05 mM ATP, 5 mM EDTA, 0.1% Triton x-100, and 5 mg per ml Amersham streptavidin-coated polyvinyltoluene SPA beads (Cat # NIF 1077) in PBS. Incubate for 15 minutes.

7. Spin plate at 2300 rpm for 15 min.

8. Count plate on Trilux reader using SPA flexiplate protocol.

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. Pat. No. 6,130,238, which is incorporated by reference, including any drawings, herein. Additionally, U.S. Pat. No. 5,792,783, filed Jun. 5, 1996 and U.S. Pat. No. 6,395,734, filed May 28, 1999 are incorporated by reference as if fully set forth herein.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

The invention claimed is:

1. A compound selected from the group consisting of Formula IV and VI:

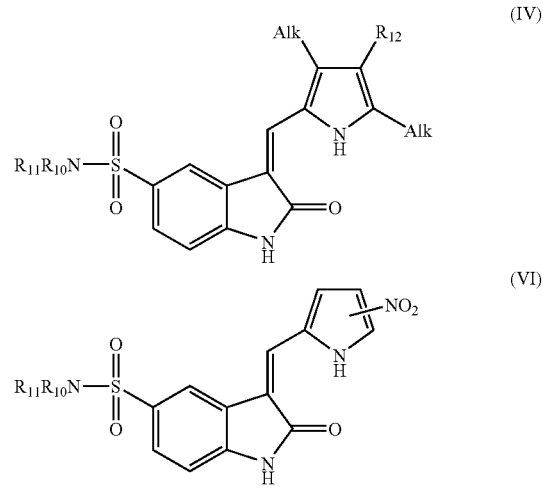

wherein
$R_{10}$–$R_{11}$ are independently selected from the group consisting of H, lower alkyl, phenyl substituted with halo, thiazolyl and cycloalkyl;
$R_{12}$ is selected from the group consisting of —$CH_2$—C(O)—X'—$(CH_2)_n$-Z, —$CH_2$-Z,

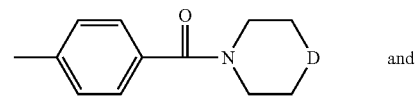 and

-continued

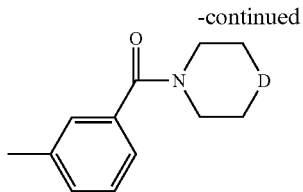

where D is O or N—CH$_3$;

X' is NH, S, O or a bond;

Z is a polar group selected from the group consisting of —C(O)OR$_{13}$, —C(O)NR$_{13}$R$_{14}$, amino, alkylamino, dialkylamino, piperazinyl, pyrrolidinyl and morpholinyl, Z may be further substituted by —(CH$_2$)$_{0-1}$-Z$_1$, where Z$_1$ is a polar group selected from the group consisting of —C(O)OR$_{13}$, —C(O)NR$_{13}$R$_{14}$, amino, alkylamino, dialkylamino, hydroxy, piperazinyl, pyrrolidinyl and morpholinyl; when Z is further substituted, R13 is not present;

R13 is lower alkyl;

R14 is H or lower alkyl;

n is 0–3; and

Alk is lower alkyl of 1–4 carbons;

and pharmaceutically acceptable salts thereof.

2. A compound selected from the group consisting of
5-(2,3-Dihydro-indole-1-sulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one;

2-{5-[5-[3-Chloro-phenyl)-methyl-sulfamoyl]-2-oxo-1,2-dihydro-indol-(3Z)-ylidenemethyl]-2,4-dimethyl-1H-pyrrol-3-yl}-N-(2-diethylamino-ethyl)-acetamide;

3-[1-[3-(2-Hydroxy-ethyl)-4-(4-methyl-piperazine-1-carbonyl)-1H-pyrrol-2-yl]-meth-(Z)-ylidene]-5-(5-methoxy-2,3-dihydro-indole-1-sulfonyl)-1,3-dihydro-indol-2-one;

5-[5-(5-Methoxy-2,3-dihydro-indole-1-sulfonyl)-2-oxo-1,2-dihydro-indol-(3Z)-ylidenemethyl]-2,4-dimethyl-1H-pyrrole-3-carboxylic acid (2-diethylamino-ethyl)-amide;

5-[5-(2,3-Dihydro-indole-1-sulfonyl)-2-oxo-1,2-dihydro-indol-(3Z)-ylidenemethyl]-2-methyl-4-[3-(4-methyl-piperazin-1-yl)-propyl]-1H-pyrrole-3-carboxylic acid ethyl ester;

5-(2,3-Dihydro-indole-1-sulfonyl)-3-[1-[3-(3-morpholin-4-yl-propyl)-4,5,6,7-tetrahydro-1H-indol-2-yl]-meth-(Z)-ylidene]-1,3-dihydro-indol-2-one;

(3Z)-N-(3-chlorophenyl)-3-{[3,5-dimethyl-4-(3-morpholin-4-ylpropyl)-1H-pyrrol-2-yl]methylene}-N-methyl-2-oxoindoline-5-sulfonamide; and (3Z)-5-(2,3-dihydro-1H-indol-1-ylsulfonyl)-3-{[3,5-dimethyl-4-(3-morpholin-4-ylpropyl)-1H-pyrrol-2-yl]methylene}-1,3-dihydro-2H-indol-2-one.

* * * * *